US011786463B2

United States Patent
Chang et al.

(10) Patent No.: US 11,786,463 B2
(45) Date of Patent: Oct. 17, 2023

(54) PHARMACEUTICAL COMPOSITIONS FOR THE TREATMENT OF OPHTHALMIC CONDITIONS

(71) Applicant: Rhodes Technologies, Coventry, RI (US)

(72) Inventors: Ping Chang, Waterford, CT (US); Zhenze Hu, Davie, FL (US); Yuanyuan Tao, Drexel Hill, PA (US)

(73) Assignee: Rhodes Technologies, Coventry, RI (US)

( * ) Notice: Subject to any disclaimer, the term of this patent is extended or adjusted under 35 U.S.C. 154(b) by 0 days.

(21) Appl. No.: 16/642,168

(22) PCT Filed: Aug. 10, 2018

(86) PCT No.: PCT/US2018/046331
§ 371 (c)(1),
(2) Date: Feb. 26, 2020

(87) PCT Pub. No.: WO2019/045994
PCT Pub. Date: Mar. 7, 2019

(65) Prior Publication Data
US 2021/0299046 A1 Sep. 30, 2021

Related U.S. Application Data

(60) Provisional application No. 62/609,752, filed on Dec. 22, 2017, provisional application No. 62/550,642, filed on Aug. 27, 2017.

(51) Int. Cl.
| | | |
|---|---|---|
| *A61K 9/107* | (2006.01) | |
| *A61K 9/00* | (2006.01) | |
| *A61K 9/06* | (2006.01) | |
| *A61K 31/352* | (2006.01) | |
| *A61K 47/02* | (2006.01) | |
| *A61K 47/10* | (2017.01) | |
| *A61K 47/44* | (2017.01) | |
| *A61P 27/04* | (2006.01) | |
| *A61P 29/00* | (2006.01) | |

(52) U.S. Cl.
CPC .......... *A61K 9/1075* (2013.01); *A61K 9/0014* (2013.01); *A61K 9/0019* (2013.01); *A61K 9/0048* (2013.01); *A61K 9/06* (2013.01); *A61K 31/352* (2013.01); *A61K 47/02* (2013.01); *A61K 47/10* (2013.01); *A61K 47/44* (2013.01); *A61P 27/04* (2018.01); *A61P 29/00* (2018.01)

(58) Field of Classification Search
CPC ...... A61K 9/107; A61K 47/44; A61K 9/1075; A61K 31/352
See application file for complete search history.

(56) References Cited

U.S. PATENT DOCUMENTS

| | | | | |
|---|---|---|---|---|
| 2010/0303915 A1* | 12/2010 | Yu | ......................... | A61K 9/0048 424/489 |
| 2010/0305218 A1* | 12/2010 | Wooster | .................. | C11C 1/002 426/238 |
| 2012/0322866 A1* | 12/2012 | Rossi | .................... | C07D 311/80 514/454 |
| 2014/0248379 A1* | 9/2014 | Mueller | ............... | C07D 311/80 424/725 |
| 2015/0045282 A1 | 2/2015 | Elsohly et al. | | |
| 2015/0164846 A1* | 6/2015 | Wassel | .................... | A61K 47/14 514/545 |
| 2015/0352118 A1* | 12/2015 | Goris | .................... | A61K 9/0048 424/9.1 |
| 2016/0143977 A1 | 5/2016 | Gore et al. | | |

FOREIGN PATENT DOCUMENTS

| | | | | |
|---|---|---|---|---|
| CN | 1324236 | 11/2001 | | |
| CN | 1809552 | 7/2006 | | |
| CN | 101198324 | 6/2008 | | |
| CN | 101410104 | 4/2009 | | |
| CN | 106061490 | 10/2016 | | |
| EP | 0521799 A1 * | 1/1993 | ........... | A61K 9/1075 |
| EP | 0521799 A1 | 1/1993 | | |
| TW | 200718418 | 5/2007 | | |
| WO | WO-2016147186 A1 * | 9/2016 | ........... | A61K 9/1075 |

OTHER PUBLICATIONS

Rosenkratz et al. (Toxicology and Applied Pharmacology, Apr. 1974, vol. 28, pp. 18-27, abstract) (Year: 1974).*
Guidet et al (Critical Care, 2010, vol. 14, pp. 1-12) (Year: 2010).*
Vandamme TH.F., "microemulsions as ocular drug delivery systems: recent developments and future challenges", Progess in Retinal and Eye Research Oxford, GB, vol. 21, No. 1, Jan. 1, 2002.
Supplementary European Search Report dated Apr. 8, 2021 issued in connection with European Application No. EP18850117.
International Search Report and Written Opinion dated Oct. 16, 2018 issued in connection with International Application No. PCT/US2018/046331.
Search Report dated Sep. 29, 2022 in connection with Chinese Application No. 201880055577.9.
Office Action dated Jul. 31, 2023 in connection with Israel Patent Application No. 272601.

(Continued)

*Primary Examiner* — Mark V Stevens
(74) *Attorney, Agent, or Firm* — TROUTMAN PEPPER HAMILTON SANDERS LLP

(57) ABSTRACT

The invention provides emulsion compositions comprising at least one cannabinoid compound, and methods for making the same. The emulsion compositions are stable, well tolerated and are capable of delivering therapeutically effective amounts of cannabiniods to target sites, including sites on the surface of and/or within an eye. Also provided are methods of using the compositions to provide ocular neuroprotection and/or to treat ophthalmic conditions such as glaucoma.

20 Claims, 22 Drawing Sheets

(56) References Cited

OTHER PUBLICATIONS

Rosenkrantz H. et al.: "Oral and Parenteral Formulations of Marijuana Constituents," J. Pharm. Sci. 61(7):1106-1112 (1972).
Tomida I. et al., "Cannabinoids and Glaucoma," Br. J. Ophthalmol. 88:708-713 (2004).

* cited by examiner

PHARMACEUTICAL COMPOSITIONS FOR THE TREATMENT OF OPHTHALMIC CONDITIONS

CROSS-REFERENCE TO RELATED APPLICATIONS

This patent application is a U.S. National Phase of International Patent Application No. PCT/US2018/046331, filed Aug. 10, 2018, which claims priority pursuant to 35 U.S.C. § 119(e) to U.S. Provisional Patent Application No. 62/609,752, filed Dec. 22, 2017 and U.S. Provisional Patent Application No. 62/550,642, filed Aug. 27, 2017, all of which are herein incorporated by reference in their entireties.

FIELD OF THE INVENTION

The present invention provides pharmaceutical compositions comprising at least one cannabinoid compound, methods of use, and methods for making the same. In one embodiment, the pharmaceutical compositions of the invention are useful for treating ophthalmic conditions, such as, glaucoma. In certain embodiments, the pharmaceutical compositions are emulsion compositions that are stable, well tolerated and are capable of delivering therapeutically effective amount(s) of cannabinoid(s) to target sites, including sites on the surface of and/or within an eye of a mammal (e.g., a human). Also provided are methods of using the compositions to provide ocular neuroprotection, thereby treating or preventing ophthalmic conditions such as glaucoma.

BACKGROUND OF THE INVENTION

The prevalence of neuropathological ophthalmic conditions is an important public health issue. For example, glaucoma is one of the leading causes of blindness worldwide. In the United States alone, it is estimated that more than 3 million individuals are living with the disease. Glaucoma refers to a group of eye conditions that cause damage to the eye's optic nerve. This damage is caused by an abnormally high intraocular pressure (TOP) which eventually leads to optic nerve degeneration, resulting in vision loss and blindness.

Several lipophilic (and poorly water soluble) drugs have become available in recent years to treat glaucoma and other ophthalmic conditions. For example, isolated compounds from the *Cannabis* plant, such as tetrahydrocannabinol (THC), and other modulators of the cannabinoid receptors, CB1 and CB2, have been shown to reduce TOP and to have neuroprotective and anti-inflammatory properties, useful for the treatment of a variety of ophthalmic diseases (*J. Pharm. Sci.*, 2012, 101(2): 616-626; *Ophthalmic Res.*, 1992, 24: 142-149; *International J Pharm.*, 2010, 393: 238-243; United States Patent Publication No. 2016/0184259; U.S. Pat. No. 9,265,724; and *Br. J Ophthalmol.*, 2004, 88: 708-713). However, these, and other, lipophilic drugs present a formulation challenge for scientists because their low aqueous solubility prohibits simple eye drop solutions having sufficient drug concentrations in aqueous form. Most of the traditional lipophilic dosage forms for ocular application (e.g., oil solutions, lotions, and gels) are uncomfortable for the patient and do not provide adequate local drug concentrations to the eye. Therefore, low viscosity topical formulations in aqueous-based eye drops are generally preferred. For some lipophilic drugs, emulsions can offer a number of advantages, such as increased solubilization and improved ocular bioavailability. However, the design of emulsion formulations that are biologically compatible, stable and serializable remains a challenge.

Thus, new or improved ophthalmic drug delivery systems are continually needed that are stable, well tolerated, have enhanced activity, and other advantageous features. The compositions and methods described herein are directed towards these and other ends.

SUMMARY OF THE INVENTION

The present invention provides emulsion compositions comprising:
tetrahydrocannabinol (THC), or a derivative thereof;
an oil;
a surfactant; and
water,
wherein the emulsion comprises an oil phase component comprising a plurality of oil droplets, dispersed with an aqueous phase component, the emulsion remains stable after being stored at a condition selected from the group consisting of: at least two years at about −18° C.; at least three months at about 4° C.; and at least one month at about 23° C. (or room temperature), such that there is an absence of visible phase separation between the oil phase component and the aqueous phase component after such storage condition.

The emulsion compositions include oil-in-water-type emulsions and are suitable for topical administration to the eye, for example by way administration as an eye drop solution.

The ratio (w/w) of oil to water in the composition is typically in the range of about 1:10 to about 1:1000, or about 1:20 to about 1:100.

The emulsion compositions are microbiologically stable and can be prepared such that they are substantially free of antimicrobial preservative agents (e.g., benzalkonium chloride; thimerosal; chlorobutanol; methyl paraben; propyl paraben; phenylethyl alcohol; EDTA; and sorbic acid).

Some of the emulsion compositions are micro-emulsions, for example, where at least about 90% of the oil droplets in the emulsion are less than about 200 nm in diameter (or no greater than about 150 nm in diameter). In certain embodiments, the particle size distribution of the oil droplets remains essentially constant after exposure to most storage conditions commonly used in the art to store pharmaceutical emulsion compositions (such as, the storage conditions above delineated).

The emulsion compositions of the invention preferably comprise a therapeutically active THC compound, for example, (−)-trans-$\Delta^9$-tetrahydrocannabinol. THC may be present in the emulsion at a concentration of about 0.005% (w/w) to about 0.5% (w/w), about 0.005% (w/w) to about 0.05% (w/w), about 0.015% (w/w) to about 0.05% (w/w), about 0.005% (w/w) to about 0.015% (w/w), or about 0.05% (w/w) to about 0.5% (w/w). THC remains chemically stable in the emulsion compositions, such that at least about 90% (or about 95%) (w/w) of the initial THC content in the emulsion remains after exposure of the emulsion to one of the storage conditions above delineated.

The oil in the compositions of the invention is a pharmaceutically acceptable oil. For example, the oil is a vegetable oil, such as sesame oil, castor oil, soybean oil, olive oil, cotton seed oil, or peanut oil, or a combination thereof. The oil may be present in the composition at a concentration of about 1.5% (w/w) to about 5.0% (w/w).

The compositions optionally comprise a surfactant, selected from the group of ionic (e.g., anionic, cationic, amphoteric, and Zwitterionic) and nonionic surfactants. For example, the surfactant used in the composition is polysorbate 80, under trade names such as "Tween 80", or tyloxapol, at a concentration of about 0.5% (w/w) to about 5%. Co-solvents, such as glycerin, may also be added, e.g., at about 2.5% (w/w).

The compositions may also comprise one or more antioxidants, e.g., butylated hydroxyanisole (BHA) or butylated hydroxytoluene (BHT) at a concentration range of about 0.001% (w/w) to about 0.5% (w/w), or about 0.03% (w/w).

A pH adjusting agent (e.g., sodium hydroxide) may also be incorporated in the composition to afford a substantially neutral pH of about 6.8 to about 7.2.

The present invention further provides an emulsion composition comprising:
  a tetrahydrocannabinol (THC), or a derivative thereof;
  an oil;
  a surfactant; and
  water,
wherein the emulsion comprises an oil phase component comprising a plurality of oil droplets dispersed with an aqueous phase component, wherein the osmolarity of the emulsion is substantially similar to human tear fluid osmolarity (e.g., about 250 mOsm/L to about 330 mOsm/L).

The invention further includes a method of treating or preventing an ophthalmic condition in a subject in need of such treatment, the method comprising administering to the eye of the subject a therapeutically effective amount of the emulsion composition of the invention, wherein the method provides ocular neuroprotection to the subject (e.g., decreases or reverses ocular neurodegeneration in the subject).

The invention further provides a method of treating an ophthalmic condition in a patient in need of such treatment, the method comprising topically administering to the eye of the patient a therapeutically effective amount of the emulsion composition of the invention.

The ophthalmic condition can include ocular diseases, such as glaucoma, age-related macular degeneration (AMD), ophthalmitis, or conjunctivitis. The ophthalmic condition referred to herein also includes inflammatory diseases or disorders, such as, dry eye disease, posterior uveitis, retinitis, uveoretinitis, proliferative vitreoretinopathy, anterior uveitis, episcleritis, scleritis, ocular neuropathic pain, and ocular inflammation caused by non-infectious conditions. In one embodiment, the invention provides a method of treating glaucoma.

The invention further provides a method of making the emulsion compositions of the invention comprising:
  combining tetrahydrocannabinol (THC), an oil, a surfactant, and a first portion of water to form a premix;
  homogenizing the premix to form a homogenized premix;
  adding a second portion of water after the homogenization step to form a bulk sample; and
  filtering the bulk sample over a membrane to afford the emulsion composition.

In other embodiments, the emulsion compositions of the invention are prepared by:
  combining tetrahydrocannabinol (THC), an oil, surfactant, and a first portion of water to form a premix;
  homogenizing the premix at a speed of about 3000 rpm to about 5000 rpm for a time period of about 2 min to about 20 min to form a homogenized premix;
  adjusting the pH of the homogenized premix solution to about 6.5 to about 7.5 to form a neutralized premix;
  adding a second portion of water to the neutralized premix to q.s. at 100% to form a bulk sample; and
  filtering the bulk sample over a membrane having a maximum pore size of about 200 nm to afford the emulsion composition.

The invention further provides a kit comprising a therapeutically effective amount of the emulsion composition of the invention, and instructions for administering the composition to a patient having an ophthalmic condition (such as, neuropathic pain, glaucoma, age-related macular degeneration (AMD), ophthalmitis, or conjunctivitis). The kit can further comprise one or more additional medicaments useful for treating or preventing an ophthalmic condition (such as, glaucoma).

DETAILED DESCRIPTION

Figure 1A:
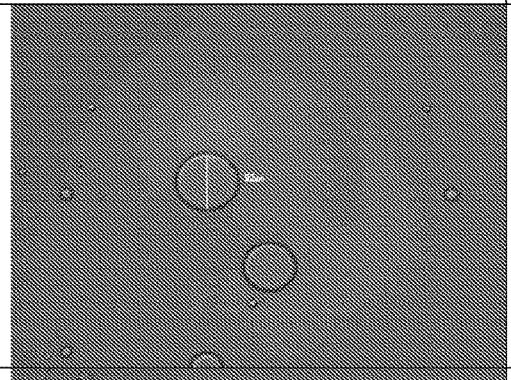
FIG. 1 shows representative microscopy images of the samples described in Example 1 at various time periods after homogenization. Images obtained before (0 min) and 5 min after homogenization are shown in FIG. 1(A).
FIG. 1(B) shows images obtained 10 min and 15 min after homogenization.

As described herein, the present inventor has discovered, after extensive investigation, emulsion formulations particularly well suited for topical administration of cannabinoids for ophthalmic use. The emulsion formulations are stable, well tolerated, and capable of delivering therapeutically effective amounts of cannabinoid to target sites, including sites on the surface of and/or within the eye. Surprisingly, the emulsion formulations are physically, chemically and/or microbiologically stable and exhibit intense and long-lasting intraocular pressure (IOP)-depressant effects.

In one aspect, the present invention provides, inter alia, an emulsion composition comprising:
an active pharmaceutical ingredient, such as a cannabinoid compound (e.g., tetrahydrocannabinol or a derivative thereof);
an oil (e.g., an organic solvent or a vegetable oil);
a surfactant; and
water,
wherein the emulsion composition comprises an oil phase component comprising a plurality of oil droplets, dispersed with an aqueous phase component, the emulsion remains stable after being stored at a condition selected from, for example, at least two years at about −18° C.; at least three months at about 4° C.; and at least one month at about 23° C. (or room temperature), such that there is an absence of visible phase separation between the oil phase component and the aqueous phase component after such storage condition.

As used herein, the term "emulsion" relates to a colloidal dispersion of two or more liquid immiscible phases (or substantially immiscible phases) in the form of droplets. One of the liquid phases is normally a dispersed phase and another one is a continuous phase, wherein the dispersed phase is dispersed in the continuous phase as a plurality of droplets. The emulsion can be in a form of a macro-emulsion, a micro-emulsion or a nano-emulsion based on the size of the droplets. The emulsion is an oil-in-water (o/w) emulsion if the continuous phase is an aqueous solution or a water-in-oil (w/o)-type if the continuous phase is an oil. Other examples of emulsions include oil-in-water-in-oil (o/w/o) emulsions, which comprise oil droplets contained within aqueous droplets dispersed in a continuous oil phase.

In some embodiments, the emulsion comprises at least about 50% (w/w) water and at least one organic solvent. The organic solvents used in the emulsion compositions preferably encompass solvents which are immiscible or at least substantially immiscible with water (sometimes referred to "oils"). The term "oil" preferably encompasses any nonpolar chemical substance that is in liquid form at ambient temperature and atmospheric pressure and is both hydrophobic and lipophilic. The oil may be of animal, plant, or synthetic origin. In some embodiments, the oil is a vegetable oil. Non-limiting examples of suitable vegetable oils include sesame oil, castor oil, soybean oil, olive oil, cotton seed oil, and peanut oil, or a combination thereof. In certain embodiments, the oil in the emulsion composition can be any pharmaceutically acceptable oil.

In some embodiments, the vegetable oil is sesame oil, or castor oil, or a combination thereof.

In some embodiments, the vegetable oil is sesame oil.

The ratio (w/w) of the oil (e.g., a vegetable oil) to water in the emulsion composition is typically in the range of about 1:5 to about 1:1000, or about 1:20 to about 1:100, or about 1:10, 1:30, 1:50, 1:70, or about 1:100.

In some embodiments, the ratio (w/w) of the oil to water in the composition is in the range of about 1:10 to about 1:1000.

In some embodiments, the ratio (w/w) of the oil to water in the composition is in the range of about 1:20 to about 1:100.

In some embodiments, the emulsions comprise about 1.0% or about, 1.2%, about 1.4%, about 1.6%, about 1.8% or about 2.0% (w/w) of oil.

In some embodiments, the emulsion compositions comprise about 0.1% (w/w) to about 20.0% (w/w), or about 1.5% (w/w) to about 5.0% (w/w) of oil, or about 0.2%, 0.4%, 0.6%, 0.8%, 1.0%, 2.0% of oil.

In some embodiments, the emulsion composition comprises about 1.5% (w/w) of oil.

In some embodiments, the emulsion composition comprises about 1.95% (w/w) of oil.

In some embodiments, the emulsion composition comprises about 2.0% (w/w) of oil.

In some embodiments, the oil phase is dispersed as droplets in a continuous aqueous phase, where at least about 50%, 60%, 70% 80% or about 90% of the oil droplets in the emulsion have a diameter of less than about 500 nm, or less than about 300 nm or less than about 200 nm. In some embodiments, the range of droplet size in the composition is about 1 nm to about 300 nm, or about 30 nm to about 300 nm, or about 50 to about 200 nm.

The term "cannabinoid" or "cannabinoid derivative" relates to any cannabinoid compound(s) isolated from the *Cannabis sativa* plant, or a synthetically generated compound that interacts with a cannabinoid receptor, or is a cannabinoid mimetic and/or derivative, including tetrahydrocannabinol (THC), cannabidiol (CBD), cannabinol (CBN), and dodeca-E,4E,8Z,10E/Z-tetraenoic-acid-isobutylamides, cannabigerol (CBG), cannabichromene, cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethylether (CBGM) and their pharmaceutically acceptable salts thereof.

In some embodiments, the active pharmaceutical ingredient in the composition is tetrahydrocannabinol (THC) (or dronabinol; trade name Marinol). THC exists in many isomeric forms, including (+)-trans-$\Delta^8$-tetrahydrocannabinol, (−)-trans-$\Delta^8$-tetrahydrocannabinol, (+)-trans-$\Delta^9$-tetrahydrocannabinol, and (−)-trans-$\Delta^9$-tetrahydrocannabinol. Structures of THC positional and stereoisomers are shown in Scheme 1.

Scheme 1

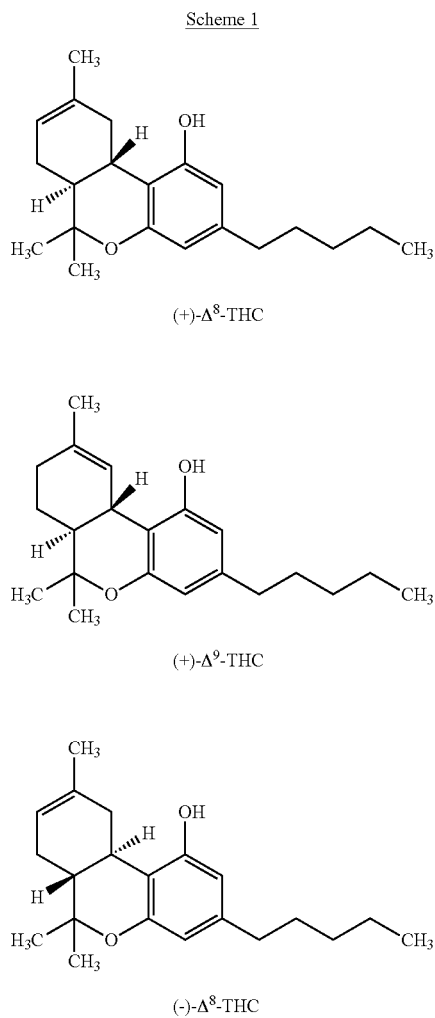

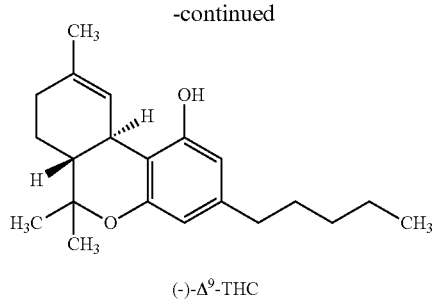

(−) trans-$\Delta^9$-THC is the major natural constituent of *Cannabis sativa*. $\Delta^9$-THC and $\Delta^8$-THC have essentially identical pharmacological profiles and their solubility are essentially identical. Although $\Delta^8$-THC is more stable, which does not undergo oxidation to cannabinol and has a much longer shelf life than $\Delta^9$-THC, it is less potent in most pharmacological tests (see, e.g., *Ophthalmic Res.* (1992) 24: 142-149). Thus, there is a need for stabilized formulations comprising $\Delta^9$-THC and other active THC compounds and derivatives.

In some embodiments, the THC employed in the invention is (−)-trans-$\Delta^9$-tetrahydrocannabinol.

In some embodiments, the THC employed in the invention is (−)-trans-$\Delta^8$-tetrahydrocannabinol.

THC may be present in the compositions of the present invention at about 0.005% (w/w) to about 1.0% (w/w), or about 0.005% (w/w) to about 0.05% (w/w), or about 0.005% (w/w) to about 0.015% (w/w), or about 0.015% (w/w) to about 0.05% (w/w), or at about 0.05% (w/w) to about 0.5% (w/w), or about 0.01%, 0.05%, 0.1%, 0.2%, 0.3%, 0.4% 0.5%, 0.6%, 0.7%, 0.8%, 0.9%, or about 1.0% (w/w).

In certain embodiments, the emulsion composition of the invention comprises about 0.005% (w/w) THC.

In another embodiment, the emulsion composition of the invention comprises about 0.015% (w/w) THC.

In certain embodiments, the emulsion composition of the invention comprises about 0.05% (w/w) THC.

In certain embodiments, the emulsion composition of the invention comprises about 0.5% (w/w) THC.

In certain embodiments, THC (e.g., (−)-trans-$\Delta^9$-tetrahydrocannabinol) or its pharmaceutically acceptable salt thereof is the only cannabinoid compound present in the emulsion composition, that is, the emulsion composition is substantially free of other cannabinoid compounds and/or THC degradation products.

In some embodiments, the emulsion composition is substantially free of certain cannabinoid compounds, e.g., CBD and/or CBG.

In some embodiments, the emulsion composition is substantially free of $\Delta^8$-THC.

In some embodiments, THC or pharmaceutically acceptable salt thereof is combined with other active pharmaceutical ingredients in the composition. The other active pharmaceutical ingredients include, for example, active pharmaceutical ingredients generally considered as suitable for ophthalmologic use (e.g., beta blockers (timolol) and prostaglandins (e.g., latanoprost).

A surfactant may be incorporated in the composition, including nonionic, anionic, cationic, amphoteric and zwitterionic surfactants. Exemplary surfactants include, but are not limited to, Tween®80 (polyoxyethylene (20) sorbitan monooleate); Tween®20 (polyoxyethylene (20) sorbitan monolaurate); Tyloxapol (4-(1,1,3,3-Tetramethylbutyl)phenol polymer with formaldehyde and oxirane); Span®80 (Sorbitane monooleate); Kollipher®HS 15 (polyoxyethylated 12-hydroxystearic acid); polyoxyl 35 castor oil; polyoxyl 40 hydrogenated castor oil; and polyoxyl 40 sterate, or a combination thereof.

In some embodiments, the surfactant is Tween®80 (Polyoxyethylene (20) sorbitan monooleate) or tyloxapol.

In some embodiments, the surfactant is Tween 80 (Polyoxyethylene (20) sorbitan monooleate).

The surfactant may be present in the emulsion, e.g., at 0.5% (w/w) to about 5% (w/w), or about 0.6%, 0.7%, 0.8%, 0.9%, 1.0% 1.2%, 1.4%, 1.6%, 1.8%, 2.0%, 2.1%, 2.2%, 2.3%, 2.4%, 2.5%, 2.6%, 2.7%, 2.8%, 2.9%, 3.0%, 3.5%, 4.0%, 5.0%, 7.0% 10.0%, or about 20.0% (w/w) surfactant.

In some embodiments, the emulsion comprises about 0.5% (w/w) to about 2% (w/w) surfactant.

The emulsion compositions may further comprise a co-solvent. Exemplary co-solvents include one or more of glycerin, propylene glycol, polyethylene alcohol, ethanol, propylene glycol esters, polyethylene glycol esters and mixtures thereof. In certain embodiments, the co-solvent is between about 1% to about 10% (w/w), or about 1% to about 3% (w/w), or about 2.5% w/w of the total weight of the composition. In some embodiments, the co-solvent is a polyol compound. In some embodiments, the co-solvent is glycerin.

The emulsion composition may further comprise an antioxidant. The term "antioxidant" is intended to mean any agent that inhibits oxidation and thus is used to prevent the deterioration of preparations by oxidation due to the presence of oxygen free radicals or free metals in the composition. Suitable antioxidant agents include, for example, Butylated Hydroxyanisole (BHA), Vitamin E, Fumaric Acid, Ascorbyl Palmitate, Butylated Hydroxytoluene (BHT), Monothioglycerol, Propyl Gallate, Sulfur Dioxide, Sodium Thiosulfate, Sodium Sulfite, Ascorbic Acid, Erythorbic Acid, Potassium Metabisulfite, Malic Acid, Sodium Metabisulfite, and Sodium Formaldehyde Sulfoxylate, or a combination thereof.

In some embodiments, the antioxidant used in the emulsion composition of the invention is BHA or BHT, or a combination thereof. The concentration of antioxidant in the emulsion composition may be in the range of about 0.001% (w/w) to about 0.5% (w/w), or about 0.01%, 0.02%, 0.03%, 0.04%, 0.05%, 0.06%, 0.07%, 0.08%, 0.09%, 0.1%, 0.2%, 0.3%, 0.4% or about 0.5%. In some embodiments, the composition comprises about 0.03% (w/w) antioxidant (e.g., BHT and/or BHA). In some embodiments, the composition comprises about 0.03% (w/w) BHT and about 0.03% (w/w) BHA.

A pH adjusting agent may be optionally incorporated in the emulsion composition of the invention. The pH adjusting agent may include, for example, lactic acid, citric acid, phosphoric acid, acetic acid, sodium hydroxide, potassium hydroxide, sodium carbonate, or sodium hydrogen carbonate. The pH adjusting agent is sodium hydroxide in some embodiments. The pH adjusting agent may be present in sufficient quantity to afford a pH level of about neutral or a pH of about 6.5 to about 7.5 or about 6.8 to about 7.2.

Without being bound by any theory of the invention, it is believed that the specific combination of components and method steps described herein impart unexpected physical, chemical, and/or microbiological stability to the emulsion compositions of the invention. "Physically stable" emulsions are those in which, for example, there is no visible phase separation between the oil phase component and the aqueous phase component under appropriate storage conditions, e.g., for at least 1, 2, 3, 4, 5, 6, 9, 12, 15, 18, or 24 months. In certain embodiments, the emulsion composition remains stable after being stored at a condition of at least two years at about −18° C.; at least three months at about 4° C.; or at least one month at about 23° C., such that there is an absence of visible phase separation between the oil phase component and the aqueous phase component after such storage condition. In some embodiments, physically stable emulsions are those in which the particle size distribution of the oil droplet remains essentially constant after exposure to the storage condition (e.g., at least about 90% of the oil droplets in the emulsion are less than about 200 nm in diameter).

"Chemically stable" emulsions are emulsions in which the concentration of the active pharmaceutical ingredient (e.g., THC) does not change by more than about 20% under appropriate storage conditions for at least about two weeks or about one month. In some embodiments, the concentration the cannabinoid (e.g., THC) does not change by more than about 5%, 10%, 15% or 20% under appropriate storage conditions for at least 1, 2, 3, 4, 5, 6, 9, 12, 15, 18, or 24 months.

In some embodiments, the THC remains chemically stable in the emulsion such that at least about 90% (w/w) of the original amount of THC included in the emulsion remains in undegraded form after being stored, e.g., for least two years at about −18° C.; at least three months at about 4° C.; or at least one month at about 23° C.

In some embodiments, the THC remains chemically stable in the emulsion such that at least about 95% (w/w) of the original amount of THC included in the emulsion remains in undegraded form after being stored, e.g., for least two years at about −18° C.; at least three months at about 4° C.; or at least one month at about 23° C.

In some embodiments, the emulsion compositions do not require the use of conventional preservative agents and/or excipients having antimicrobial properties to maintain microbiological stability of the compositions. In some embodiments, the emulsion compositions are substantially free of preservative agents. In some embodiments, the emulsion compositions are substantially free of antimicrobial preservative agents (e.g., benzalkonium chloride; thimerosal; chlorobutanol; methyl paraben; propyl paraben; phenylethyl alcohol; EDTA; and sorbic acid).

In addition to advantageous physical, chemical and microbiological stability provided by the emulsion compositions, it has also been surprisingly discovered that the emulsions are highly suitable for topical administration to the eye of an animal (e.g., a human). The compositions are well tolerated in animal studies and no irritation effects upon topical application have been detected.

The invention further provides, in some embodiments, an emulsion composition comprising:
a tetrahydrocannabinol (THC), or a derivative thereof;
an oil;
a surfactant; and
water,
wherein the emulsion composition comprises an oil phase component comprising a plurality of oil droplets dispersed with an aqueous phase component, wherein the osmolarity of the emulsion composition is substantially similar to human tear fluid osmolarity.

As used herein, the term "osmolarity" refers to the concentration of osmotically active solutes in solution. In some embodiments, the emulsion compositions exhibit an osmolarity which is substantially similar to human tear fluid osmolarity. In some embodiments, the osmolarity of the emulsion compositions is about 300 mOsm/L to about 340 mOsm/L.

In some embodiments, the emulsion compositions are characterized in terms of their osmolality. The term "osmolality" refers to the concentration of osmotically active solutes per kg of solvent. Physiologically-acceptable osmolality is osmolality in accord with the normal functioning of a living organism. Thus, for the purposes of the present invention, the osmolality of the emulsion is substantially similar to human tear fluid osmolality. In some embodiments, the emulsion compositions have an osmolality of about 250 mOsm/kg to about 330 mOsm/kg. In some embodiments, the osmolality of the emulsion compositions is about 290 mOsm/kg to about 315 mOsm/kg.

The invention further provides, in some embodiments, emulsion compositions comprising:
    (−)-trans-$\Delta^9$-tetrahydrocannabinol;
    an oil selected from sesame oil, or castor oil, or a combination thereof;
    a surfactant selected from the group consisting of Tween 80 (polyoxyethylene (20) sorbitan monooleate); Tween® 20 (polyoxyethylene (20) sorbitan monolaurate); Tyloxapol (4-(1,1,3,3-Tetramethylbutyl)phenol polymer with formaldehyde and oxirane); Span 80 (Sorbitane monooleate); Kollipher®HS 15 (polyoxyethylated 12-hydroxystearic acid); polyoxyl 35 castor oil; polyoxyl 40 hydrogenated castor oil; and polyoxyl 40 sterate, or a combination thereof; and water, wherein the ratio (w/w) of oil to water in the composition is in the range of about 1:20 to about 1:100, the emulsion comprises an oil phase component comprising a plurality of oil droplets dispersed with an aqueous phase component, wherein at least about 90% of the oil droplets in the emulsion are less than about 200 nm in diameter. It is understood that the diameter of the oil droplets in the emulsion can span the range of about 30 nm to about 300 nm, or about 1 nm to about 500 nm.

The invention further provides, in some embodiments, emulsion compositions comprising:
    about 0.005% (w/w) to about 0.5% (w/w) of (−)-trans-$\Delta^9$-tetrahydrocannabinol or a pharmaceutically acceptable salt thereof;
    about 1.5% (w/w) to about 2.0% (w/w) of an oil (e.g., sesame oil);
    about 0.5% (w/w) to about 2% (w/w) of a surfactant, e.g., Tween 80 (polyoxyethylene (20) sorbitan monooleate);
    about 2.5% (w/w) of a co-solvent, e.g., glycerin;
    about 0.03% (w/w) of an antioxidant (such as BHT) and/or 0.03% (w/w) of another antioxidant (e.g., BHA); and water,
wherein the ratio (w/w) of oil to water in the composition is in the range of about 1:20 to about 1:100, the emulsion comprises an oil phase component comprising a plurality of oil droplets dispersed with an aqueous phase component, wherein at least about 90% of the oil droplets in the emulsion are less than about 200 nm in diameter, wherein the emulsion remains stable after being stored at a condition selected from the group consisting of: at least two years at about −18° C.; at least three months at about 4° C.; and at least one month at about 23° C., such that there is an absence of visible phase separation between the oil phase component and the aqueous phase component after such storage condition, the (−)-trans-$\Delta^9$-tetrahydrocannabinol or pharmaceutically acceptable salt thereof remains chemically stabile in the composition such that at lease about 90% (w/w) of the initial (−)-trans-$\Delta^9$-tetrahydrocannabinol content in the emulsion composition is present after exposure of the emulsion composition to the storage condition.

Another embodiment of the invention involves a method of making the emulsion compositions of the invention. The emulsion compositions can be prepared, for example, by:
    combining tetrahydrocannabinol (THC), an oil, a surfactant, and a first portion of water to form a premix;
    homogenizing the premix to form a homogenized premix;
    adding a second portion of water after the homogenization step to form a bulk sample; and
    filtering the bulk sample over a membrane to afford the emulsion composition.

It is understood that tetrahydrocannabinol (THC) employed in the methods of the invention includes both tetrahydrocannabinol (THC) in free form and in pharmaceutically acceptable salt form.

In certain embodiments of the invention, the emulsion composition can be prepared by:
    combining tetrahydrocannabinol (THC), an oil, a surfactant, and a first portion of water to form a premix;
    homogenizing the premix at a speed of about 3000 rpm to about 5000 rpm for a time period of about 2 min to about 20 min to form a homogenized premix;
    adjusting the pH of the homogenized premix solution to about 6.5 to about 7.5 to form a neutralized premix;
    adding a second portion of water to the neutralized premix to q.s. at 100% to form a bulk sample; and
    filtering the bulk sample over a membrane having a maximum pore size of about 200 nm to afford the emulsion composition In some embodiments, the homogenization of the premix occurs at a speed of about 5000 rpm for about 2 min.

In some embodiments, the homogenization of the premix occurs at a speed of about 5000 rpm for about 20 min.

In some embodiments, the ratio (w/w) of oil to water in the premix is in the range of about 1:10 to about 1:1000, or about 1:20 to about 1:100. In some embodiments, the amount of oil in the premix is about 1.5% (w/w) to about 5.0% (w/w).

After the homogenization step, an additional (e.g., second) portion of water may be added to form a diluted or bulk sample. The bulk sample can be filtered over a membrane to yield an emulsion composition having oil droplets of a desired size. Suitable membranes include polymer membranes having, for example, a maximum pore size of about 200 nm to about 500 nm (or about 200 nm, 250 nm, 300 nm, 350 nm, 400 nm or about 450 nm). In some embodiments, the membrane comprises a polymer material selected from polyvinylidene fluoride (PVDF), polytetrafluoroethylene (PTFE), and Poly(ether sulfone) (PES).

Another aspect of the invention pertains to methods of providing ocular neuroprotection in a subject (e.g., a human patient in need of neuroprotection) by administering to the eye of the subject a therapeutically effective amount or dose of the emulsion composition of the invention. Neuroprotection refers to the preservation of neural tissue (such as the optic nerve), and/or regeneration of the ocular nerve, and can typically be measured by a reduction of death and/or degeneration of neurons in connection with a neuropathological condition (e.g., neurological injury or disease). The neuropathic condition can include such diseases and/or disorders as blinding eye diseases, including such as, macular degeneration, retinitis pigmentosa, and glaucoma. Neuropathic conditions, such as neuropathic pain, may also be treated.

The invention also includes methods of treating an ophthalmic condition in a subject by administering to the eye of the subject a therapeutically effective amount of the emulsion composition of the invention. Examples of ophthalmic conditions include glaucoma, age-related macular degeneration (AMD), ophthalmitis, and conjunctivitis. In one embodiment, the ophthalmic condition is glaucoma.

Other examples of ophthalmic conditions include diseases of the immune system (e.g., inflammatory diseases) such as, dry eye disease, posterior uveitis, retinitis, uveoretinitis, proliferative vitreoretinopathy, anterior uveitis, episcleritis, scleritis, ocular neuropathic pain, and ocular inflammation caused by a non-infectious condition. In some cases, the ocular neuropathic pain can arise from dry eye, trauma, a corneal abrasion, a corneal burn, a corneal transplant, an autoimmune disease or an allergen.

Without being bound by any theory of the invention it was discovered by the inventors that the emulsion compositions of the invention exhibit a dual IOP-lowering effect as well as neuroprotective and anti-inflammatory potential. The emulsion compositions provide a decrease in intraocular pressure for a period of at least about 1 hour (or longer, e.g., at least about 2-6 hours, or at least about 4 hours or at least about 5-12 hours) after administering the emulsion composition to the eye. In some embodiments, the emulsion compositions provide a decrease in intraocular pressure for a period of at least about 20 or 24 hours. The compositions have also been found to increase the aqueous outflow in the eye of the subject.

As used herein, "topical administration" refers to localized administering to a surface of a tissue, for example, an eye, particularly to any exterior aspect of the eye normally accessible between the eyelids. Topical administration to the eye can normally be achieved by way of eye drops, ointments or sprays. In some embodiments, the emulsion composition is in the form of an eye drop solution. For example, the emulsion composition may be presented in a rigid and/or squeeze-type bottle equipped with fitted cap constructed to serve as a dropper. A human subject may receive between 1 to 10 drops a day (e.g., 8 drops a day) and may repeat application of the dosage, e.g., twice a day. The eye drops may be dispensed as e.g., 12 mL capacity per bottle, or 20 mL capacity per bottle. The emulsion compositions may also be administered by via a carrier vehicle such as liquid drops, liquid wash, gel, ointment, and spray, or a combination thereof. The topical administration may further occur by way of infusing the emulsion composition via a device such as a pump-catheter system, a continuous or selective release device, a contact lens, or a combination thereof. The compositions may also be administered in injectable form, e.g., such that the emulsion is injected behind the eye and/or where the administration involves intravitreal injection.

The term "subject," as used herein, refers to a mammal, such as a human, domestic animal, such as a feline or canine subject, farm animal (e.g., bovine, equine, caprine, ovine, and porcine subject), wild animal, or a research animal (e.g., mouse, rat, rabbit, goat, sheep, pig, dog, and cat, avian species, such as chicken, turkey, and songbird). In some embodiments, the subject is a human subject.

In some embodiments, the emulsion compositions are administered once a day. In other embodiments, the administering occurs more than once a day, e.g., 2 times, 3 times, 4 times, 5 times, 6 times, 7 times, 8 times, 9 times, or 10 times a day. In one embodiment, the administering is 2 times a day.

Also provided herein are kits for treating or preventing an ophthalmic condition in a subject. In a certain embodiment, the ophthalmic condition is glaucoma. A kit can include any of the emulsion formulations described herein. The kit can include a therapeutically effective amount of the emulsion composition of the invention and may further include instructional material for administering the composition to a patient having an ophthalmic condition (such as neuropathic pain, glaucoma, age-related macular degeneration (AMID), ophthalmitis, or conjunctivitis). The instructional material can include a publication, a diagram, or any other medium of expression that can be used to communicate the usefulness of the composition and its administration. The instructional material of the kit may be attached to a container that contains the emulsion composition of the invention or may otherwise be provided together with a container that contains the composition. Alternatively, the instructional material may be provided separately, e.g., by electronic transmission, for example by means of a computer, such as by electronic mail, or download from a web site. The kit can further comprise at least one additional agent, e.g., such as an additional medicament useful for treating or preventing an ophthalmic condition.

The invention are described in greater detail by way of specific examples. The following examples are offered for illustrative purposes and are not intended to limit the invention in any manner. Those of skill in the art will readily recognize a variety of noncritical parameters which can be changed or modified to yield essentially the same results.

EXAMPLES

Reagents and solvents used below can be obtained from commercial sources such as Sigma-Aldrich.

In Examples 1-12, surfactants and processes were screened for making sesame oil-in-water emulsions by homogenization. Emulsion physical attributes and stability were also explored.

Example 1: Feasibility to Prepare an Emulsion of Sesame Oil in Water in the Presence of a Surfactant by Homogenization In this example, feasibility to prepare an emulsion of sesame oil in water in the presence of a surfactant by homogenization was explored.

Model surfactant formulations comprising 7% polyoxyl 40 stearate (EF3) and 0.3% Tyloxapol (EF4) were prepared. The surfactant concentrations used in the model formulations were chosen to span the range of suitable dosage concentrations for ophthalmic use. Surfactants having similar hydrophile-lipophile balance (HLB) values were selected: the HLB of polyoxyl 40 stearate is 16.7; the HLB value of Tyloxapol is 12.9.

Surfactant and sesame oil were added to 80% batch quantity of water for injection (WFI) and mixed for about 30 minutes using a magnetic stir plate to form the EF3 and EF4 formulations (Table 1).

TABLE 1

| EF3 and EF4 Formulations | | |
|---|---|---|
| Reagent, % (w/w) | EF3 | EF4 |
| Surfactant | Polyoxyl 40 stearate, 7% | Tyloxapol, 0.3% |
| Sesame oil | 2% | 2% |
| Water | Added to 100% | Added to 100% |

Figure 1B:
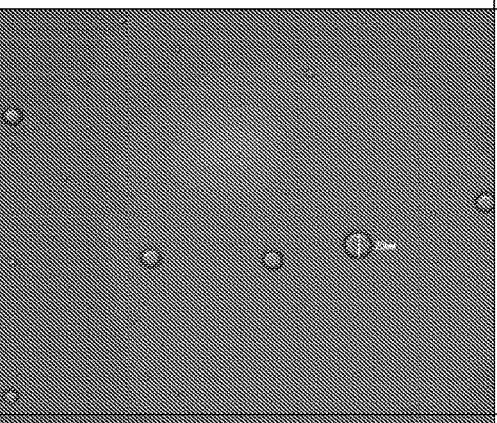

The formulations were brought to 100% wt with additional water and homogenized at 3000 rpm. Samples were collected before the homogenization step and at 5 minute intervals during the homogenization and observed by microscopic imaging at 400×. The homogenization step was terminated at such time after no change was observed in droplet size. Microscopic images (400×) of the EF3 and EF4 formulations at over a 15 min homogenization period are shown in FIG. 1. Images before (0 min) and at 5 min after homogenization are shown in FIG. 1(A). FIG. 1(B) shows images of the compositions at 10 min and 15 min after homogenization.

During homogenization, both EF3 and EF4 samples displayed an initial decrease in droplet size. EF3 showed a slight increase in droplet size at the 10 min to 15 min interval, whereas EF4 showed no change during that period. The largest droplets in EF3 were 20-30 after 15 min of homogenization. The largest droplets in the EF4 sample were around 15 Since no substantial changes in droplet size were observed during the 10-15 min homogenization period, notwithstanding the disparity in surfactant concentrations used in the model formulations, 15 min was identified an optimal homogenization time period.

Example 2: Effect of Surfactant on an Emulsion of Sesame Oil in Water Suitable for Ophthalmic Use In this example, optimal pH and osmolarity ranges for the compositions were evaluated.

Model formulations comprising 7% Polyoxyl 40 Stearate (PE3) and 0.3% Tyloxapol (PE4) were prepared. Surfactant and sesame oil (1.5%) were added to 80% batch quantity of WFI and mixed using a magnetic stir plate. Once the mixtures appeared homogeneous, the samples were diluted up to the desired volume and pH and osmolarity of the solutions were measured. 1N NaOH was used to adjust the pH to 6.8-7.0. NaCl was used to adjust osmolarity of the samples to 270-310 mOsm/L. The results are shown below in Table 2.

TABLE 2

Optimization of pH and Osmolarity During Homogenization

|  | Adjustments | 7% Polyoxyl 40 Stearate placebo (PE3) | 0.3% Tyloxapol placebo (PE4) |
|---|---|---|---|
| pH adjustment | Initial pH | 4.8 | 5.9 |
|  | NaOH added (mM) | 0.55 | <0.1 |
|  | pH after adjustment | 7.0 | 6.9 |
| Osmolarity adjustment | Initial osmolarity (mOsm/L) | 24 | 1 |
|  | NaCl added (% w/w) | 0.75 | 0.85 |
|  | Osmolarity after adjustment (mOsm/L) | 304 | 292 |
| After homogenization | Final pH | 6.8 | 6.9 |
|  | Final osmolarity (mOsm/L) | 302 | 290 |

The amount of NaOH needed to adjust pH was very small and did not substantially contribute to the osmolarity in either the PE3 or PE4 formulations. In the PE4 sample, neither 1.5% sesame oil nor 0.3% Tyloxapol contributed significantly to osmolarity. 7% Polyoxyl 40 Stearate was found to contribute about 23 mOsm/L of osmolarity.

In this experiment, the effect of glycerin on the osmolarity of the formulations was also tested. In formulations lacking glycerin, neither sesame oil nor surfactant was found to substantially alter the osmolarity at reagent amounts up to 1.5% sesame oil and/or 2% surfactant. Thus, it was determined that 0.85% NaCl can be used to formulate such formulations to maintain a suitable osmolarity range. Administration of 2.25% glycerin contributes an osmolarity of about 250 mOsm/L. Thus, it was determined that 0.06% NaCl is useful for formulations containing glycerin to achieve osmolarity of 270 mOsm/L.

Example 3: Sesame Oil in Water Emulsion Preparations with Surfactants of Various HLB's In this example, emulsion formulations PE1-PE10 were prepared as shown in Table 3. These samples were prepared using the method described in Example 1 (homogenized for 15 min at 3000 rpm).

TABLE 3

Emulsion Formulations Formulation Designation

| Reagent | PE1 | PE2 | PE3 | PE4 | PE5 | PE6 | PE7 | PE8 | PE9 | PE10 |
|---|---|---|---|---|---|---|---|---|---|---|
| Polyoxyl 35 castor oil (12.7) | 2.0% | — | — | — | — | 2.0% | — | — | — | — |
| Polyoxyl 40 hydrogenated Castor Oil (14.1) | — | 2.0% | — | — | — | — | 2.0% | — | — | — |
| Polyoxyl 40 stearate (16.7) | — | — | 2.0% | — | — | — | — | 2.0% | — | — |
| Tyloxapol (12.9) | — | — | — | 2.0% | — | — | — | — | 2.0% | — |
| Tween 80 (15) | — | — | — | — | 2.0% | — | — | — | — | 2.0% |
| Sesame oil | 1.5% | 1.5% | 1.5% | 1.5% | 1.5% | 1.5% | 1.5% | 1.5% | 1.5% | 1.5% |
| Glycerine | — | — | — | — | — | 2.25% | 2.25% | 2.25% | 2.25% | 2.25% |

TABLE 3-continued

| | Emulsion Formulations Formulation Designation | | | | | | | | | |
|---|---|---|---|---|---|---|---|---|---|---|
| Reagent | PE1 | PE2 | PE3 | PE4 | PE5 | PE6 | PE7 | PE8 | PE9 | PE10 |
| NaCl | 0.85% | 0.85% | 0.85% | 0.85% | 0.85% | — | — | — | — | — |
| NaOH (for pH adjustment) | q.s. | q.s. | q.s. | q.s. | q.s. | q.s. | q.s. | q.s. | q.s. | q.s. |
| WFI | q.s. | q.s. | q.s. | q.s. | q.s. | q.s. | q.s. | q.s. | q.s. | q.s. |

Example 4: Baseline Oil Vehicle Preparations

In this example, hydrophobic vehicle formulations PH1 and PH2 were prepared as shown in Table 4.

TABLE 4

| Hydrophobic Vehicle Formulations | | |
|---|---|---|
| Reagent | PH1 | PH2 |
| Sesame Oil | 100% | 97.75% |
| Glycerin (co-solvent) | 0% | 2.25% |
| WFI | 0 | 0 |

Example 5: Micro-Emulsion Preparation with a Surfactant

In this example, a micro-emulsion formulation was prepared, as shown below in Table 5. The homogenization method was used according to the procedure set forth in Example 1.

TABLE 5

| Micro-Emulsion Formulation | |
|---|---|
| Reagent | PF1 |
| Kollipher HS 15 (surfactant) | 29.5% |
| WFI | q.s. |

Example 6: Screening of Example 3 Formulations at Various Process Conditions for Emulsion Stability and Particle Size In this example, the physical stability of Samples PE1-PE5 was tested. These samples were prepared using the components and amounts described in Example 3 (homogenized for 15 min at 3000 rpm). Small oil droplets were observed at the surface of the emulsions after homogenization under these conditions. Further, additional oil appeared on the surface 24 hours after formulation. Formulations having varied HLB values were therefore investigated to identify advantageous HLB ranges well suited for combination with sesame oil. Observation of physical appearance for each formulation subjected to four different homogenization conditions (designated Group 1, Group 2, Group 3 and Group 4) over a 3-day period is shown below is Table 6. Particle Size Distribution (PSD) measured using Dynamic Scattering Light is given in Table 7. As shown in Table 7, PSD was measured on Day 3 for Groups 1, 2, and 3, and on Day 2 for Group 4.

In the homogenization experiment (see Table 6), all the emulsions showed a decrease of opacity in 3 days, upon visual inspection. All of the Day 1 samples appeared less opaque than the corresponding samples on Day 0. The Day 2 samples, in turn, appeared less opaque than the corresponding Day 3 samples. All the formulations appeared to have experienced phase separation except PE 4 in Group 2 and Group 3, indicating: (1) Tyloxapol may have advantageous properties; and (2) increasing homogenization speed could improve physical stability of the emulsions. Comparison between Groups 2 and 3 showed that increasing surfactant concentration from 2% to 7.5% did not significantly improve physical stability. Samples in Group 4 (formulations TS6, TS8, TS10, and TS12 having HLB 6, 8, 10, and 12, respectively) showed that HLB values 8 and 10 were more stable than HLB 12; however, homogenization for 20 minutes at 3000 rpm was not sufficient to prevent appearance of oil droplets.

TABLE 6

| Emulsion Formulation Stability Observations. | | | | | | |
|---|---|---|---|---|---|---|
| Sample Information | | | | Appearance | | |
| Group # | Emulsifying Process | Surfactant(s) | Sample Name | Time of Mfg (Day 0) | Day 1 | Day 2 |
| 1 | 15 min@ 3000 rpm | 2% Polyoxyl 35 Castor Oil | PE1 3000 | Non-continuous oil film | Non-continuous oil film on top | Non-continuous oil film on top |
| | | 2% Polyoxyl 40 Hydrogenated Castor Oil | PE2 3000 | Small oil droplets | Small oil droplets on top | Small to medium droplets on top |
| | | 2% Polyoxyl 40 Stearate | PE3 3000 | Small oil droplets | Small oil droplets on top | Large oil droplets on top |
| | | 2% Tyloxapol | PE4 3000 | One large oil droplet | Small oil droplets on top | Small oil droplets on top |

TABLE 6-continued

Emulsion Formulation Stability Observations.

| Group # | Emulsifying Process | Surfactant(s) | Sample Name | Time of Mfg (Day 0) | Day 1 | Day 2 |
|---|---|---|---|---|---|---|
| | | 2% Tween 80 | PE5 3000 | A few small oil droplets | Small oil droplets on top | Small oil droplets on top |
| 2 | 15 min@ 3000 rpm + 20 min @ 5000 rpm | 2% Polyoxyl 35 Castor Oil | PE1 3000 + 5000 | Non-continuous oil film | Non-continuous oil film on top | Non-continuous oil film on top |
| | | 2% Polyoxyl 40 Hydrogenated Castor Oil | PE2 3000 + 5000 | Small oil droplets | Small to medium oil droplets on top | Medium to large oil droplets on top |
| | | 2% Polyoxyl 40 Stearate | PE3 3000 + 5000 | Small oil droplets | Small to medium oil droplets on top | Large oil droplets on top |
| | | 2% Tyloxapol | PE4 3000 + 5000 | No droplets | No droplets on top | No droplets on top |
| | | 2% Tween 80 | PE5 3000 + 5000 | Not droplets | Small oil droplets on top | Small oil droplets on top |
| 3 | 15 min@ 3000 rpm + 20 min @ 5000 rpm, addition of surfactant + 20 min @ 5000 rpm | 7.5% Polyoxyl 35 Castor Oil | PE1 7.5% Surfactant | No droplets | Small oil droplets on top | Small to medium oil droplets on top |
| | | 7.5% Polyoxyl 40 Hydrogenated Castor Oil | PE2 7.5% Surfactant | No droplets | Small oil droplets on top | Small to medium oil droplets on top |
| | | 7.5% Polyoxyl 40 Stearate | PE3 7.5% Surfactant | No droplets | Large oil droplets on top | Large oil droplets on top |
| | | 7.5% Tyloxapol | PE4 7.5% Surfactant | No droplets | No droplets on top | No droplets on top |
| | | 7.5% Tween 80, | PE5 7.5% Surfactant | No droplets | Small oil droplets on top | Small oil droplets on top |
| 4 | 15 min@ 3000 rpm | 0.34% Tween 80 + 1.66% Span 80, 15 min@, 3000 rpm | TS6 3000 | No droplets | Medium to large droplets on top | Medium to large droplets on top |
| | | 0.70% Tween 80 + 1.30% Span 80, 15 min@ 3000 rpm | TS8 3000 | No droplets | Small to medium droplets on top | Small to medium droplets on top |
| | | 1.08% Tween 80 + 0.90% Span 80, 15 min@ 3000 rpm | TS10 3000 | No droplets | Small to medium droplets on top | Small to medium droplets on top |
| | | 1.72% Tween 80 + 0.28% Span 80, 15 min@ 3000 rpm | TS12 3000 | No droplets | Medium droplets on top | Medium droplets on top |

TABLE 7

Particle Size Distribution

| Group # | Emulsifying Process | Surfactant(s) | Sample Name | D10 (μm) | D50 (μm) | D90 (μm) |
|---|---|---|---|---|---|---|
| 1 | 15 min@ 3000 rpm | 2% Polyoxyl 35 Castor Oil | PE1 3000 | 14.91 | 51.35 | 74.37 |
| | | 2% Polyoxyl 40 Hydrogenated Castor Oil | PE2 3000 | 9.04 | 44.22 | 70.85 |
| | | 2% Polyoxyl 40 Stearate | PE3 3000 | 13.3 | 50.36 | 73.36 |
| | | 2% Tyloxapol | PE4 3000 | 11.39 | 46.74 | 71.89 |
| | | 2% Tween 80 | PE5 3000 | 8.33 | 42.2 | 69.68 |
| 2 | 15 min@ 3000 rpm + 20 min @ 5000 rpm | 2% Polyoxyl 35 Castor Oil | PE1 3000 + 5000 | 1.46 | 13.17 | 31.06 |
| | | 2% Polyoxyl 40 Hydrogenated Castor Oil | PE2 3000 + 5000 | 1.99 | 19.54 | 35.99 |
| | | 2% Polyoxyl 40 Stearate | PE3 3000 + 5000 | 2.05 | 19.76 | 36.79 |
| | | 2% Tyloxapol | PE4 3000 + 5000 | 1.9 | 19.26 | 37.61 |
| | | 2% Tween 80 | PE5 3000 + 5000 | 1.84 | 18.46 | 36.64 |
| 3 | 15 min@ 3000 rpm + 20 min @ 5000 rpm + addition of surfactant + 20 min @ 5000 rpm | 7.5% Polyoxyl 35 Castor Oil | PE1 7.5% Surfactant | 1.62 | 14.41 | 29.17 |
| | | 7.5% Polyoxyl 40 Hydrogenated Castor Oil | PE2 7.5% Surfactant | 1.74 | 15.42 | 28.26 |
| | | 7.5% Polyoxyl 40 Stearate | PE3 7.5% Surfactant | 1.67 | 15.88 | 31.76 |
| | | 7.5% Tyloxapol | PE4 7.5% Surfactant | 2.05 | 19.26 | 34.06 |
| | | 7.5% Tween 80, | PE5 7.5% Surfactant | 2.07 | 19.57 | 33.59 |
| 4 | 15 min@ 3000 rpm | 0.34% Tween 80 + 1.66% Span 80, 15 min@, 3000 rpm | TS6 3000 | 1.24 | 4.37 | 43.06 |

TABLE 7-continued

Particle Size Distribution

| Group # | Emulsifying Process | Surfactant(s) | Sample Name | D10 (μm) | D50 (μm) | D90 (μm) |
|---|---|---|---|---|---|---|
| | | 0.70% Tween 80 + 1.30% Span 80, 15 min@, 3000 rpm | TS8 3000 | 1.28 | 6.15 | 33.3 |
| | | 1.08% Tween 80 + 0.90% Span 80, 15 min@ 3000 rpm | TS10 3000 | 1.28 | 4.58 | 44.27 |
| | | 1.72% Tween 80 + 0.28% Span 80, 15 min@, 3000 rpm | TS12 3000 | 1.95 | 28.62 | 62.67 |

It was discovered that increasing homogenization speed and time decreased the particle size in the emulsions (see Table 7, comparison of Groups 1 and 2). Moreover, increasing surfactant concentration from 2% to 7.5% did not significantly alter particle size (Groups 2 and 3). There appears to be an HLB threshold between 10 and 12 that significantly alters particle size distribution. However, as shown in Table 6, HLB value does not necessarily correlate to physical stability.

Example 7: Evaluation of Emulsification Process Sequence with PE4 Formulation for Stability In this example, emulsion formulations were prepared by first homogenizing an oil phase with only a small portion of an aqueous phase in a first step followed by a step of diluting up with aqueous solution to 100% batch quantity. PE4 (Tyloxapol) was used in this study. Specifically, Tyloxapol (2 g) was added to X g of 0.85% NaCl (X=20, 50, 80, and 96.5) and the resulting solution was mixed until Tyloxapol was completely dissolved. Sesame oil (1.5 g) was added and the resulting solution was mixed for 15-30 min. The mixture was then homogenized for 20 min at 5000 rpm resulting in a homogenized premix. NaCl solution (0.85%) was added to the homogenized mixture at q.s. (quantity sufficient) to arrive at 100 g (except for the sample with X=96.5). The particle size distribution results from this experiment are shown in Table 8.

appeared to be physically stable for 7 days with no oil droplets forming on the surface and PSD profile staying unchanged. In this experiment, PSD was measured after the formulation was prepared when the q.s. step was performed. PSD was measured without shaking/mixing in the foam.

Example 8: Evaluation with Emulsification Process Sequence of PE5 Formulation for Stability In this example, emulsion formulations were prepared by first homogenizing an oil phase with only a small portion of an aqueous phase in a first step followed by a step of diluting up with aqueous solution to 100% batch quantity. PE5 (Tween 80) was used in this study. Tween 80 was added to 0.85% NaCl and the resulting solution was mixed until Tween 80 was completely dissolved. Sesame oil was added, and the resulting solution was mixed for 15-30 min. The mixture was then homogenized for 20 min at 5000 rpm. NaCl solution (0.85%) was added to the homogenized mixture at q.s. to arrive at 100 g (except for the sample with X=96.5). The varied amount of sesame oil and aqueous NaCl used in the PE5 formulations in this experiment are shown in Table 9.

TABLE 8

Particle Size Distribution Measurements for PE4 Samples.

| Sample | PE4-20 | | | PE4-50 | | | PE4-80 | | | PE4-96.5 | | |
|---|---|---|---|---|---|---|---|---|---|---|---|---|
| oil:water ratio during homogenization | 1.5:20 | | | 1.5:50 | | | 1.5:80 | | | 1.5:96.5 | | |
| Total volume of homogenized premix (mL) | 23.5 | | | 53.5 | | | 83.5 | | | 100 | | |
| PSD (μm) | D10 | D50 | D90 | D10 | D50 | D90 | D10 | D50 | D90 | D10 | D50 | D90 |
| Day 0 | 1.89 | 15.16 | 28.10 | 2.45 | 22.36 | 38.59 | 2.79 | 25.13 | 43.29 | 2.80 | 25.73 | 44.95 |
| Day 1 | 1.95 | 15.48 | 28.05 | 2.43 | 22.34 | 38.32 | 2.67 | 25.10 | 43.36 | 3.02 | 26.92 | 45.89 |
| Day 3 | 2.02 | 16.41 | 29.09 | Not Tested | | | 2.99 | 26.34 | 44.35 | 3.00 | 26.91 | 45.5 |
| Day 7 | 2.05 | 16.70 | 29.50 | 2.46 | 22.66 | 38.87 | 3.08 | 27.00 | 44.93 | 3.27 | 27.96 | 47.19 |

No oil droplets were observed in any of the above formulations throughout a 7-day observation period. All formulations showed a decrease of clarity during this period with a thin layer of white foam on top, similar to the formulations in the aforementioned studies. Upon shaking, the white foam mixed with the clear solution at the bottom of the samples and formed a cloudy mixture. The PSD showed an increasing trend when the oil:water ratio decreased from 1.5:20 to 1.5:96.5. The formulations

TABLE 9

Formulation of PE5 with Sesame Oil and Aqueous NaCl

| Content | PE5-20 | PE5-50 | PE5-80 | PE5-96.5 |
|---|---|---|---|---|
| Tween 20% w/w | 4.55 | 2.00 | 1.28 | 1.07 |
| 0.85% NaCl, % w/w | 45.53 | 50.00 | 51.26 | 51.63 |

TABLE 9-continued

Formulation of PE5 with Sesame Oil and Aqueous NaCl

| Content | PE5-20 | PE5-50 | PE5-80 | PE5-96.5 |
|---|---|---|---|---|
| Sesame oil, % w/w | 3.41 | 1.50 | 0.96 | 0.80 |
| Oil:water ratio | 1.5:20 | 1.5:50 | 1.5:80 | 1.5:96.5 |

The particle size distribution results are shown in Table 10. The data was measured after q.s.'ing with NaCl.

TABLE 10

Particle Size Distribution Measurements for PE5 Samples

| Sample | PE5-20 | | | PE5-50 | | | PE5-80 | | | PE5-96.5 | | |
|---|---|---|---|---|---|---|---|---|---|---|---|---|
| oil:water ratio during homogenization | 1.5:20 | | | 1.5:50 | | | 1.5:80 | | | 1.5:96.5 | | |
| Total volume homogenized (mL) | 53.5 | | | 53.5 | | | 53.5 | | | 53.5 | | |
| PSD (μm) | D10 | D50 | D90 | D10 | D50 | D90 | D10 | D50 | D90 | D10 | D50 | D90 |
| Day 0 | 2.55 | 22.04 | 37.94 | 2.28 | 22.37 | 38.87 | 2.17 | 22.10 | 39.70 | 2.15 | 21.66 | 36.93 |
| Day 3 | 2.62 | 22.19 | 38.35 | 2.35 | 22.65 | 38.70 | 2.26 | 22.88 | 40.16 | 2.25 | 22.13 | 37.34 |
| Day 6 | 2.55 | 21.78 | 37.73 | 2.27 | 22.31 | 39.00 | 2.22 | 22.82 | 39.75 | 2.21 | 21.94 | 36.93 |

Very small oil droplets were noted on Day 0 in all 4 formulations. The oil droplets slightly grew in size over a 6-day observation period. All formulations showed a decrease of clarity during this period with a thin layer of white foam on top of the solution. Upon shaking, the white foam mixed with the clear solution at the bottom of the samples and formed a cloudy mixture. The PSD of all 4 samples were similar, indicating the energy input was a determining factor in particle size.

Example 9: Evaluation of Homogenization Speed and Time on PE1-5 Samples

In this example, the effect of high homogenization speed and increased homogenization time on the PE1-5 samples was investigated. Formulations PE 1-5 were prepared as set forth in Example 3 (each sample was prepared at 100 g total). The formulations were homogenized at 8000 rpm for 20 min. If oil droplets were observed on the surface, the homogenization period was prolonged further. The PE4 was homogenized at 5000 rpm for 20 minutes because reduced speed was found to form an emulsion in this sample with no oil droplets on the surface.

A large amount of foam was generated in formulations homogenized at 8000 rpm. An oil surface layer was observed in samples PE1, PE2, PE3, and PE5 after a total of 90 minutes of homogenization at 8000 rpm. The oil appeared to be a non-continuous film on the surface of PE1. Small to medium-sized droplets were observed on the surface of PE2 and PE3. PE5 had a few very small oil droplets on the surface. PE4 showed no oil on top after homogenization at 5000 rpm for 20 minutes.

PE4 and PE5 samples were exposed to 5° C. and 40° C. temperature conditions to test for physical stability. The stability results over the 7-day period are shown in Table 11 below. In Table 11, "phase separation" is manifested as oil droplets on the surface of the emulsion. The term "forced phase separation" refers to samples treated with centrifugation at 4000 rpm for increments of 2 min.

TABLE 11

Physical Stability of PE4 and PE5

| | Sample | Phase separation | Forced phase separation | pH | PSD (μm) | | |
|---|---|---|---|---|---|---|---|
| | | | | | D10 | D50 | D90 |
| PE4 | Day 0 | N | 4 min | 6.5 | 2.63 | 26.04 | 45.33 |
| | Day 7, 5° C. | Y | — | 6.5 | 1.64 | 12.52 | 34.99 |
| | Day 7, 40° C. | N | 2 min | 6.1 | 2.21 | 22.69 | 42.94 |
| PE5 | Day 0 | Y | — | 6.9 | 1.10 | 2.37 | 6.97 |
| | Day 7, 5° C. | Y | — | 6.9 | 1.08 | 2.28 | 5.51 |
| | Day 7, 40° C. | Y | — | 6.5 | 1.08 | 2.29 | 5.63 |

PE1, PE2, and PE3 did not form a homogeneous emulsion even after a very aggressive process of homogenization at 8000 rpm for 90 minutes, indicating that the surfactants used in those samples may not be most preferred surfactants for the emulsion formulation.

PE4 initially did not show any oil droplets on the surface, but oil droplets were observed after storage at 5° C. for 7 days, indicating the physical stability of the formulation may become somewhat compromised at low temperature. No phase separation was observed in the sample stored at 40° C. Phase separation at 5° C. may result from decreased Brownian movement at that temperature which does not occur at 40° C.

Although PE5 showed some oil droplets on the surface, the droplets were very small in size and there were very few of them, identifying Tween 80 as a particularly preferred surfactant. PE5 exhibited high stability over the 7-day testing period, only showing a slight degree of phase separation at the beginning. PE5 stayed stable during storage at both 5° C. and 40° C. such that no substantial change in PSD or appearance was observed. Both PE4 and PE5 stored at 40° C. exhibited a decrease in pH decreased after 7 days. This is believed to result from dissolved carbon dioxide.

Example 10: Evaluation of Homogenization Speed and Time on Emulsion Stability

In this example, conditions of high homogenization speed and long homogenization duration was tested on emulsions having HLB 6, 8, 10, and 12 (formulations TS6, TS8, TS10, and TS12; from Example 6). Specifically, 100 g formulations of TS6, TS8, TS10, and TS12 using Tween 80 and Span 80 were prepared as set forth in Example 6. The samples were homogenized at 8000 rpm for 20 min. For samples showing visual oil droplets after the 20 min cycle were homogenized for longer time periods.

A large amount of foam was generated during homogenization. Small to medium oil droplets were observed in all four formulations. When this emulsifying process was applied to samples PE1-5 and TS6-12, all formulations except PE4 and PE5 formed heterogeneous emulsion samples. This suggests that the species of surfactant pays a significant role in the emulsion formulation, not the HLB value of the surfactant.

Examples 9-10 showed PE4 and PE5 are promising.

Example 11: Examination of Castor Oil for Emulsion Preparations

In this example, castor oil was investigated as a vehicle for oil incorporation in the emulsion compositions. Two formulations with Tween 80 (PE11) and Tyloxapol (PE12) were prepared using an emulsifying process of 5000 rpm homogenization for 20 min. The formulations prepared in this experiment are shown in Table 12. The formulations were stored at room temperature and at 5° C., and 40° C. to observe the physical stability.

TABLE 12

Formulation Composition of PE11 and PE12.

| Function | Formulation PE11 | PE12 |
|---|---|---|
| Surfactant | Tween 80, 2% | Tyloxapol, 2% |
| Oil | Castor oil, 1.5% | Castor oil, 1.5% |
| Co-solvent/osmolarity agent | Glycerin, 2.25% | Glycerin, 2.25% |
| pH agent (target 6.8-7.2) | NaOH, q.s. | NaOH, q.s. |

During the experiment, PE11 initially showed small oil droplets on the surface, similar to PE10 (Tween 80 with sesame oil); PE12 showed no droplets on the surface, similar to PE9 (Tyloxapol with sesame oil). Table 13 shows formulation observations after one week of storage at three different conditions.

TABLE 13

Physical stability of PE11 and PE12 (1W).

| Storage condition | Formulation/observation @ 1W | |
|---|---|---|
| | PE11 (Tween 80 with castor oil) | PE12 (Tyloxapol with castor oil) |
| RT | Small oil droplets on top | No oil droplets |
| 5° C. | Large oil droplets on top | Large oil droplets on top |
| 40° C. | Small-medium oil droplets on top | No oil droplets |

The similarity between the sesame oil formulations and the castor oil formulations indicates that castor oil provides a similar degree of oil incorporation in the emulsion.

The behavior of the castor oil formulations under various storage conditions is similar to sesame oil formulations: Tween 80 showed better physical stability than Tyloxapol under 5° C., while Tyloxapol showed better physical stability at room temperature and 40° C.

Example 12: Examination of Process Temperature Effects

In this example, it was tested whether high formulation temperature improves the emulsification. Sample PE13 was prepared using the same composition as PE10 (2% Tween 80, 2.25% glycerin and 1.5% sesame oil) but was heated to 70° C. The formulation was homogenized at 5000 rpm for 20 minutes. Initially, PE13 demonstrated slightly better incorporation of oil and fewer oil droplets of smaller size at the surface after homogenization. However, large oil droplets were observed on the surface after storage at 5° C. for 1 week, deviating from the behavior of PE10 which showed little change after storage at the same condition for 1 week. Storage of PE13 and PE10 at room temperature and 40° C. did not cause any change in the formulation in either sample. The physical stability observed for PE13 indicates that heating during formulation did not improve physical stability.

In Examples 13-24, effects of Pemulen (as a co-surfactant) on prototype formulation, PE14 (with placebo) were explored, which led to AE14 (active). Also process parameters of micro-fluidization process, packaging effects were studied together with emulsion attributes and stability.

Example 13: Examination of Pemulen (as a Co-Surfactant) on Formulation Stability In this example, Pemulen TR-2 was added to formulations with Tween 80 and Tyloxapol to explore Pemulen TR-2 as a co-surfactant. The formulations were not homogenized, as the manufacturer suggests high shear emulsifying process may compromise the formation of a gel structure that provides physical stability for the emulsions. The formulations and initial observations are given in Table 14.

TABLE 14

Composition and Observations of Pemulen TR-2 Formulations

| Function | Formulation/ initial observation | | | |
|---|---|---|---|---|
| | PE14 | PE15 | PE16 | PE17 |
| Surfactant | Tween 80, 2% | Tyloxapol, 2% | Tween 80, 2% | Tyloxapol, 2% |
| Co-surfactant | Pemulen TR-2, 0.05% | Pemulen TR-2, 0.05% | Pemulen TR-2, 0.05% | Pemulen TR-2, 0.05% |
| Oil | Sesame oil, 1.5% | Sesame oil, 1.5% | Castor oil, 1.5% | Castor oil, 1.5% |
| Co-solvent/ osmolarity agent | Glycerin, 2.25% | Glycerin, 2.25% | Glycerin, 2.25% | Glycerin, 2.25% |
| pH agent (target 6.8-7.2) | NaOH (used for pH adjustment) | NaOH (used for pH adjustment). | NaOH (used for pH adjustment) | NaOH (used for pH adjustment) |
| Initial observation | Viscous, whitish liquid with visible oil droplets evenly distributed within; a few very small oil droplets on top. | Viscous, whitish liquid with visible oil droplets evenly distributed within; no oil droplets on top. | Viscous, whitish liquid with visible oil droplets evenly distributed within; large oil droplets on top. | Viscous, whitish liquid with visible oil droplets evenly distributed within; a few small oil droplets on top. |

Pemulen TR-2 significantly increased the viscosity of the emulsions. In certain respects, this was considered an advantage for achieving physical stability since higher viscosity results in slower movement of oil droplets towards the surface. Without homogenization, the formulations with Pemulen TR-2 demonstrated similar oil incorporation results to those with homogenization but no Pemulen TR-2, indicating Pemulen is effective in improving emulsification.

The PE14 premix samples were combined with Pemulen dispersion (to form 100% batch quantity) and mixed with a stir bar. The resulting compositions were adjusted to pH 6.8-7.2.

The formulation stability test results for PE14, PE14B and PE14C are shown in Table 15. In the table, "phase separation" refers to oil droplets observed on the surface of the emulsion. Forced phase separation was carried out by centrifugation at 4000 rpm for 10 min increments.

TABLE 15

Physical Stability of PE14B and PE14C.

| | Sample | Phase separation | Forced phase separation | pH | PSD (μm) | | |
|---|---|---|---|---|---|---|---|
| | | | | | D10 | D50 | D90 |
| PE14B | Day 0 | N | N (total 60 min) | 7.0 | 2.82 | 24.07 | 39.70 |
| | Day 7, 5° C. | N | N (total 60 min) | 6.9 | 2.83 | 24.18 | 40.15 |
| | Day 7, RT | N | N (total 60 min) | 6.9 | 2.98 | 24.70 | 40.48 |
| | Day 7, 40° C. | N | N (total 60 min) | 6.8 | 2.70 | 23.80 | 39.81 |
| PE14C | Day 0 | N | N (total 60 min) | 6.7 | 6.47 | 12.66 | 21.15 |
| | Day 7, 5° C. | N | N (total 60 min) | 6.8 | 7.02 | 13.65 | 23.11 |
| | Day 7, RT | N | N (total 60 min) | 6.3 | 6.80 | 13.73 | 23.79 |
| | Day 7, 40° C. | N | N (total 60 min) | 6.6 | 6.65 | 13.15 | 22.39 |

Similar to formulations without Pemulen, Tyloxapol showed advantageous oil incorporation.

Example 14: Prototype Formulations Prepared with Microfluidics to Monitor Stability with and without Pemulen Two formulations (PE14B and PE14C) based on PE14 were used as promising prototype samples.

The PE14 premix was prepared by combining Tween 80, sesame oil, glycerin and water (water was added at ~60% batch quantity). The premix was mixed with a stir bar.

PE14: no additional process step was performed;

PE14B: sample was homogenized at 5000 rpm for 20 min (60 g premix)

PE14C: sample treated on the M110P microfluidizer (5 passes) by Microfluidics

The Pemulen dispersion was prepared by combining Pemulen TR-2 with water (water was added at ~40% batch quantity). The dispersion was mixed with a stir bar.

The 7 day physical stability data showed that both formulations PE14B and PE14C were stable at the three conditions for 7 days. This was an improvement compared to formulations without Pemulen TR-2, as well as PE14 which contained Pemulen TR-2 but did not have a premix processed by use of a homogenizer or microfluidizer. The PSD of PE14C did not conform to the PSD measured at Microfluidics (D99 less than 0.2 μm). This is most likely because the particles in the premix were outside the measuring range of the Synpatec DSL Particle Analyzer. As demonstrated in the premix filtration experiments, discussed below, the PSD of the microfluidized premix could not be measured. The PSD reported for PE14C in the table above was possibly the PSD of the dispersed Pemulen particles.

Example 15: Effects of Filtration

In this example, parameters for sterile filtration of the prototype PE14B and PE14C premix samples were examined. Specifically, PE14B and PE14C premix samples processed using two different emulsifying methods were studied for their filterability. The filter type used in this experiment was a 0.2 μm PVDF syringe filter with 25 mm diameter.

In the PE14B premix (60 g premix homogenized @ 5000 rpm for 20 min), very high resistance was observed during filtration and a large force was required to compress the syringe. The initial filtrate appeared clear, indicating retention of oil droplets in the filter. A small amount of the premix was forced through the filter after the initial clear filtrate came through. This fraction appeared cloudy. After about 2 mL of sample was filtered, no remaining premix was able to pass through the filter. The particle size distribution of the premix before and after filtration is shown in Table 16. The particle size distribution shift confirmed the retention of oil droplets in the filter.

Use of homogenization for the emulsifying process may require an alternative sterilization method.

Example 16: Stability of the Prototype Formulations of Example 14

In this example, the physical stability of PE14B and PE14C was tested.

PE14B and PE14C were tested for stability under three temperature conditions: room temperature, 5° C. and 40° C. over a three-week period. The results of the stability tests are shown in Table 17. In the table, "phase separation" refers to oil droplets observed on the surface of the emulsion. Forced phase separation was carried out by centrifugation at 4000 rpm for 10 min increments.

TABLE 17

Physical Stability of PE14B and PE14C (3 W)

| Sample | | Phase separation | Forced phase separation | pH | PSD (μm) D10 | D50 | D90 |
|---|---|---|---|---|---|---|---|
| PE14B | Day 0 | N | N (total 60 min) | 7.0 | 2.82 | 24.07 | 39.70 |
| 5° C. | Day 7 | N | N (total 60 min) | 6.9 | 2.83 | 24.18 | 40.15 |
|  | Day 14 | N | N (total 60 min) | 6.9 | 2.53 | 23.04 | 39.31 |
|  | Day 21 | N | N (total 60 min) | 6.9 | 3.01 | 24.64 | 40.68 |
| RT | Day 7 | N | N (total 60 min) | 6.9 | 2.98 | 24.70 | 40.48 |
|  | Day 14 | N | N (total 60 min) | 6.9 | 2.59 | 23.53 | 39.96 |
|  | Day 21 | N | N (total 60 min) | 6.8 | 2.96 | 24.20 | 39.96 |
| 40° C. | Day 7 | N | N (total 60 min) | 6.8 | 2.70 | 23.80 | 39.81 |
|  | Day 14 | N | N (total 60 min) | 6.9 | 2.71 | 23.76 | 40.31 |
|  | Day 21 | N | N (total 60 min) | 6.8 | 3.00 | 24.45 | 40.40 |
| PE14C | Day 0 | N | N (total 60 min) | 6.7 | 6.47 | 12.66 | 21.15 |
| 5° C. | Day 7 | N | N (total 60 min) | 6.8 | 7.02 | 13.65 | 23.11 |
|  | Day 14 | N | N (total 60 min) | 6.6 | 6.37 | 12.17 | 20.53 |
|  | Day 21 | N | N (total 60 min) | 6.6 | — | — | — |
| RT | Day 7 | N | N (total 60 min) | 6.3 | 6.80 | 13.73 | 23.79 |
|  | Day 14 | N | N (total 60 min) | 6.7 | 6.38 | 12.27 | 20.69 |
|  | Day 21 | N | N (total 60 min) | 6.8 | — | — | — |
| 40° C. | Day 7 | N | N (total 60 min) | 6.6 | 6.65 | 13.15 | 22.39 |
|  | Day 14 | N | N (total 60 min) | 6.7 | 6.25 | 11.97 | 20.37 |
|  | Day 21 | N | N (total 60 min) | 6.7 | — | — | — |

TABLE 16

Particle size distribution of PE14B.

| Sample | PSD (μm) D10 | D50 | D90 |
|---|---|---|---|
| PE14B, unfiltered | 2.06 | 19.99 | 36.06 |
| PE14B, filtered | 1.39 | 2.31 | 3.54 |

For PE14C premix (5 passes through the microfluidizer), no significant resistance was observed during filtration. PE14C was easily filtered. The particle size distribution of PE14C could not be measured using the Synpatec DLS analyzer as the optical concentration could not reach the required range of 15-25%. Undiluted PE14C had an optical concentration of only about 3%. It is believed that the oil droplets in PE14C were out of the measuring range (0.5-87.5 μm).

The above results indicate that use of a microfluidizer in the manufacturing process allows for effective sterile filtration of the premix. Filtration through 0.2 μm filter of PE14B versus PE14C (five passes of emulsification) showed removal of oil of PE14B.

As shown, both formulations (PE14B and PE14C) demonstrated physical stability over 3 weeks, with no phase separation observed. Moreover, centrifugation at 4000 rpm for 60 minutes could not force phase separation in the formulations. The PSD of PE14B did not change over the three-week period, indicating stability of the emulsion. PSD of PE14C was tested by Microfluidics at the end of stability and compared with PSD of the premix.

Example 17: Process to Make Active Batch with Pemulen

In this example, a formulation process of AE14B active trial batch was carried out. The term "active batch," "active trial batch" or "active formulation" refers to a batch of a testing formulation/composition contains an active pharmaceutical ingredient ("API"), such as dronabinol.

Container #1: The AE14B premix was prepared by adding ~55 g water for injection to container #1 while purging under nitrogen and stirring until 02<5 ppm was achieved. Tween 80 was added with N2 overlay, followed by addition of 1.0 g API (50% w/w dronabinol dissolved in sesame oil), 2.25 g glycerin, and 1.00 g sesame oil.

Container #2: in a separate container, a Pemulen mixture was prepared by adding ~35 g water for injection to container #2 while purging under nitrogen and stirring until 02<5 ppm was achieved. Pemulen (0.05 g) was added with nitrogen overlay. The Pemulen mixture was added to container #1 and the resultant mixture was homogenized with nitrogen overlay, stirred with nitrogen overlay, and then adjusted to pH 6.8-7.2 with q.s. to 100 g with WFI.

The AE14B bulk was filled in 0.5 mL BFS containers following the procedure below:

Twisting open a blow-fill-seal BFS container;
Purging the inside of the BFS container using a needle connected to the end of an argon line;
Filled 0.5 mL AE14B bulk in the container using a syringe;
Purging the inside of the container again with argon;
Immediately sealing the container using a heat sealer.

Five filled BFS containers were tested for pH, assay and impurities. 87.5 g bulk formulation was tested for density, osmolarity, assay, and impurities.

Example 18: Testing Alternative Filters

In this example, an alternative method for filtering the PE14B (60 g premix homogenized @ 5000 rpm for 20 min) was investigated. A 0.2 µm polytetrafluoroethylene (PTFE) (hydrophobic) syringe filter was used to filter PE14B. PE14B required a very large force to compress the syringe plunger, and the first mL or so of filtrate appeared to be clear. After about 3 mL filtrate went through, the operator was no longer able to force additional formulation through the filter.

A 0.2 µm PES (hydrophilic) syringe filter was also used to filter PE14B. The same effects were observed as seen with the PVDF and PTFE filters.

Example 19: Assay and Impurity Profile of an Active Batch

In this example, assay and impurity measurements for the AE14B active trial batch (from Example 17) were collected. The results of these tests are shown in Table 18.

TABLE 18

Assay/impurities Results of AE14B Trial Batch

| Sample | AE14B, Bulk | AE14B, Holopack | API: 50% Dronabinol in Sesame Oil |
|---|---|---|---|
| THC % Area | 94.09 | 93.96 | 99.84 |
| THC Assay (% LC) | 76.10 | 74.89 | 96.63* |
| Impurities | | | |
| Impurity | | % Area | |
| CBD | — | — | — |
| CBN | 0.24 | 0.25 | 0.18 |
| Delta 8 THC | — | — | — |
| RRT 1.16 | 3.08 | 3.10 | — |
| RRT 1.20 | 2.60 | 2.69 | — |
| Total Impurities | 5.9 | 6.0 | 0.2 |

*Calculated using 48.4% based on the certificate of analysis

As shown in Table 18, the THC peak in the formulation is about 94% in total peak area, with about 6% total impurities. The remaining loss of API therefore is likely from the formulation process, e.g., insufficient rinsing.

Example 20: Evaluation of Prototype Formulations with Pemulen and without Pemulen for Stability In this example, the PE14C sample (processed with microfluidizer) was examined. PE14C was processed at using the M110P microfluidizer. PE14C was combined with a Pemulen dispersion in a 60:40 ratio to form a product emulsion. The stability of the resulting product emulsion was tested for stability over a 4 weeks period under at three temperature conditions: 5° C., room temperature, and 40° C. The premix and product from all three conditions were then tested for particle size distribution. The results are shown in Table 19. In the table, "phase separation" refers to oil droplets observed on the surface of the emulsion. Forced phase separation was carried out by centrifugation at 4000 rpm for 10 min increments.

TABLE 19

Physical Stability of PE14C Premix and Product.

| Sample | Phase separation | Forced phase separation | Z-ave (nm) | PDI |
|---|---|---|---|---|
| Premix, initial | N | N | 84.56 | 0.188 |
| Premix, RT, 4 W | N | N | 79.35 | 0.235 |
| Product, 5° C., 4 W | N | N | 85.32 | 0.298 |
| Product, RT, 4 W | N | N | 85.76 | 0.287 |
| Product, 40° C., 4 W | N | N | 86.98 | 0.293 |

As shown in Table 19, the Z-average of the samples did not change significantly in the premix or the product emulsion, indicating a high level of physical stability in both samples. PDI increased slightly for both premix and product. As both the premix and the product showed high stability, it is believed that a microfluidized formulation can provide sufficient physical stability even in the absence of Pemulen.

Example 21: Chemical Stability of an Active Batch in BFS Packaging

In this experiment, the impurity profile of AE14B (batch #2) was tested. High impurities in trial batch #1 indicated degradation or oxidation during trial batch #1. Therefore, pH adjustment and q.s. steps were carried out inside a glove box due to high impurities indicating degradation or oxidation, using the process described below.

Container #1: The AE14B premix was prepared by adding ~55 g water for injection to container #1 while purging under nitrogen and stirring until 02<5 ppm was achieved. Tween 80 (2 g) was added with nitrogen overlay, followed by addition of 1.0 g API (THC), 2.25 g glycerin and 1.0 g sesame oil. The Tween and API were set up under ambient air in open glove box before the components were added to container #1.

Container #2: in a separate container, a Pemulen mixture was prepared by adding ~35 g water for injection to container #2 while purging under nitrogen and stirring until 02<5 ppm was achieved. Pemulen (0.05 g) was added with nitrogen overlay. The Pemulen mixture was added to container #1 and the mixture was homogenized with nitrogen overlay, stirred with nitrogen overlay [please confirm], and then adjusted to pH 6.8-7.2 with q.s. to 100 g with WFI to provide the AE14B product bulk.

The in-process samples were processed according to the following steps:

Homogenization of the AE14B product bulk was carried out after 2 min the API was mixed with the aqueous phase. Under preferred conditions, the sample is processed immediately after mixing the API with the aqueous phase. However, because the API was concentrated in large oil droplets on the surface of the premix, and a sample could not be taken without removing a significant portion of the API, 2 min after the start of homogenization was selected as the approximate homogenization start point under these conditions.

End of homogenization (20 min);
Adjust pH
Carry out q.s. step.

The product was filled in BFS containers under nitrogen purge. Two configurations, BFS alone and BSF in aluminum pouch, were stored in a refrigerator for a week. The BFS containers were packed in aluminum pouches with nitrogen purge and oxygen absorber.

Assay and impurity measurements for AE14B batch #2 were collected. The results of these tests are shown in Table 20.

TABLE 20

AE14B Trial Batch #2 Testing Results

| Sample | After 2 min homogenization | After 20 min homogenization | After pH adjustment | After Q.S. | Individual BFS (Initial) | Individual BFS (1W, 2-8° C.) | BFS in aluminum pouch (1W, 2-8° C.) |
|---|---|---|---|---|---|---|---|
| THC % Area | 95.4 | 95.1 | 95.5 | 95.27 | 95.2 | 95.2 | 95.4 |
| THC Assay (% LC) | — | — | — | 81.1 | 81.4 | 81.5 | 84.1 |
| THC Conc. (% w/w) | 0.74 | 0.75 | 0.48 | 0.41 | 0.41 | 0.41 | 0.42 |
| Impurities | | | | | | | |
| Impurity | | | | %Area | | | |
| CBD | — | — | — | — | — | — | — |
| CBN | 0.19 | 0.19 | — | 0.26 | 0.20 | 0.25 | 0.22 |
| Delta 8 THC | — | — | — | — | — | — | — |
| RRT 1.21 | 0.43 | 0.44 | 0.41 | 0.44 | 0.43 | 0.42 | 0.41 |
| RRT 1.28 | 1.63 | 1.65 | 1.64 | 1.69 | 1.68 | 1.68 | 1.65 |
| RRT 1.36 | 2.36 | 2.31 | 2.45 | 2.44 | 2.45 | 2.43 | 2.35 |
| Total | 4.6 | 4.6 | 4.5 | 4.8 | 4.8 | 4.8 | 4.6 |

In this experiment, the extra rinsing only slightly reduced the API loss (the assay results increased from 75% LC to 81% LC). Impurities only slightly decreased from 6% to 5%. The 2-min homogenization sample already contained 4.6% total impurities and the impurities remained at that level throughout the subsequent process. This indicates the most degradation and/or reaction of API occurred before homogenization.

When Trial Batch #1 was made, some API was dispensed in the same set-up to test for assay and impurities; the API sample only contained 0.2% total impurities. This indicates the weighing process did not significantly increase the impurities; the impurities were generated after weighing and before homogenization, likely during the addition into water.

In order to monitor the replacement of ambient air by argon inside the hood, the humidity inside the hood was monitored. Argon sweep of the hood drove humidity to ~0%. The humidity decreased from 30% to 15% after exhausting a full tank of argon. The impurities did not increase after storage at 2-8° C. for a week in either packaging configuration. This indicates that for short term storage, oxygen permeation through the BFS container is not a significant factor in stability.

Example 22: Chemical Stability Examination of an Active Batch During Process

In this example, AE14B batch #3 was tested. As set forth in Example 21, the Batch #2 sample taken at 2 min homogenization showed high impurities, the impurities staying at the same level during the rest of the process. It is therefore believed that reaction or degradation likely occurs before homogenization and that the API reacted with water or other excipients in the premix due to low pH. Accordingly, in Batch #3, 0.1N NaOH was added before addition of API. The batch process is described below.

Container #1: The AE14B premix was prepared by adding ~55 g water for injection to container #1 while purging under nitrogen and stirring until O2<5 ppm was achieved. Tween 80 (2 g) was added with nitrogen overlay, followed by addition of 1.06 g API, 2.25 g glycerin and 0.94 g sesame oil. The Tween and API were set up under ambient air in open glove box before the components were added to container #1. 3.5 g 0.1N NaOH was added before addition of API to container #1.

Container #2: in a separate container, a Pemulen mixture was prepared by adding ~35 g water for injection to container #2 while purging under nitrogen and stirring until O2<5 ppm was achieved. Pemulen (0.05 g) was added with nitrogen overlay. This was carried out under ambient air on the counter top. The Pemulen mixture was added to container #1 and the mixture was homogenized with nitrogen overlay, stirred with nitrogen overlay with q.s. to 100 g with WFI to provide the AE14B batch #3 product bulk.

Three samples (1 g) were collected during this process. 1 g of API was also sampled:

Sample A: after API addition, before homogenization
Sample B: 2 min homogenization
Sample C: 20 min homogenization
Sample D: after Q.S.

Assay and impurity measurements for the AE14B batch #3 were collected. The results of these tests are shown in Table 21.

TABLE 21

AE14B Trial Batch #3 Testing Results

| Sample | Sample A (before homogenization) | Sample B (after 2 min homogenization) | Sample C (after 20 min homogenization) | Sample D (product after Q.S.) | API Sample |
|---|---|---|---|---|---|
| Conc. % w/w | 0.10 | 0.71 | 0.75 | 0.37 | 38.29 |
| Osmolarity (mOsm/L) | — | — | — | — | 228 |
| pH | 11.84 | — | — | — | 6.60 |

| Impurity | % Area | | | | |
|---|---|---|---|---|---|
| RRT 0.40 | — | — | — | — | — |
| RRT 0.46 | — | 0.17 | 0.16 | 0.19 | — |
| RRT 0.56 | — | — | — | — | — |
| CBD | — | — | 0.10 | — | — |
| RRT 0.70 | — | — | — | — | — |
| RRT 0.81 | — | 0.14 | 0.14 | 0.12 | — |
| CBN | — | 0.22 | 0.21 | 0.22 | 0.18 |
| RRT 0.93 | — | 0.24 | 0.23 | 0.22 | 0.18 |
| RRT 1.18 | 0.34 | — | — | — | — |
| RRT 1.22 | 3.91 | 0.51 | 0.48 | 0.38 | — |
| RRT 1.27 | 8.44 | 1.26 | 1.19 | 1.24 | — |
| RRT 1.35 | 12.48 | 2.03 | 1.95 | 2.05 | — |
| Total | 25.2 | 4.6 | 4.5 | 4.4 | 0.4 |

CBD (cannabidiol) and CBN (cannabinol) were used as internal standards in this experiment. All other impurities are marked by their relative retention time (RRT).

In this example, the analytical method for impurities was modified. As a result, more species of impurities were detected compared to previous active batches. Sample D and the API sample showed lower assay than expected. Impurities in Samples A were fewer than Samples B and C, likely on account that A had lower concentration of API, thus the impurity concentration fell below the detection limit. For the purpose of process evaluation, the impurity species in all four samples was considered substantially the same. The final product (Sample D) contained similar impurities compared to those in Trial Batch #2, indicating that adjusting pH before API addition did not resolve the API degradation/incompatibility issue.

Impurities from RRT 1.18 to RRT 1.35 were much higher in Sample A than the rest of the in-process samples. Because the level of each impurity was calculated as (area of impurity peak)÷(Total area of Dronabinol and impurity peaks), the % Area of each impurity should be proportional to assay when the samples get concentrated or diluted, assuming no degradation. If there was degradation during the process, Sample A should contain fewer impurities than the rest, not more. The most probable explanation of this result is that the impurities were from the excipients, not the API.

Example 23: Examination on Impurity Profile of an Active Batch

In this example, additional experiments were performed on AE14B batch #3. A placebo batch was formulated and tested in order to find out whether the late eluting impurities are from the excipients. Sample D and API were re-tested for assay because results in Table 21 were lower than expected. Testing results are shown in Table 22 (combined with the initial testing results; new samples are shown in Italic).

TABLE 22

AE14B Trial Batch #3 additional testing results

| Sample | Sample A | Sample B | Sample C | Sample D | API Sample | Repeated Sample D | Repeated API Sample | Placebo |
|---|---|---|---|---|---|---|---|---|
| API % w/w | 0.10 | 0.71 | 0.75 | 0.37 | 38.29 | 0.43 | 44.2 | — |
| Assay % LC | 20.10 | 141.77 | 150.28 | 74.92 | 79.12 | 85.23 | 91.29 | 0.00 |
| % Area (THC from Imp) | 74.8 | 95.1 | 95.4 | 95.6 | 99.6 | — | — | 0.00 |
| Osmolarity (mOsm/L) | — | — | — | — | 228 | — | — | 243 |
| pH | 11.84 | — | — | — | 6.60 | — | — | 7.14 |

| Impurity | % Area of Impurities | | | | | | | |
|---|---|---|---|---|---|---|---|---|
| RRT 0.40 | — | — | — | — | — | — | — | — |
| RRT 0.46 | — | 0.17 | 0.16 | 0.19 | <0.1 | — | — | — |
| RRT 0.56 | — | — | — | — | — | — | — | — |
| CBD | — | — | 0.10 | — | — | — | — | — |
| RRT 0.70 | — | — | — | — | — | — | — | — |
| RRT 0.81 | — | 0.14 | 0.14 | 0.12 | — | — | — | — |
| CBN | — | 0.22 | 0.21 | 0.22 | 0.18 | — | — | — |
| RRT 0.93 | — | 0.24 | 0.23 | 0.22 | 0.18 | — | — | — |
| RRT 1.18 | 0.34 | — | — | — | — | — | — | 6.19 |

TABLE 22-continued

AE14B Trial Batch #3 additional testing results

| Sample | Sample A | Sample B | Sample C | Sample D | API Sample | Repeated Sample D | Repeated API Sample | Placebo |
|---|---|---|---|---|---|---|---|---|
| RRT 1.22 | 3.91 | 0.51 | 0.48 | 0.38 | — | — | — | — |
| RRT 1.24 | — | — | — | — | — | — | — | 35.08 |
| RRT 1.27 | 8.44 | 1.26 | 1.19 | 1.24 | — | — | — | — |
| RRT 1.30 | — | — | — | — | — | — | — | 58.74 |
| RRT 1.35 | 12.48 | 2.03 | 1.95 | 2.05 | — | — | — | — |
| Total Impurity | 25.2 | 4.6 | 4.5 | 4.4 | 0.4 | — | — | 100.0 |
| | | | | % w/w of Impurities | | | | |
| RRT 0.40 | — | 0.12 | 0.13 | — | — | — | — | — |
| RRT 0.46 | — | 0.26 | 0.26 | 0.16 | <0.1 | — | — | — |
| RRT 0.56 | — | <0.1 | 0.10 | — | — | — | — | — |
| CBD | — | 0.14 | 0.16 | — | — | — | — | — |
| RRT 0.70 | — | 0.11 | 0.11 | — | — | — | — | — |
| RRT 0.81 | — | 0.22 | 0.22 | 0.10 | — | — | — | — |
| CBN | — | 0.34 | 0.35 | 0.18 | 0.15 | — | — | — |
| RRT 0.93 | — | 0.38 | 0.38 | 0.18 | 0.15 | — | — | — |
| RRT 1.18 * | <0.1 | — | — | — | — | — | — | 0.20 |
| RRT 1.22 | 0.97 | 0.81 | 0.79 | 0.31 | — | — | — | — |
| RRT 1.24 * | — | — | — | — | — | — | — | 1.16 |
| RRT 1.27 | 2.08 | 1.99 | 1.97 | 1.04 | — | — | — | — |
| RRT 1.30 * | — | — | — | — | — | — | — | 1.94 |
| RRT 1.35 | 3.08 | 3.20 | 3.22 | 1.72 | — | — | — | — |
| Total | 6.1 | 7.6 | 7.7 | 3.7 | 0.3 | — | — | 3.3 |

* Different instrument and mobile phases was used in this example; impurity peaks may have shifted.

The impurity profile in this example confirmed that the late eluting impurities (RRT 1.22 and later in the original samples) are from the excipient(s), not degradation products from API. Excluding these impurities, the total impurities in the final formulation is 0.8% area, compared to 0.4% area in the API. The 0.4% increase from API to formulation was likely a result of oxygen exposure during formulation process. Samples A, B and C were taken before final Q.S., therefore the w/w concentration in these samples were higher than Sample D and placebo.

Example 24: Chemical Stability of Active Batch in Glass Vial Compared to BFS Ampoules In this example, an active batch was made using the process described in Example 22. The formulation was packaged in two forms: 1) 2.5 mL fill volume in 5 mL glass vials with argon head space; and 2) 0.5 mL fill volume in 0.5 mL BFS ampoules with argon head space, packed in aluminum pouches with argon purge and oxygen absorber (5 ampoules per pouch). The stability results of these samples are shown in Tables 23 and 24.

TABLE 23

Chemical Stability of AE14B in Glass Vial (up to 2 W)

Product Dronabinol AE14B Formulation in Glass Vial

| | Storage Condition | | | | |
|---|---|---|---|---|---|
| | 5° C. | | | 25° C./60% RH | |
| | Time Point | | | | |
| | Initial | 1 W | 2 W | 1 W | 2 W |
| | Appearance | | | | |
| | No phase separation | No phase separation | No phase separation | No phase separation | No phase separation |
| pH | 6.0 | 6.4 | 6.8 | 6.7 | 6.8 |
| Assay (% LC) | 88.1 | 83.5 | 88.1 | 85.1 | 89.0 |

TABLE 23-continued

Chemical Stability of AE14B in Glass Vial (up to 2 W)

Product Dronabinol AE14B Formulation in Glass Vial

| | Storage Condition | | | | |
|---|---|---|---|---|---|
| | 5° C. | | | 25° C./60% RH | |
| | Time Point | | | | |
| | Initial | 1 W | 2 W | 1 W | 2 W |
| | Appearance | | | | |
| | No phase separation | No phase separation | No phase separation | No phase separation | No phase separation |
| | Impurity (% w/w) | | | | |
| RRT 0.40 | 0.11 | 0.27 | 0.38 | 0.48 | 0.56 |
| RRT 0.46 | 0.22 | 0.21 | 0.23 | 0.24 | 0.27 |
| RRT 0.61 | — | — | — | 0.11 | 0.15 |
| CBD | 0.15 | — | — | — | — |
| RRT 0.70 | 0.08 | — | — | — | — |
| CBN | 0.57 | 0.54 | 0.59 | 0.63 | 0.72 |
| RRT 0.93 | 0.54 | 0.51 | 0.52 | 0.54 | 0.54 |
| Total | 1.7 | 1.5 | 1.7 | 2.0 | 2.2 |
| | Impurity (% Area) | | | | |
| RRT 0.40 | 0.13 | 0.33 | 0.44 | 0.58 | 0.64 |
| RRT 0.46 | 0.26 | 0.26 | 0.27 | 0.29 | 0.31 |
| RRT 0.61 | — | — | — | 0.13 | 0.17 |
| CBD | 0.17 | — | — | — | — |
| RRT 0.70 | 0.09 | — | — | — | — |
| CBN | 0.66 | 0.67 | 0.69 | 0.76 | 0.83 |
| RRT 0.93 | 0.63 | 0.63 | 0.61 | 0.64 | 0.62 |
| Total | 1.9 | 1.9 | 2.0 | 2.4 | 2.6 |

TABLE 24

Chemical Stability of AE14B in BFS Ampoule (up to 2 W)

Product: Dronabinol AE14B Formulation in BFS Ampoule

| | Storage Condition | | | | |
|---|---|---|---|---|---|
| | 5° C. | | | 25° C./60% RH | |
| Time Point | | | | | |
| | Initial | 1 W | 2 W | 1 W | 2 W |
| Appearance | | | | | |
| | No phase separation | No phase separation | No phase separation | No phase separation | No phase separation |
| pH | 5.9 | 6.5 | 6.7 | 6.7 | 6.8 |
| Assay (% LC) | 87.5 | 82.2 | 88.4 | 86.4 | 83.6 |
| Impurity (% w/w) | | | | | |
| RRT 0.40 | 0.11 | 0.26 | 0.37 | 0.39 | 0.53 |
| RRT 0.46 | 0.22 | 0.21 | 0.23 | 0.24 | 0.26 |
| RRT 0.61 | — | — | — | 0.12 | 0.14 |
| CBD | 0.16 | — | — | — | — |
| RRT 0.70 | 0.08 | — | — | — | — |
| CBN | 0.56 | 0.53 | 0.60 | 0.62 | 0.68 |
| RRT 0.93 | 0.52 | 0.51 | 0.53 | 0.52 | 0.51 |
| Total | 1.6 | 1.5 | 1.7 | 1.9 | 2.1 |
| Impurity (% Area) | | | | | |
| RRT 0.40 | 0.12 | 0.33 | 0.43 | 0.47 | 0.64 |
| RRT 0.46 | 0.26 | 0.26 | 0.26 | 0.29 | 0.32 |
| RRT 0.61 | — | — | 0.07 | 0.14 | 0.17 |
| CBD | 0.18 | — | — | — | — |
| RRT 0.70 | — | — | — | — | — |
| CBN | 0.66 | 0.66 | 0.70 | 0.73 | 0.83 |
| RRT 0.93 | 0.61 | 0.63 | 0.61 | 0.61 | 0.62 |
| Total | 1.8 | 1.9 | 2.1 | 2.2 | 2.6 |

In this example, no phase separation was observed in any sample upon visual inspection. A pH increase was observed in both glass and BFS samples. This was believed to result from the pH reading drift during measurement resulting from: 1) the small sample size (less than 2 mL); 2) the micro pH probe used specifically for the small samples; or 3) the formulation itself.

Low assay was observed in the 3 trial batches as well as the stability samples. This is believed to be a result of the analytical method, as the reference standard was measured by volume instead of weight and thus introducing error into the method. 2-week sample of BFS container at 25° C./60% RH showed lower assay than the rest of samples tested at the same time point. Because the impurities were not significantly higher in this sample, indicating the decrease of assay was likely not from degradation, it might be a result of adsorption on the BFS container.

The method used in this example was intended to increase sensitivity. As a result, RRT0.40 and RRT 0.70 were detected in initial samples, while they were not detected in previous batches due to low sensitivity. More impurities were detected in this experiment compared to previous trial batches: CBN and RRT 0.93 were higher compared to Trial Batch #3. This may be because of the prolonged exposure to ambient air during the filling process. CBD was detected in the initial sample but not after 1 week. The reason for this change is not clear but it is possible that CBD degraded; the degradation could also be the reason for the appearance of RRT0.61.

At 5° C., only RRT0.40 showed a growing trend over 2 weeks, while the rest of impurities stay unchanged. At 25° C./60% RH, all impurities but RRT0.93 showed a growing trend over 2 weeks that is more prominent than 5° C. These results indicate the AE14B formulation without anti-oxidant present may not be stable. No impurity profile difference between glass and BFS containers was observed, indicating the BFS resin is compatible with the formulation.

Example 25: Development Method for Particle Size Distribution

In this example, micro-fluidize trial runs using the Malvern Mastersizer 3000 were performed.

Micro-Fluidizer trial runs: PE10C formulation (no Pemulen) (PE10C is PE14C without Pemulen) was processed with the microfluidizer at 10,000 psi, 20,000 psi, and 30,000 psi in batch sizes of 100 g, totaling 5 passes for each batch.

Particle Size Analysis (PSD) method development using the Malvern Mastersizer 3000.

Figure 2:
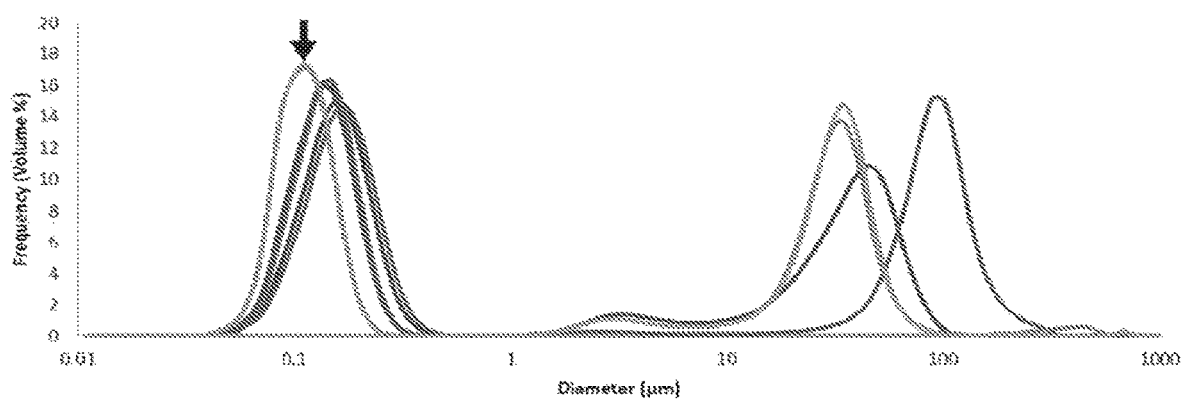
FIG. 2 shows a representative particle size distribution plot of PE14C and premix samples described in Example 25. The plot of the PE14C premix (no Pemulen) sample described in Example 25 is marked with an arrow.

Preliminary results of microfluidized sample PSD compared to samples processed at Microfluidics are shown in FIG. 2. In FIG. 2, the PSD of PE14C and pre-mix (PE14C pre-mix is the same as PE10) was measured at Microfluidics with Horiba (sample was made at Microfluidics). Data as shown is at initial time point at 30,000 psi. The plot marked with an arrow in FIG. 2 refers to the PE14C without Pemulen.

Figure 3:
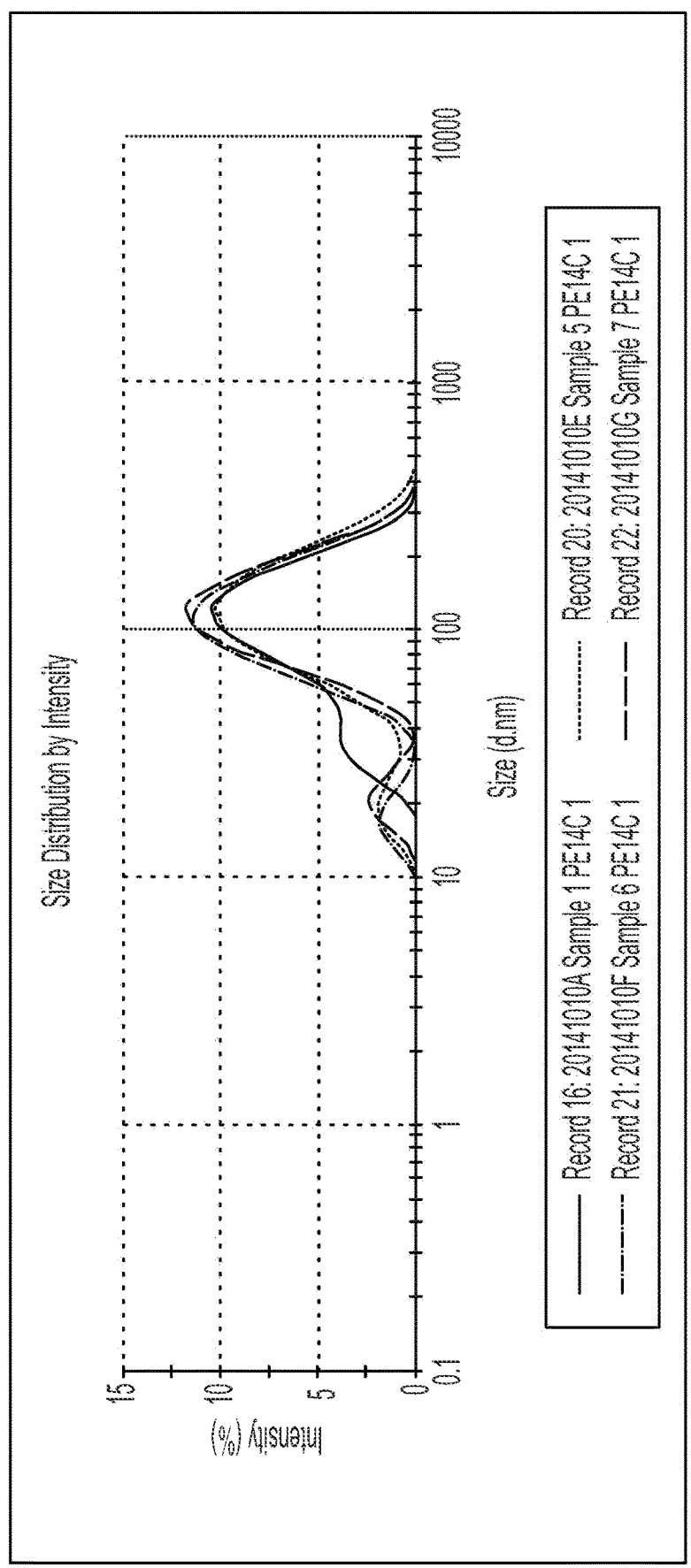
FIG. 3 shows a representative particle size distribution plot of PE14C and premix samples described in Example 25. The plot of the PE14C premix (no Pemulen) sample is marked with an arrow.

FIG. 3 shows PSD of PE14C and premix measured at Microfluidics with Zetasizer (sample was made at Microfluidics) at 30,000 psi at 4 weeks. The results marked with an arrow refer to PE14C without Pemulen.

Figure 4:
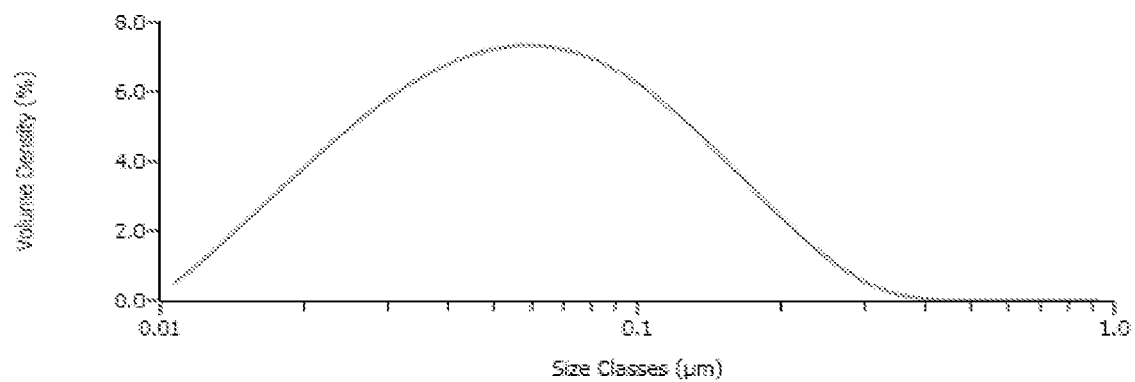
FIG. 4 shows a representative particle size distribution plot of the PE10C sample described in Example 25.

FIG. 4 shows PSD of PE10C measured at Frontage with Mastersizer 3000 (sample made at Microfluidics) at 30,000 psi at 4 months.

Figure 5:
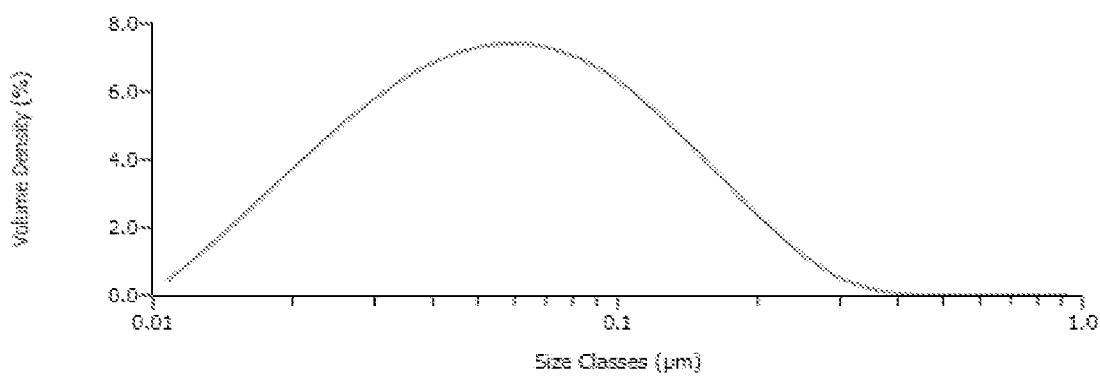
FIG. 5 shows a representative particle size distribution plot of the PE14C sample described in Example 25.

FIG. 5 shows PSD of PE14C measured at Frontage with Mastersizer 3000 (fresh sample made at Frontage) at 30,000 psi at 4 months.

Example 26: Antioxidant Effects on Active Formulation

In this experiment, antioxidants were selected for use in emulsion formulations of the invention. Certain selected antioxidants and their associated IIG (Inactive Ingredient Guide) limits are shown in Table 25.

TABLE 25

Pharmaceutical Anti-Oxidants & IIG Limits

| Antioxidant | [3]Solub. in Water | Route/IIG Limit | | | | | |
|---|---|---|---|---|---|---|---|
| | | Oral | IV | IM | OPH | Nasal | Topical |
| Butylated Hydroxyanisole (BHA) | Insoluble | 0.5 mg | 0.0003% | 0.03% | — | 2% | 1% |

TABLE 25-continued

Pharmaceutical Anti-Oxidants & IIG Limits

| Antioxidant | [3]Solub. in Water | Route/IIG Limit | | | | | |
|---|---|---|---|---|---|---|---|
| | | Oral | IV | IM | OPH | Nasal | Topical |
| Vitamin E | Insoluble | 1.3 mg | — | — | — | — | 0.0001% |
| [2]Fumaric Acid | 0.007 mg/L | 80 mg | — | — | — | — | — |
| Ascorbyl Palmitate | 0.07 mg/L | 12 mg | — | — | — | — | 0.2% |
| Butylated Hydroxytoluene (BHT) | 0.4 mg/L | 0.4 mg | 0.0015% | 0.03% | — | 0.01% | 2% |
| Monothioglycerol | Slightly | — | 1% | 1% | — | — | — |
| [1]Propyl Gallate | 0.35 | 1.4 mg | — | — | — | — | 0.05% |
| Sulfur Dioxide | 8.5 | — | 0.15% | — | — | — | — |
| Sodium Thiosulfate | 20.9 | 20 mg | 0.19% | — | 5% | — | 0.1% |
| Sodium Sulfite | 22 | 0.03% | 0.2% | 0.2% | 0.2% | — | 0.2% |
| [2]Ascorbic Acid | 33 | 20 mg | 62.5% | 1% | — | — | 0.3% |
| [2]Erythorbic Acid | 40 | — | — | — | — | — | — |
| Potassium Metabisulfite | 49.5 | — | 0.1% | 0.1% | — | — | — |
| [2]Malic Acid | 59.2 | 31.5% | — | — | — | — | — |
| Sodium Metabisulfite | Freely | 8 mg | 27.5% | 27.5% | 0.25% | — | 0.2% |
| Sodium Formaldehyde Sulfoxylate | Freely | — | 1.1% | 0.2% | — | — | — |

[1]Synergistic effects with BHT and BHA was reported.
[2]Normally used with BHT and BHA
[3]g/100 mL water unless otherwise specified Example 27: Chemical Stability of Active Batch in Glass Vial Compared to BFS Ampoules In this example, an active batch (AE14B) was made using the process described in Example 22. The formulation was packaged in two forms: 1) 2.5 mL fill volume in 5 mL glass vials with argon head space; and 2) 0.5 mL fill volume in 0.5 mL BFS ampoules with argon head space, packed in aluminum pouches with argon purge and oxygen absorber (5 ampoules per pouch). The stability results of this example are shown in Table 26 and Table 27.

TABLE 26

Chemical Stability of AE14B in Glass Vial (up to 4 W)

Product: Dronabinol AE14B Formulation in Glass Vial

| | Storage Condition | | | | | | |
|---|---|---|---|---|---|---|---|
| | 5° C. | | | | 25° C./60% RH | | |
| | Time Point | | | | | | |
| | Initial | 1 W | 2 W | 4 W | 1 W | 2 W | 4 W |
| Appearance | No phase separation | No phase separation | No phase separation | No phase separation | No phase separation | No phase separation | No phase separation |
| pH | 6.0 | 6.4 | 6.8 | 6.4 | 6.7 | 6.8 | 6.5 |
| Assay (% LC) | 88.1 | 83.5 | 88.1 | 86.4 | 85.1 | 89.0 | 86.9 |
| Impurity (% w/w) | | | | | | | |
| RRT 0.40 | 0.11 | 0.27 | 0.38 | 0.48 | 0.48 | 0.56 | 0.77 |
| RRT 0.46 | 0.22 | 0.21 | 0.23 | 0.24 | 0.24 | 0.27 | 0.32 |
| RRT 0.61 | — | — | — | 0.11 | 0.11 | 0.15 | 0.22 |
| CBD | 0.15 | — | — | — | — | — | — |
| CBN | 0.57 | 0.54 | 0.59 | 0.62 | 0.63 | 0.72 | 0.83 |
| RRT 0.93 | 0.54 | 0.51 | 0.52 | 0.56 | 0.54 | 0.54 | 0.58 |
| Total | 1.6 | 1.5 | 1.7 | 2.0 | 2.0 | 2.2 | 2.7 |
| Impurity (% Area) | | | | | | | |
| RRT 0.40 | 0.13 | 0.33 | 0.44 | 0.56 | 0.58 | 0.64 | 0.89 |
| RRT 0.46 | 0.26 | 0.26 | 0.27 | 0.28 | 0.29 | 0.31 | 0.37 |
| RRT 0.61 | — | — | — | 0.13 | 0.13 | 0.17 | 0.26 |
| CBD | 0.17 | — | — | — | — | — | — |
| CBN | 0.66 | 0.67 | 0.69 | 0.72 | 0.76 | 0.83 | 0.96 |
| RRT 0.93 | 0.63 | 0.63 | 0.61 | 0.65 | 0.64 | 0.62 | 0.66 |
| Total | 1.9 | 1.9 | 2.0 | 2.3 | 2.4 | 2.6 | 3.1 |

* RRT0.70 was removed from the original data report as re-analysis revealed it was noise, not an actual impurity peak.

TABLE 27

Chemical Stability of AE14B in BFS Ampoule (up to 4 W)

Product: Dronabinol AE14B Formulation in BFS Ampoule

| | Storage Condition | | | | | | |
|---|---|---|---|---|---|---|---|
| | 5° C. | | | | 25° C./60% RH | | |
| | Time Point | | | | | | |
| | Initial | 1 W | 2 W | 4 W | 1 W | 2 W | 4 W |
| Appearance | No phase separation | No phase separation | No phase separation | No phase separation | No phase separation | No phase separation | No phase separation |
| pH | 5.9 | 6.5 | 6.7 | 6.6 | 6.7 | 6.8 | 6.6 |
| Assay (% LC) | 87.5 | 82.2 | 88.4 | 81.9 | 86.4 | 83.6 | 76.3 |
| Impurity (% w/w) | | | | | | | |
| RRT 0.40 | 0.11 | 0.26 | 0.37 | 0.47 | 0.39 | 0.53 | 0.70 |
| RRT 0.46 | 0.22 | 0.21 | 0.23 | 0.23 | 0.24 | 0.26 | 0.27 |
| RRT 0.61 | — | — | — | 0.14 | 0.12 | 0.14 | 0.18 |
| CBD | 0.16 | — | — | — | — | — | — |
| CBN | 0.56 | 0.53 | 0.60 | 0.56 | 0.62 | 0.68 | 0.69 |
| RRT 0.93 | 0.52 | 0.51 | 0.53 | 0.49 | 0.52 | 0.51 | 0.47 |
| Total | 1.6 | 1.5 | 1.7 | 1.9 | 1.9 | 2.1 | 2.3 |
| Impurity (% Area) | | | | | | | |
| RRT 0.40 | 0.12 | 0.33 | 0.43 | 0.57 | 0.47 | 0.64 | 0.91 |
| RRT 0.46 | 0.26 | 0.26 | 0.26 | 0.29 | 0.29 | 0.32 | 0.36 |
| RRT 0.61 | — | — | — | 0.17 | 0.14 | 0.17 | 0.23 |
| CBD | 0.18 | — | — | — | — | — | — |
| CBN | 0.66 | 0.66 | 0.70 | 0.69 | 0.73 | 0.83 | 0.90 |
| RRT 0.93 | 0.61 | 0.63 | 0.61 | 0.61 | 0.61 | 0.62 | 0.61 |
| Total | 1.8 | 1.9 | 2.0 | 2.3 | 2.2 | 2.6 | 3.0 |

* RRT0.70 was removed from the original data report as re-analysis revealed it was noise, not an actual impurity peak.

Impurity growth conforms to the trend observed by week 2. The assay decreased to 76.3% LC by week 2 in the BFS ampoule at 25° C./60% RH, indicating adsorption may have occurred.

Example 28: Evaluation on Microfluidizer Process Conditions

This example relates to micro-fluidizer process development. A placebo PE10C trial run #1 was carried out to determine the process pressure needed to produce a product that can be sterile filtered.

Process pressures: 10 kpsi, 20 kpsi, and 30 kpsi; 5 passes for each pressure setting.
Product cooling: 5° C. circulated water bath at the product outlet (after interaction chamber).
Sample analysis: 10 mL of each sample was filtered with a 0.2 μm PES filter; and the before and after filtration samples were tested for PSD.

Figure 6:
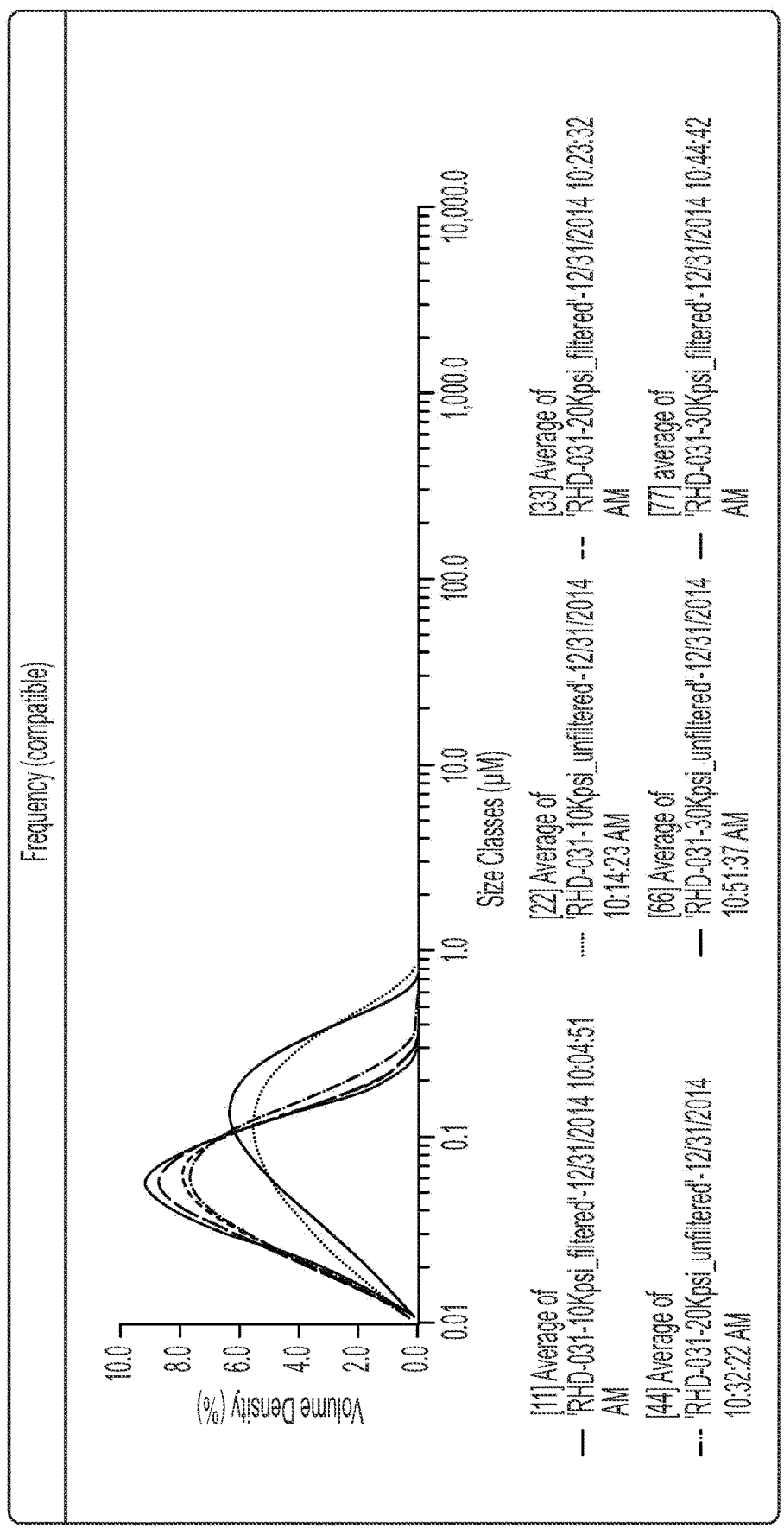
FIG. 6 shows a representative particle size distribution plot of the micro-fluidized placebo samples described in Example 28.

The PSD of micro-fluidized placebo run #1 samples are shown in FIG. 6 and Table 28.

TABLE 28

PSD of Micro-Fluidized Placebo Samples (before & after filtration)

| Process Pressure (kpsi) | Filtered (Y/N) | Resistance during Filtration | PSD (um) | | | |
|---|---|---|---|---|---|---|
| | | | D10 | D50 | D90 | D99 |
| 10 | Y | Large resistance | 0.0303 | 0.109 | 0.313 | 0.519 |
| | N | — | 0.0252 | 0.0978 | 0.331 | 0.596 |
| 20 | Y | Small resistance | 0.0227 | 0.0584 | 0.145 | 0.255 |
| | N | — | 0.0225 | 0.0590 | 0.151 | 0.267 |
| 30 | Y | No resistance | 0.0241 | 0.0551 | 0.122 | 0.203 |
| | N | — | 0.0236 | 0.0562 | 0.129 | 0.218 |

A large PSD change was observed for the 10 kpsi sample after filtration, indicating retention of oil droplets was significant. The PSD shift after filtration was small for both 20 kpsi and 30 kpsi, indicating retention of oil droplets was insignificant for these two samples.

A placebo PE10C trial run #2 was also performed in this example to evaluate the product temperature rise at various process pressures.

Process pressures: 15 kpsi, 20 kpsi, and 25 kpsi and 27 kpsi; 5 passes for each pressure setting. The targeted highest pressure was 30 kpsi, however during the process the highest achievable pressure was only 27 kpsi.
Product cooling: the first pass of each pressure setting was not cooled, and the product temperature was measured; the 4 following passes were cooled using a 5° C. circulated water bath.
Sample analysis: 50 mL of each sample was filtered with a 0.2 μm PES filter; and the before and after filtration samples were tested for PSD.

Figure 7:
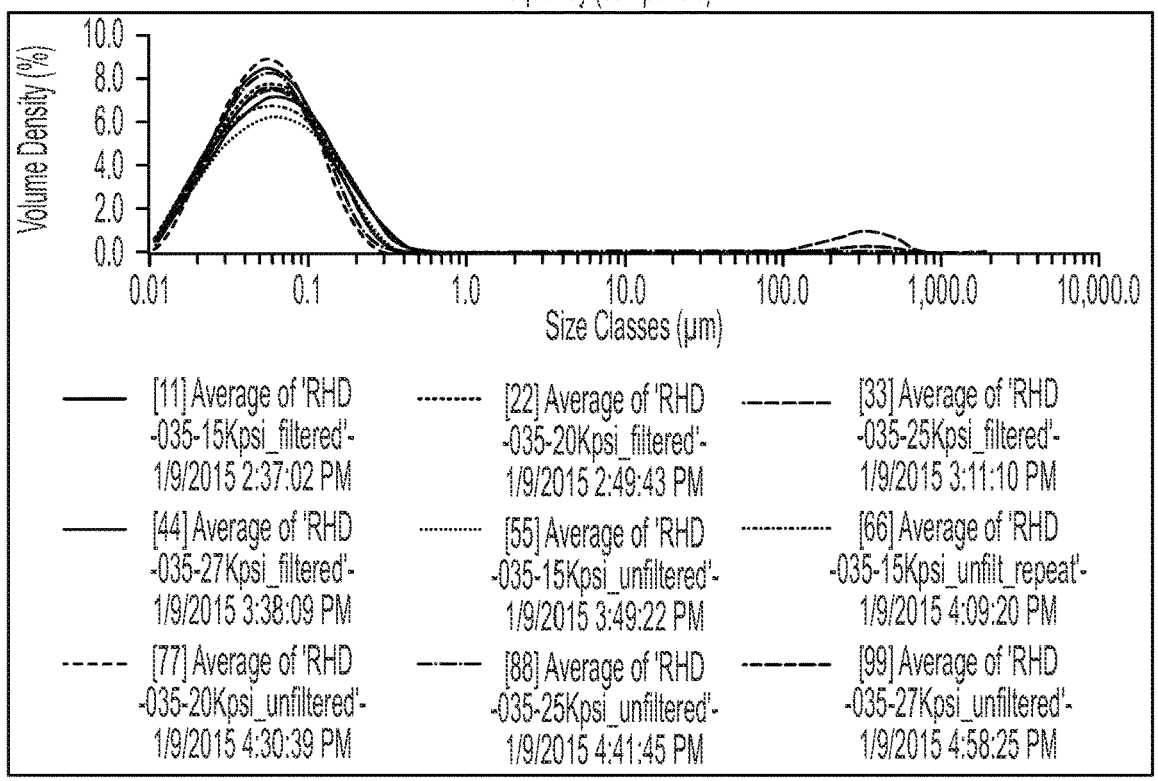
FIG. 7 shows a representative particle size distribution plot of the micro-fluidized placebo samples described in Example 28.

The microfluidizer used in this study was the M110P microfluidizer by Microfluidics, having an on-board 1.5 KW (2HP) electric-hydraulic drive and a single-acting intensifier pump. Process pressures of the microfluidizer are adjustable from 138-2068 bar (2,000-30,000 psi). The PSD values of the microfluidized placebo run #2 samples are shown in FIG. 7 and Table 29.

TABLE 29

PSD and Process Temperature of Micro-Fluidized Placebo Samples

| Process Pressure (kpsi) | Temp. without Cooling (° C., 1 Pass) | Filtered (Y/N, 5 Passes) | [1]Resistance during Filtration (5 Passes) | PSD (μm, 5 Passes) | | | |
|---|---|---|---|---|---|---|---|
| | | | | D10 | D50 | D90 | D99 |
| 15 | 25.0 | Y | Moderate resistance | 0.0220 | 0.0618 | 0.169 | 0.308 |
| | | N | — | 0.0218 | 0.0679 | 0.266 | [2]476 |
| 20 | 24.9 | Y | Moderate resistance | 0.0218 | 0.0566 | 0.143 | 0.248 |
| | | N | — | 0.0221 | 0.0583 | 0.150 | 0.264 |
| 25 | 32.5 | Y | Small resistance | 0.0232 | 0.0542 | 0.123 | 0.204 |
| | | N | — | 0.0222 | 0.0547 | 0.132 | 0.226 |
| 27 | 30.2 | Y | No resistance | 0.0227 | 0.0550 | 0.129 | 0.221 |
| | | N | — | 0.0218 | 0.0580 | 0.158 | [2]292 |

[1]The resistance documented here was the initial resistance; roughly halfway through filtration of the 50 ml sample, more resistance was observed in all samples.
[2]The large D99 was due to the small peak around 300 μm. This peak was randomly observed, possibly caused by air bubbles.

In this experiment, the product temperature did not rise from 15 kpsi to 20 kpsi, while a significant temperature rise was observed from 20 kpsi to 25 kpsi. The PSD shift after filtration was large for 15 kpsi, but small for 20 kpsi and higher pressures; increasing pressure above 20 kpsi did not seem to reduce this shift. Because the product collected at the outlet was already air-cooled when passing through the outlet coil, the actual temperature rise after the interaction chamber (before the coil) was higher than the collected product temperature; therefore the 25 kpsi sample may have been exposed to temperature higher than 40° C., the known temperature range which dronabinol is known to be unstable. Based on the results, it is recommended the active formulation AE10C be processed at 20 kpsi in order to avoid API degradation. The processed formulation can be filtered and tested for assay to determine whether the retention by the filter is significant.

Example 29: Particle Size Distribution (PSD) Method by Microfluidizer

Figure 8:
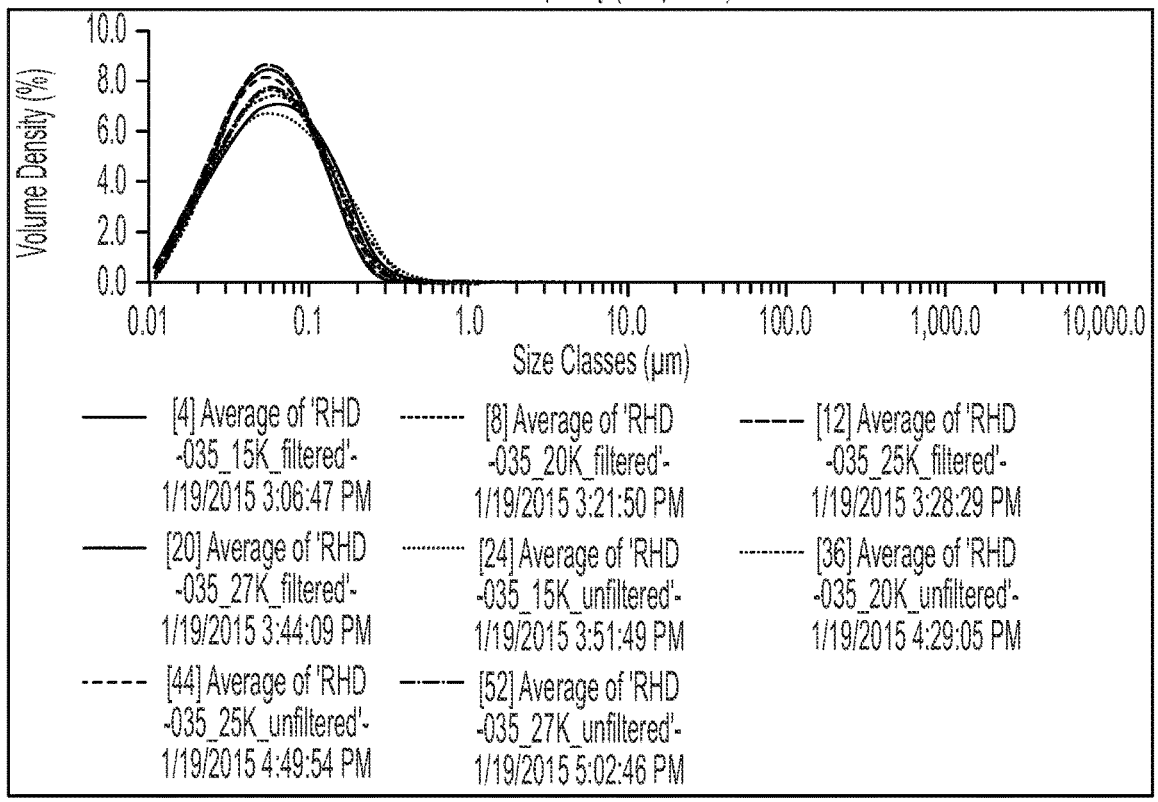
FIG. 8 shows a representative particle size distribution plot of the micro-fluidized placebo samples described in Example 29.

In this example, an alternative PSD method was developed. Specifically, an air bubble removing procedure was included (5-10 seconds of sonication was applied prior to the measurements) and the peak around 400 μm (air bubble peak) (FIG. 7) was eliminated. Data quality was improved. The PE10C placebo samples processed at varied pressure were re-tested. The new PSD results are shown in FIG. 8 and Table 30. In Table 30, the resistance is the initial resistance. Roughly halfway through filtration of the 50 mL sample, more resistance was observed in all samples. The large D99 was believed to be due to a small peak around 300 μm. This peak was randomly observed, possibly caused by air bubbles.

TABLE 30

PSD and Process Temperature of Microfluidized Placebo Samples
(Repeated PSD Measurements)

| Process Pressure (kpsi) | Temp. without Cooling (° C., 1 Pass) | Filtered (Y/N, 5 Passes) | Resistance during Filtration (5 Passes) | PSD (μm, 5 Passes) | | | |
|---|---|---|---|---|---|---|---|
| | | | | D10 | D50 | D90 | D99 |
| 15 | 25.0 | Y | Moderate resistance | 0.0220 | 0.0618 | 0.169 | 0.308 |
| | | N | — | 0.0206 | 0.0594 | 0.175 | 0.335 |
| 20 | 24.9 | Y | Moderate resistance | 0.0219 | 0.0575 | 0.147 | 0.258 |
| | | N | — | 0.0219 | 0.590 | 0.156 | 0.276 |
| 25 | 32.5 | Y | Small resistance | 0.0229 | 0.0547 | 0.126 | 0.211 |
| | | N | — | 0.0220 | 0.0544 | 0.133 | 0.231 |
| 27 | 30.2 | Y | No resistance | 0.0227 | 0.0548 | 0.128 | 0.216 |
| | | N | — | 0.0223 | 0.0581 | 0.147 | 0.260 |

Example 30: Forced Degradation Study on API

In this example, a forced degradation study was performed on the API, drug product emulsion, and a placebo. The stress conditions are given in Table 31, and the test results are shown in Tables 32-34. Only w/w % impurities are presented.

TABLE 31

PSD and Process Temperature of Microfluidized Placebo Samples

| Sample # | Description | Task/Purpose | Duration | Container | Preparation | Post Duration (after exposure to stress condition) |
|---|---|---|---|---|---|---|
| 1 | API Control | Control | N/A | 25 mL VF | 25 mg of API (50% in sesame oil) | QS w/diluent (50/50 |
| 2 | Placebo Control | Control | N/A | 10 mL VF | 1 g of placebo | QS w/diluent |
| 3 | DP Control | Control | N/A | 10 mL VF | 1 g of drug product | QS w/diluent |
| 4 | Acid/Base Mixture | System peak | N/A | LC vial | 0.5 mL of 0.1N HCl + 0.5 mL of 0.1N NaOH | N/A |
| 5 | H2O2 Only | System peak | N/A | LC vial | 1.0 mL of 1% H2O2 | N/A |
| 6 | API-Thermal | Stress condition | 24 hr | 25 mL VF | 25 mg of API only. Exposed at 80° C. | QS w/diluent |
| 7 | API-Acid | Stress condition | 24 hr | 25 mL VF | 25 mg of API + 0.5 mL of 0.1N HCl | Add 0.5 mL of 0.1N NaOH, QS w/diluent |
| 8 | API-Base | Stress condition | 24 hr | 25 mL VF | 25 mg of API + 0.5 mL of 0.1N NaOH | Add 0.5 mL of 0.1N HCl, QS w/diluent |
| 9 | API-Oxidation | Stress condition | 30 min | 25 mL VF | 25 mg of API + 0.2 mL of 1% H2O2 | QS w/diluent |
| 10 | API-Photolyltic | Stress condition | 24 hr | 25 mL VF | 25 mg of API only. Expose the VF to light (720 watts/m$^2$) | QS w/diluent |
| 11 | Placebo-Thermal | Stress condition | 24 hr | 10 mL VF | 1 g of placebo only. Exposed the VF at 80° C. | QS w/diluent |
| 12 | Placebo-Acid | Stress condition | 24 hr | 10 mL VF | 1 g of placebo + 0.2 mL of 0.1N HCl | Add 0.2 mL of 0.1N NaOH, QS w/diluent |
| 13 | Placebo-Base | Stress condition | 24 hr | 10 mL VF | 1 g of placebo + 0.2 mL of 0.1N NaOH | Add 0.2 mL of 0.1N HCl, QS w/diluent |
| 14 | Placebo-Oxidation | Stress condition | 30 min | 10 mL VF | 1 g of placebo + 0.2 mL of 1% H2O2 | QS w/diluent |
| 15 | Placebo-Photolyltic | Stress condition | 24 hr | 10 mL VF | 1 g of placebo only. Expose the VF to light (720 watts/m$^2$) | QS w/diluent |
| 16 | DP-Thermal | Stress condition | 24 hr | 10 mL VF | 1 g of DP only. Exposed the VF at 80° C. | QS w/diluent |
| 17 | DP-Acid | Stress condition | 24 hr | 10 mL VF | 1 g of DP + 0.2 mL of 0.1N HCl | Add 0.2 mL of 0.1N NaOH, QS w/diluent |
| 18 | DP-Base | Stress condition | 24 hr | 10 mL VF | 1 g of DP + 0.2 mL of 0.1N NaOH | Add 0.2 mL of 0.1N HCl, QS w/diluent |
| 19 | DP-Oxidation | Stress condition | 30 min | 10 mL VF | 1 g of DP + 0.2 mL of 1% H2O2 | QS w/diluent |
| 20 | DP-Photolyltic | Stress condition | 24 hr | 10 mL VF | 1 g of DP only. Expose the VF to light (720 watts/m$^2$) | QS w/diluent |

TABLE 32

Forced Degradation Results of Placebo

| Sample Condition | Placebo | | | | | |
|---|---|---|---|---|---|---|
| | Control | Thermal | Acid | Base | Oxidation | Photolytic |
| Duration | n/a | 24 hr | 24 hr | 24 hr | 0.5 hr | 24 hr |
| Assay % LC | n/a | n/a | n/a | n/a | n/a | n/a |
| % Area | n/a | n/a | n/a | n/a | n/a | n/a |
| % w/w Impurities based on 0.5% Formulation | | | | | | |
| RRT 0.28 | — | — | — | — | — | 0.09 |
| RRT 0.30 | — | — | — | — | — | — |
| RRT 0.34 | — | — | — | — | — | — |
| RRT 0.39 | — | — | — | — | — | — |
| RRT 0.40 | — | — | — | — | — | 0.18 |
| RRT 0.44 | — | — | — | — | — | — |
| RRT 0.46 | — | — | — | — | — | — |
| RRT 0.49 | — | — | — | — | — | — |
| RRT 0.52 | — | — | — | — | — | 0.17 |
| RRT 0.56 | — | — | — | — | — | — |
| RRT 0.62 | — | — | — | — | — | — |
| CBD | — | — | — | — | — | — |
| RRT 0.70 | — | — | — | — | — | — |
| RRT 0.75 | — | — | — | — | — | — |
| RRT 0.82 | — | — | — | — | — | — |

TABLE 32-continued

Forced Degradation Results of Placebo

| Sample Condition | Placebo | | | | | |
|---|---|---|---|---|---|---|
| | Control | Thermal | Acid | Base | Oxidation | Photolytic |
| CBN | — | — | — | — | — | — |
| RRT 0.93 | — | — | — | — | — | — |
| RRT 1.19 | — | — | — | 0.31 | — | — |
| RRT 1.21 | 0.63 | 0.63 | 0.74 | 4.28 | 0.60 | — |
| RRT 1.27 | 2.17 | 1.88 | 2.21 | 2.15 | 1.97 | — |
| RRT 1.30 | — | — | — | — | — | — |
| RRT 1.35 | 2.71 | 2.36 | 2.72 | 2.23 | 2.14 | — |
| RRT 1.40 | — | — | — | — | — | — |
| RRT 1.45 | — | — | — | — | — | — |
| RRT 1.48 | — | — | — | 0.11 | — | — |
| Total | 5.5 | 4.9 | 5.7 | 9.1 | 4.7 | 0.4 |

TABLE 33

Forced Degradation Results of Active Drug Product

| Sample Condition | Drug Product | | | | | |
|---|---|---|---|---|---|---|
| | Control | Thermal | Acid | Base | Oxidation | Photolytic |
| Duration | n/a | 24 hr | 24 hr | 24 hr | 0.5 hr | 24 hr |
| Assay % LC | 83.7 | 75.3 | 83.9 | 84.0 | 83.9 | 0.0 |
| % Area | 92.2 | 83.4 | 91.4 | 90.0 | 92.2 | 0.0 |
| % w/w Impurities based on 0.5% Formulation | | | | | | |
| RRT 0.28 | — | — | — | — | — | 0.12 |
| RRT 0.30 | 0.24 | 0.10 | — | 0.17 | 0.25 | — |
| RRT 0.34 | — | — | 0.16 | — | — | — |
| RRT 0.39 | — | — | — | — | — | — |
| RRT 0.40 | 0.62 | 2.99 | 0.80 | 0.72 | 0.61 | 0.97 |
| RRT 0.44 | — | — | — | — | — | — |
| RRT 0.46 | 0.33 | 0.90 | 0.34 | 0.31 | 0.33 | 0.48 |
| RRT 0.49 | — | — | — | — | — | — |
| RRT 0.52 | — | 0.15 | — | 0.10 | — | 0.38 |
| RRT 0.56 | — | — | — | — | — | — |
| RRT 0.62 | 0.28 | 1.26 | 0.39 | 0.21 | 0.30 | 0.74 |
| CBD | — | — | — | — | — | — |
| RRT 0.70 | — | — | — | — | — | 0.19 |
| RRT 0.75 | — | 0.32 | — | — | — | — |
| RRT 0.82 | 0.14 | 0.13 | 0.27 | 0.15 | 0.14 | 1.10 |
| CBN | 0.61 | 4.14 | 0.94 | 0.66 | 0.60 | — |
| RRT 0.93 | 0.44 | — | 0.47 | 0.44 | 0.45 | — |
| RRT 1.19 | — | — | — | 0.22 | — | — |
| RRT 1.21 | 0.67 | 0.67 | 0.76 | 3.05 | 0.67 | — |
| RRT 1.27 | 1.81 | 1.97 | 1.82 | 1.73 | 1.79 | 0.25 |
| RRT 1.30 | — | — | — | — | — | 0.41 |
| RRT 1.35 | 1.98 | 2.20 | 1.97 | 1.61 | 1.97 | 0.47 |
| RRT 1.40 | — | 0.20 | — | — | — | 0.40 |
| RRT 1.45 | — | — | — | — | — | — |
| RRT 1.48 | — | — | — | — | — | — |
| Total | 7.1 | 15.0 | 7.9 | 9.4 | 7.1 | 5.5 |

TABLE 34

Forced Degradation Results of API (THC)

| Sample Condition | API | | | | | |
|---|---|---|---|---|---|---|
| | Control | Thermal | Acid | Base | Oxidation | Photolytic |
| Duration | n/a | 24 hr | 24 hr | 24 hr | 0.5 hr | 24 hr |
| Assay % LC | 85.8 | 52.8 | 83.6 | 82.9 | 78.6 | 2.3 |
| % Area | 97.5 | 77.5 | 96.0 | 95.3 | 97.5 | 11.3 |
| % w/w Impurities | | | | | | |
| RRT 0.28 | — | — | — | — | — | — |
| RRT 0.30 | — | 0.15 | 0.08 | 0.13 | — | — |
| RRT 0.34 | — | — | — | — | — | — |
| RRT 0.39 | — | — | — | — | — | 0.79 |
| RRT 0.40 | — | — | 0.71 | 1.72 | — | 0.66 |
| RRT 0.44 | — | 0.47 | — | — | — | — |
| RRT 0.46 | 0.28 | 0.56 | 0.22 | 0.30 | 0.25 | 4.05 |
| RRT 0.49 | — | — | 0.37 | — | — | 2.55 |
| RRT 0.52 | — | 0.40 | — | — | — | — |
| RRT 0.56 | — | 0.22 | 0.18 | 0.42 | — | — |
| RRT 0.62 | — | — | 0.37 | 0.31 | 0.49 | 1.45 |
| CBD | 0.52 | 2.43 | — | — | — | — |
| RRT 0.70 | — | 0.29 | — | — | — | — |
| RRT 0.75 | — | — | — | — | — | 0.25 |
| RRT 0.82 | — | — | — | — | — | 0.49 |
| CBN | 1.41 | 9.03 | 1.54 | 1.19 | 1.27 | 6.75 |
| RRT 0.93 | — | — | — | — | — | — |
| RRT 1.19 | — | 0.54 | — | — | — | 0.83 |
| RRT 1.21 | — | — | — | — | — | — |
| RRT 1.27 | — | 0.26 | — | — | — | — |
| RRT 1.30 | — | — | — | — | — | — |
| RRT 1.35 | — | — | — | — | — | — |
| RRT 1.40 | — | 0.50 | — | — | — | — |
| RRT 1.45 | — | 0.34 | — | — | — | 0.07 |
| RRT 1.48 | — | 0.14 | — | — | — | — |
| Total | 2.2 | 15.3 | 3.5 | 4.1 | 2.0 | 17.9 |

The impurity profile in this experiment is summarized in Table 35. Only impurities that have been detected in the stability samples are listed. RRT 0.93 was only reported in the drug product and not in the API. This is because on the chromatogram RRT 0.93 is very close to the CBN peak and the CBN peak is much larger in the API than in the drug product, RRT 0.93 cannot be differentiated from CBN in the API chromatograph.

TABLE 35

Summary of Stress Condition and Impurities

| Stress Condition/ Impurity Change | Thermal | Acid | Base | Oxidation | Photolytic |
|---|---|---|---|---|---|
| RRT 0.40 | 1 | 1, 2 | 1, 2 | — | 1, 2 |
| RRT 0.46 | 1, 2 | — | — | — | 1, 2 |
| RRT 0.62 | 1 | 1, 2 | 2 | 2 | 1, 2 |
| CBD | 2 | 2 | 2 | 2 | 2 |
| CBN | 1, 2 | 1 | — | — | 1, 2 |
| RRT 0.93 | 1 | — | — | — | 1 |

1: Increase in drug product;
2: Increase in API;
Blank cell: no effect

Because pH neutral formulation is intended, the effects of acid and base are not discussed here.

Oxidation appears to have very little effect on degradation. Light exposure appears to have caused the most significant degradation. The only effect that oxidation has is the apparent transformation of CBD to RRT 0.62, which could also occur from photolytic degradation. The forced degradation results indicate oxidation may not be the primary cause of the drug product instability.

Example 31: Development of Particle Size Distribution Method

In this example, a Mastersizer 3000 method was developed using parameters obtained from the Malvern ZetaSizer (Malvern Instruments). The results obtained in this example were consistent with both the ZetaSizer and the measurement done at Microfluidics with Horiba (as shown in FIG. 2). The data for this experiment (batch #RHD-035 comprising 2% Tween 80, 2.5% glycerin, 2% sesame oil and WFI q.s. to 100%) at 20 kpsi sample are shown in FIG. 9 and FIG. 10.

Figure 9:
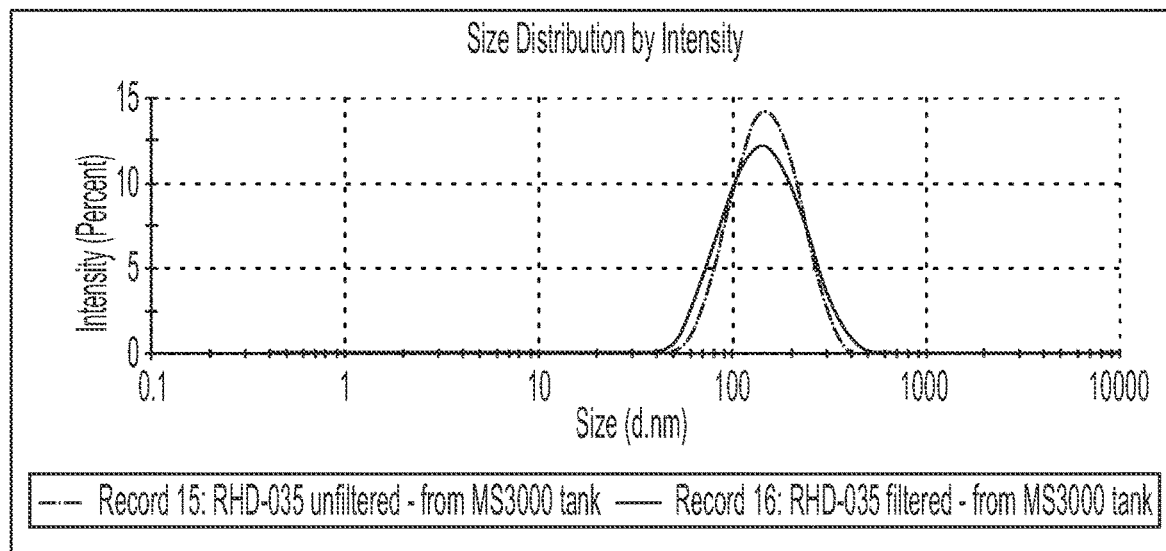
FIG. 9 shows a representative particle size distribution plot of RHD-35 samples described in Example 31. Intensity-based size distribution data is shown.
Figure 10:
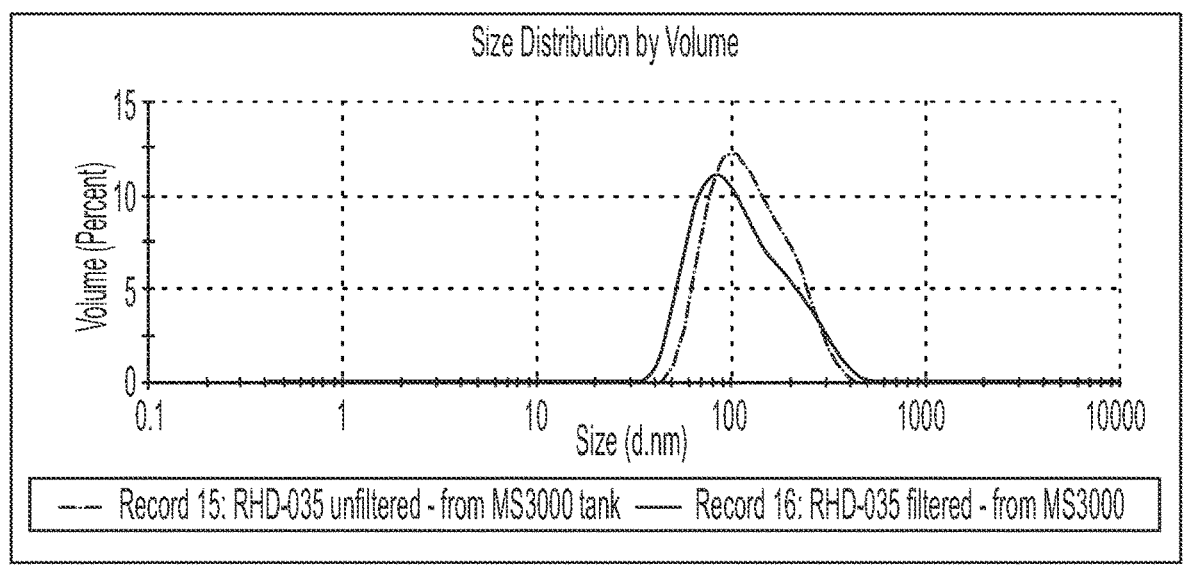
FIG. 10 shows a representative particle size distribution plot of RHD-35 samples described in Example 31. Volume-based size distribution data is shown.

In FIG. 9, the intensity-based size distributions are measured for two RD-035 samples after sampling them directly from the MS 3000 accessory tank. In FIG. 10, volume-based size distributions were measured for the two RHD-035 samples after sampling them directly from the MS 3000 accessory tank.

| Sample Name | Cumulative Analysis | | Distributional Analysis | | |
|---|---|---|---|---|---|
| | Z-Ave (nm) | PdI | Peak 1 (nm) | Peak 2 (nm) | Peak 3 (nm) |
| RHD-035 (unfiltered) | 129 ± 1 | 0.18 | 157 ± 2 | 0 | 0 |
| RHD-035 (unfiltered) | 128 ± 1 | 0.29 | 159 ± 2 | 0 | 0 |

Figure 11:
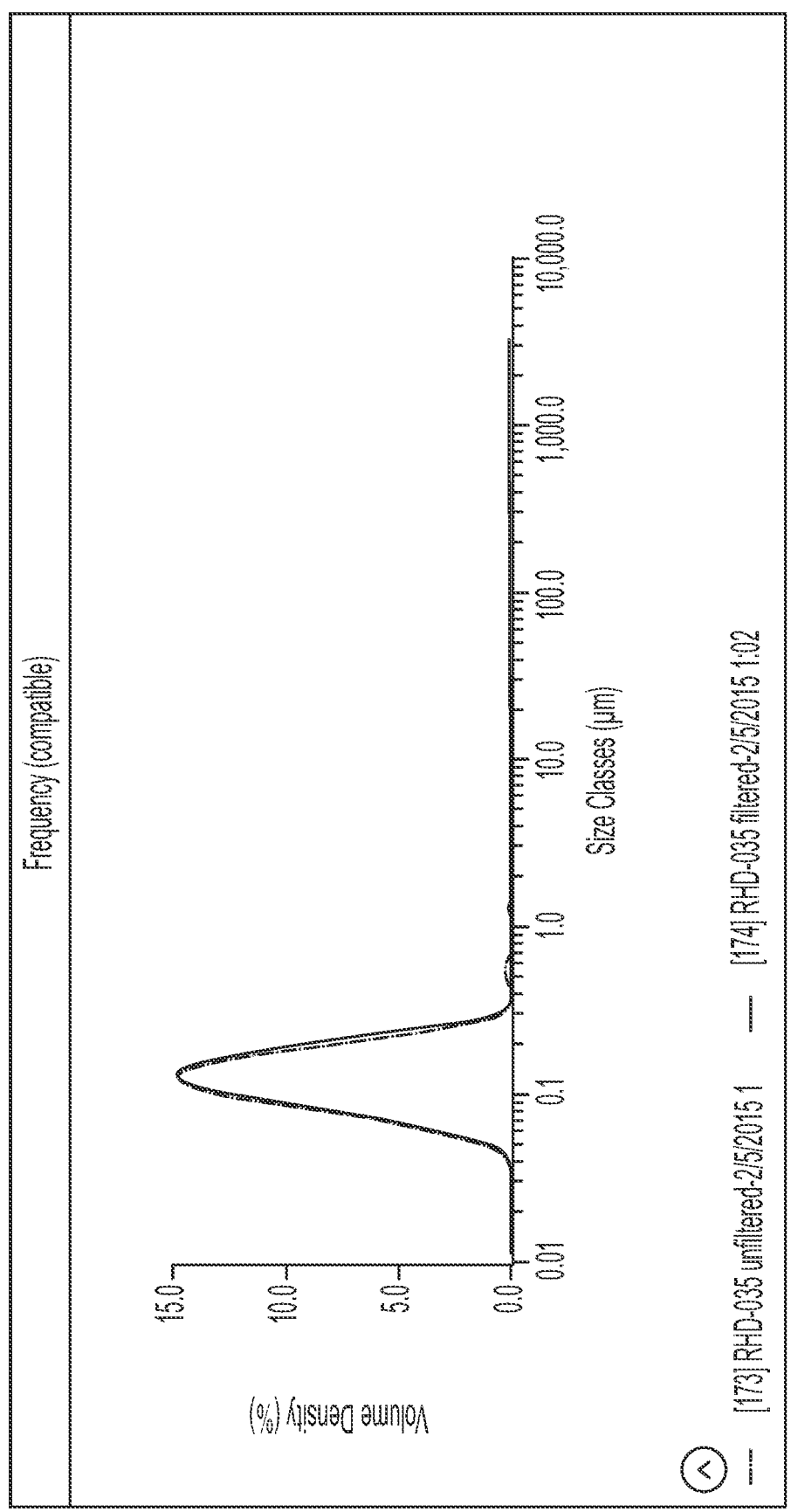
FIG. 11 shows a representative particle size distribution plot of RHD-35 samples described in Example 31. Size distributions obtained with laser diffraction are shown.

The ZetaSizer measurement of batch #RHD-035 at 20 kpsi is shown in FIG. 11. The size distribution obtained with laser diffraction for the RHD-035 emulsions is indicated.

| Sample Name | Dx(10) (μm) | Dx(50) (μm) | Dx(90) (μm) | Dx(99) (μm) |
|---|---|---|---|---|
| RHD-035 (unfiltered) | 0.0731 | 0.124 | 0.202 | 0.464 |
| RHD-035 (filtered) | 0.0759 | 0.128 | 0.208 | 0.273 |

This example shows that the Malvern MS 3000 is suitable for the microfluidizer processed product. 20 kpsi process pressure can generate an emulsion with small enough oil droplets to pass through 0.2 um filters without significant PSD shift.

Example 32: Forced Degradation on Oxidative Stability

In this example, an additional forced degradation study was performed. Harsh conditions for oxidation (14202 concentration increased from 1% to 3%, exposure increased from 30 min to 2 hr) and conditions for photolytic degradation (exposure decreased from 24 hr to 40 min) were used in an additional forced degradation study. Results of the $2^{nd}$ forced degradation are shown in Table 36 and Table 37.

TABLE 36

Additional Forced Degradation Results: Drug Product

| Sample Condition | Drug Product (1$^{st}$ Study) | | | | | Sample Condition | Drug Product (2$^{nd}$ Study) | | |
|---|---|---|---|---|---|---|---|---|---|
| | Control | Thermal | Acid | Base | Oxidation 1% H2O2 | Photolytic | | Control | Oxidation 3% H2O2 | Photolytic |
| Duration | n/a | 24 hr | 24 hr | 24 hr | 0.5 hr | 24 hr | Duration | n/a | 2 hr | 40 min |
| Assay % LC | 83.7 | 75.3 | 83.9 | 84.0 | 83.9 | 0.0 | Assay % LC | 82.3 | 83.2 | 71.9 |
| % Area | 92.2 | 83.4 | 91.4 | 90.0 | 92.2 | 0.0 | % Area | 92.2 | 92.2 | 83.5 |
| % w/w Impurities | | | | | | | | | | |
| RRT 0.28 | — | — | — | — | — | 0.12 | RRT 0.28 | — | — | — |
| RRT 0.30 | 0.24 | 0.10 | — | 0.17 | 0.25 | — | RRT 0.30 | 0.23 | 0.23 | 0.30 |
| RRT 0.34 | — | — | 0.16 | — | — | — | RRT 0.34 | — | — | — |
| RRT 0.39 | — | — | — | — | — | — | RRT 0.39 | — | — | — |
| RRT 0.40 | 0.62 | 2.99 | 0.80 | 0.72 | 0.61 | 0.97 | RRT 0.40 | 0.61 | 0.62 | 0.58 |
| RRT 0.44 | — | — | — | — | — | — | RRT 0.44 | — | — | — |
| RRT 0.46 | 0.33 | 0.90 | 0.34 | 0.31 | 0.33 | 0.48 | RRT 0.46 | 0.33 | 0.33 | 0.94 |
| RRT 0.49 | — | — | — | — | — | — | RRT 0.49 | — | — | — |
| RRT 0.52 | — | 0.15 | — | 0.10 | — | 0.38 | RRT 0.52 | — | — | 0.31 |
| RRT 0.56 | — | — | — | — | — | — | RRT 0.56 | — | — | 0.49 |
| RRT 0.62 | 0.28 | 1.26 | 0.39 | 0.21 | 0.30 | 0.74 | RRT 0.62 | 0.31 | 0.29 | 2.68 |
| CBD | — | — | — | — | — | — | CBD | — | — | — |
| RRT 0.70 | — | — | — | — | — | 0.19 | RRT 0.70 | — | — | — |
| RRT 0.75 | — | 0.32 | — | — | — | — | RRT 0.75 | — | — | 2.28 |
| RRT 0.82 | 0.14 | 0.13 | 0.27 | 0.15 | 0.14 | 1.10 | RRT 0.82 | 0.12 | 0.13 | — |
| CBN | 0.61 | 4.14 | 0.94 | 0.66 | 0.60 | — | CBN | 0.60 | 0.61 | 0.80 |
| RRT 0.93 | 0.44 | — | 0.47 | 0.44 | 0.45 | — | RRT 0.93 | 0.44 | 0.46 | — |
| RRT 1.19 | — | — | — | 0.22 | — | — | RRT 1.19 | — | — | — |
| RRT 1.21 | 0.67 | 0.67 | 0.76 | 3.05 | 0.67 | — | RRT 1.21 | 0.68 | 0.67 | 0.72 |
| RRT 1.27 | 1.81 | 1.97 | 1.82 | 1.73 | 1.79 | 0.25 | RRT 1.27 | 1.76 | 1.75 | 2.04 |
| RRT 1.30 | — | — | — | — | — | 0.41 | RRT 1.30 | — | — | — |
| RRT 1.35 | 1.98 | 2.20 | 1.97 | 1.61 | 1.97 | 0.47 | RRT 1.35 | 1.93 | 1.94 | 2.23 |
| RRT 1.40 | — | 0.20 | — | — | — | 0.40 | RRT 1.40 | — | — | 0.17 |
| RRT 1.45 | — | — | — | — | — | — | RRT 1.45 | — | — | — |
| RRT 1.48 | — | — | — | — | — | — | RRT 1.48 | — | — | 0.23 |
| Total | 7.1 | 15.0 | 7.9 | 9.4 | 7.1 | 5.5 | Total | 7.0 | 7.0 | 13.8 |

TABLE 37

Additional Forced Degradation Results: API

| Sample Condition | API (1st Study) | | | | | | Sample Condition | API (2nd Study) | | |
| --- | --- | --- | --- | --- | --- | --- | --- | --- | --- | --- |
| | Control | Thermal | Acid | Base | Oxidation 1% H2O2 | Photolytic | | Control | Oxidation 3% H2O2 | Photolytic |
| Duration | n/a | 24 hr | 24 hr | 24 hr | 0.5 hr | 24 hr | Duration | n/a | 2 hr | 40 min |
| Assay % LC | 85.8 | 52.8 | 83.6 | 82.9 | 78.6 | 2.3 | Assay % LC | 85.8 | 83.7 | 57.5 |
| % Area | 97.5 | 77.5 | 96.0 | 95.3 | 97.5 | 11.3 | % Area | 97.4 | 97.0 | 79.1 |
| | | | | | | % w/w Impurities | | | | |
| RRT 0.28 | — | — | — | — | — | — | RRT 0.28 | — | — | — |
| RRT 0.30 | — | 0.15 | 0.08 | 0.13 | — | — | RRT 0.30 | — | — | 0.07 |
| RRT 0.34 | — | — | — | — | — | — | RRT 0.34 | — | — | — |
| RRT 0.39 | — | — | — | — | — | 0.79 | RRT 0.39 | — | — | — |
| RRT 0.40 | — | — | 0.71 | 1.72 | — | 0.66 | RRT 0.40 | — | — | — |
| RRT 0.44 | — | 0.47 | — | — | — | — | RRT 0.44 | — | — | 0.68 |
| RRT 0.46 | 0.28 | 0.56 | 0.22 | 0.30 | 0.25 | 4.05 | RRT 0.46 | 0.26 | 0.29 | 1.35 |
| RRT 0.49 | — | — | 0.37 | — | — | 2.55 | RRT 0.49 | — | — | — |
| RRT 0.52 | — | 0.40 | — | — | — | — | RRT 0.52 | — | — | 1.56 |
| RRT 0.56 | — | 0.22 | 0.18 | 0.42 | — | — | RRT 0.56 | — | 0.20 | 0.17 |
| RRT 0.62 | — | — | 0.37 | 0.31 | 0.49 | 1.45 | RRT 0.62 | — | — | — |
| CBD | 0.52 | 2.43 | — | — | — | — | CBD | 0.58 | 0.62 | 8.20 |
| RRT 0.70 | — | 0.29 | — | — | — | — | RRT 0.70 | — | — | 0.62 |
| RRT 0.75 | — | — | — | — | — | 0.25 | RRT 0.75 | — | — | — |
| RRT 0.82 | — | — | — | — | — | 0.49 | RRT 0.82 | — | — | 0.22 |
| CBN | 1.41 | 9.03 | 1.54 | 1.19 | 1.27 | 6.75 | CBN | 1.41 | 0.79 | 1.00 |
| RRT 0.93 | — | — | — | — | — | — | RRT 0.93 | — | 0.65 | — |
| RRT 1.19 | — | 0.54 | — | — | — | 0.83 | RRT 1.19 | — | — | — |
| RRT 1.21 | — | — | — | — | — | — | RRT 1.21 | — | — | — |
| RRT 1.27 | — | 0.26 | — | — | — | — | RRT 1.27 | — | — | — |
| RRT 1.30 | — | — | — | — | — | — | RRT 1.30 | — | — | — |
| RRT 1.35 | — | — | — | — | — | — | RRT 1.35 | — | — | 0.21 |
| RRT 1.40 | — | 0.50 | — | — | — | — | RRT 1.40 | — | — | 0.21 |
| RRT 1.45 | — | 0.34 | — | — | — | 0.07 | RRT 1.45 | — | — | 0.52 |
| RRT 1.48 | — | 0.14 | — | — | — | — | RRT 1.48 | — | — | 0.40 |
| Total | 2.2 | 15.3 | 3.5 | 4.1 | 2.0 | 17.9 | Total | 2.3 | 2.6 | 15.2 |

In this example, the oxidation impurity profile was found to be very similar to the first study, indicating that oxidation may not play a significant role in degradation. However, it is possible oxidation by oxygen is different from hydrogen peroxide and could be significant to the stability of product. No apparent shift from CBD to RRT 0.62 was observed in the second study. However, this is not a significant change since CBD and RRT 0.62 could be the same impurity. The photolytic impurity profile is similar to the first study, although the degradation is to a lesser extent. Assay decreased by roughly 10% for drug product and 30% for API, indicating dronabinol is very unstable under light exposure. The mass balance also suggests there are degradation products that are not detected.

Example 33: Stability of Active Batch

In this example, the stability of AE14B was tested. The results are shown in Table 38 and Table 39.

TABLE 38

Chemical Stability of AE14B in Glass Vial (up to 8 W)

Product: Dronabinol AE14B Formulation in Glass Vial

| | Storage Condition | | | | | | | | |
| --- | --- | --- | --- | --- | --- | --- | --- | --- | --- |
| | 5° C. | | | | | 25° C./60% RH | | | |
| Time Point | Initial | 1 W | 2 W | 4 W | 8 W | 1 W | 2 W | 4 W | 8 W |
| Appearance | No phase separation | No phase separation | No phase separation | No phase separation | No phase separation | No phase separation | No phase separation | No phase separation | No phase separation |
| PH | 6.0 | 6.4 | 6.8 | 6.4 | 6.1 | 6.7 | 6.8 | 6.5 | 6.5 |
| Assay (% LC) | 88.1 | 83.5 | 88.1 | 86.4 | 84.2 | 85.1 | 89.0 | 86.9 | 88.8 |
| Impurity (% w/w) | | | | | | | | | |
| RRT 0.30 | — | — | — | — | 0.14 | — | — | — | 0.15 |
| RRT 0.40 | 0.11 | 0.27 | 0.38 | 0.48 | 0.58 | 0.48 | 0.56 | 0.77 | 1.26 |
| RRT 0.46 | 0.22 | 0.21 | 0.23 | 0.24 | 0.26 | 0.24 | 0.27 | 0.32 | 0.34 |
| RRT 0.61 | — | — | — | 0.11 | 0.15 | 0.11 | 0.15 | 0.22 | 0.28 |

TABLE 38-continued

Chemical Stability of AE14B in Glass Vial (up to 8 W)

Product: Dronabinol AE14B Formulation in Glass Vial

| | Storage Condition | | | | | | | |
|---|---|---|---|---|---|---|---|---|
| | 5° C. | | | | 25° C./60% RH | | | |
| | Time Point | | | | | | | |
| Initial | 1 W | 2 W | 4 W | 8 W | 1 W | 2 W | 4 W | 8 W |

| | Initial | 1 W | 2 W | 4 W | 8 W | 1 W | 2 W | 4 W | 8 W |
|---|---|---|---|---|---|---|---|---|---|
| CBD | 0.15 | — | — | — | — | — | — | — | — |
| CBN | 0.57 | 0.54 | 0.59 | 0.62 | 0.60 | 0.63 | 0.72 | 0.83 | 0.95 |
| RRT 0.93 | 0.54 | 0.51 | 0.52 | 0.56 | 0.60 | 0.54 | 0.54 | 0.58 | 0.79 |
| Total | 1.6 | 1.5 | 1.7 | 2.0 | 2.2 | 2.0 | 2.2 | 2.7 | 3.6 |
| Impurity (% Area) | | | | | | | | | |
| RRT 0.30 | — | — | — | — | 0.17 | — | — | — | 0.16 |
| RRT 0.40 | — | 0.13 | 0.33 | 0.44 | 0.56 | 0.68 | 0.58 | 0.64 | 0.89 | 1.40 |
| RRT 0.46 | 0.26 | 0.26 | 0.27 | 0.28 | 0.30 | 0.29 | 0.31 | 0.37 | 0.38 |
| RRT 0.61 | — | — | — | 0.13 | 0.18 | 0.13 | 0.17 | 0.26 | 0.31 |
| CBD | 0.17 | — | — | — | — | — | — | — | — |
| CBN | 0.66 | 0.67 | 0.69 | 0.72 | 0.70 | 0.76 | 0.83 | 0.96 | 1.06 |
| RRT 0.93 | 0.63 | 0.63 | 0.61 | 0.65 | 0.71 | 0.64 | 0.62 | 0.66 | 0.87 |
| Total | 1.9 | 1.9 | 2.0 | 2.3 | 2.6 | 2.4 | 2.6 | 3.1 | 4.0 |

TABLE 39

Chemical Stability of AE14B in BFS Ampoule (up to 8 W)

Product: Dronabinol AE14B Formulation in BFS Ampoule

| | Storage Condition | | | | | | | |
|---|---|---|---|---|---|---|---|---|
| | 5° C. | | | | 25° C./60% RH | | | |
| | Time Point | | | | | | | |

| | Initial | 1 W | 2 W | 4 W | 8 W | 1 W | 2 W | 4 W | 8 W |
|---|---|---|---|---|---|---|---|---|---|
| Appearance | No phase separation | No phase separation | No phase separation | No phase separation | No phase separation | No phase separation | No phase separation | No phase separation | No phase separation |
| pH | 5.9 | 6.5 | 6.7 | 6.6 | 6.5 | 6.7 | 6.8 | 6.6 | 6.6 |
| Assay (% LC) | 87.5 | 82.2 | 88.4 | 81.9 | 85.4 | 86.4 | 83.6 | 76.3 | 85.8 |
| Impurity (% w/w) | | | | | | | | | |
| RRT 0.30 | — | — | — | — | 0.12 | — | — | — | 0.10 |
| RRT 0.40 | 0.11 | 0.26 | 0.37 | 0.47 | 0.63 | 0.39 | 0.53 | 0.70 | 0.73 |
| RRT 0.46 | 0.22 | 0.21 | 0.23 | 0.23 | 0.25 | 0.24 | 0.26 | 0.27 | 0.28 |
| RRT 0.61 | — | — | — | 0.14 | 0.12 | 0.12 | 0.14 | 0.18 | 0.13 |
| CBD | 0.16 | — | — | — | — | — | — | — | — |
| CBN | 0.56 | 0.53 | 0.60 | 0.56 | 0.59 | 0.62 | 0.68 | 0.69 | 0.79 |
| RRT 0.93 | 0.52 | 0.51 | 0.53 | 0.49 | 0.63 | 0.52 | 0.51 | 0.47 | 0.73 |
| Total | 1.6 | 1.5 | 1.7 | 1.9 | 2.2 | 1.9 | 2.1 | 2.3 | 2.7 |
| Impurity (% Area) | | | | | | | | | |
| RRT 0.30 | — | — | — | — | 0.14 | — | — | — | 0.12 |
| RRT 0.40 | 0.12 | 0.33 | 0.43 | 0.57 | 0.74 | 0.47 | 0.64 | 0.91 | 0.85 |
| RRT 0.46 | 0.26 | 0.26 | 0.26 | 0.29 | 0.29 | 0.29 | 0.32 | 0.36 | 0.33 |
| RRT 0.61 | — | — | — | 0.17 | 0.14 | 0.14 | 0.17 | 0.23 | 0.15 |
| CBD | 0.18 | — | — | — | — | — | — | — | — |
| CBN | 0.66 | 0.66 | 0.70 | 0.69 | 0.69 | 0.73 | 0.83 | 0.90 | 0.93 |
| RRT 0.93 | 0.61 | 0.63 | 0.61 | 0.61 | 0.73 | 0.61 | 0.62 | 0.61 | 0.85 |
| Total | 1.8 | 1.9 | 2.0 | 2.3 | 2.6 | 2.2 | 2.6 | 3.0 | 3.1 |

In this example, the growing trend of impurities continued the pattern observed by week 4 (4W). Assay of the BFS Ampoule at 25° C./60% RH increased back to near the initial value. This indicates that assay decrease seen by week 4 caused by adsorption on LDPE resin may not occur. As the forced degradation study showed, light exposure could cause fast degradation of the API. Therefore, the assay decrease at 4W could have been a result of light exposure during sample preparation, as no light protection during sample preparation was used before the forced degradation study.

In Examples 34-44, preparation and characterization of an emulsion composition of the invention (e.g., formulation AE10C) were explored.

Example 34: Preparation of Emulsion Composition (AE10C) without Pemulen

In this experiment, a microfluidizer process study of AE10C Trial #1 was carried out. An active batch of the sample was made using the microfluidizer. The process was carried out under ambient air according to the following protocol.

Container #1: The AE10C premix was prepared by adding ~85 g water for injection to container #1 while purging under nitrogen and stirring until $O_2$<5 ppm was achieved. Tween 80 (2 g) was added while stirring in an ice bath, followed by addition of 1.03 g (THC) under yellow light, 2.25 glycerin, and 0.97 g sesame oil. Homogenization was carried out at 5000 rpm for 2 min under ambient light (using a container covered with aluminum foil). Under yellow light, the pH was adjusted to pH 7 in an ice bath. The sample was q.s.'d to 100 g. Under ambient light (using a reservoir covered with aluminum foil) the sample was then microfluidized at 20 kpsi (5 passes) while the product outlet coil was cooled at 5° C.

Container #2: AE10C was collected in bulk in container #2.

The sample tests performed on AE10C Trial #1 are shown in Table 40.

Figure 12A:
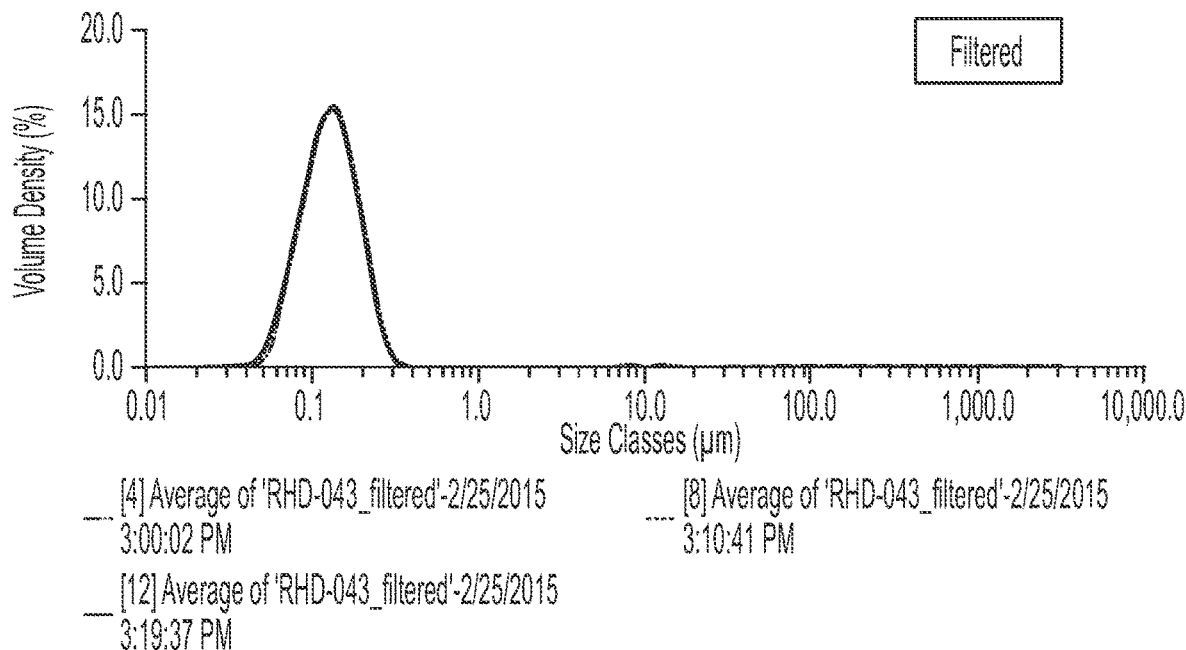
FIG. 12 shows a representative particle size distribution plot of AE10C samples described in Example 35. Results for the filtered sample are shown in (A). Results for the unfiltered sample are shown in (B).
Figure 12B:
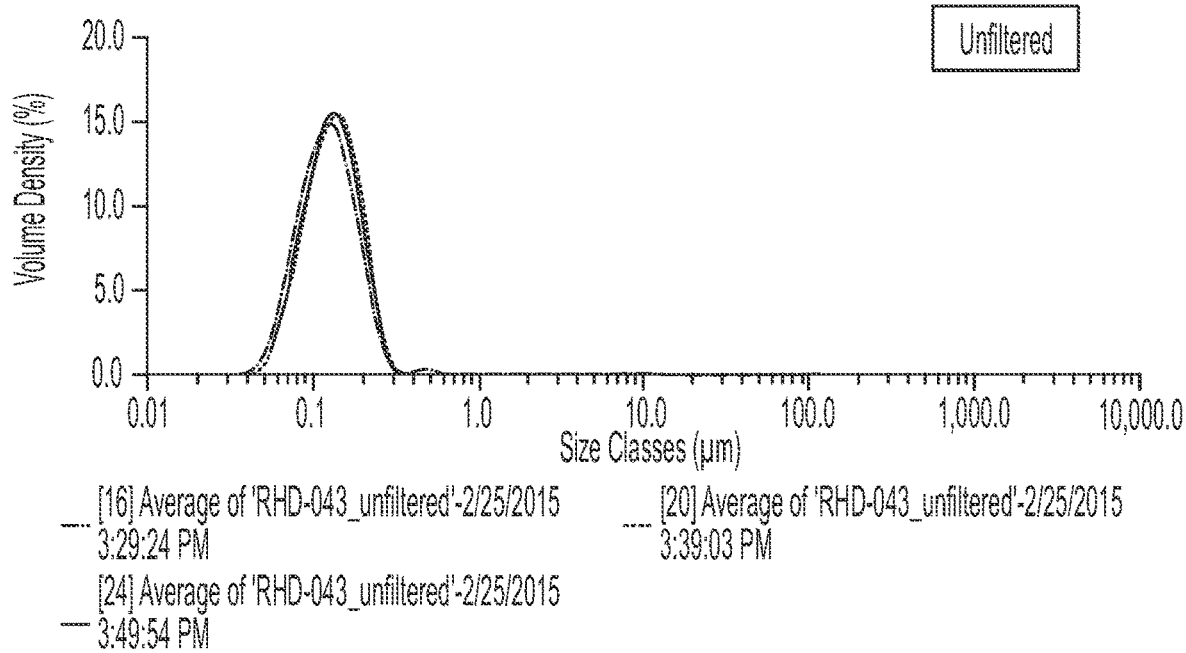

The filtered and unfiltered samples from AE10C Trial Batch #1 were tested with 3 repeats each. The PSD results are shown in FIG. 12 and Table 41. FIG. 12(A) shows results for the filtered sample. FIG. 12(B) shows results for the unfiltered sample.

TABLE 41

PSD Results AE10C Trial #1 Samples

| Sample Info | Measurement # in FIG. 12 | PSD (um) D10 | D50 | D90 | D99 |
|---|---|---|---|---|---|
| AE10C Trial #1, Filtered | 4 | 0.0792 | 0.129 | 0.205 | 0.291 |
|  | 8 | 0.0775 | 0.127 | 0.200 | 0.264 |
|  | 12 | 0.0753 | 0.125 | 0.198 | 0.263 |
| AE10C Trial #1, Unfiltered | 16 | 0.0738 | 0.123 | 0.200 | 0.428 |
|  | 20 | 0.0811 | 0.134 | 0.211 | 0.274 |
|  | 24 | 0.0789 | 0.129 | 0.204 | 0.268 |

The PSD method was judged to be suitable to test stability of the samples. The filtered and unfiltered AE10C formulation showed similar PSD, confirming that 20 kpsi process pressure is sufficient.

TABLE 40

Samples for AE10C Trial #1

| Sample | Sample Info | Tests | Purpose |
|---|---|---|---|
| In-Process Sample A | "Initial" state of the formulation | assay, impurities | — |
| In-Process Sample B | Formulation before Micro-Fluidizing | assay, impurities | To evaluate the effects of the Micro-Fluidizing process |
| Finished product | Formulation after Micro-Fluidizing | appearance, pH, assay, impurities, osmolarity | To evaluate the effects of the Micro-Fluidizing process |
| Filtered finished product | Product filtered through 0.2 um filter | assay, impurities, PSD | To evaluate retention of API by 0.2 um filter |
| Product filled in amber glass vial | 5 mL/vial, $N_2$ purged. | pH, assay, impurities, PSD; T0, 1 W, 2 W, 4 W, 8 W under 5 C and 25/60 | To evaluate stability of AE10C formulation |
| Product filled in PP ampoule | [1]0.5 mL/ampoule stored in $N_2$ purged glass vial, wrapped in aluminum foil. | pH, assay, impurities; 4 W, 8 W under 25/60 | To evaluate compatibility of API with PP |
| Product filled in LDPE ampoule | 0.5 mL/ampoule, $N_2$ purged, $O_2$ absorber in aluminum pouch | pH, assay, impurities; 4 W, 8 W under 25/60 | To evaluate compatibility of API with LDPE |
| Product filled in HDPE ampoule | [2]3 mL/ampoule, $N_2$ purged, $O_2$ absorber in aluminum pouch | pH, assay, impurities; 4 W, 8 W under 25/60 | To evaluate compatibility of API with HDPE |

[1]The PP ampoules cannot be closed by the heat sealer; therefore, each ampoule was placed in a nitrogen purged glass vial in an upright position. The glass vials were wrapped with aluminum foil to avoid light exposure.
[2]HDPE ampoule samples provide by HoloPack are 5 mL size.

Example 35: Particle Size Distribution of Emulsion Composition (AE10C)

In this example, PSD measurements for AE10C batch #1 sample prepared in Example 34 were collected. The sample method was reproducible. Noise shown in the measurements appears randomly and slightly skews the data, especially when using small amounts of sample due to limited sample amount. However, the characteristics of PSD can be easily determined using PSD graph and D10, D50, D90 numbers.

Example 36: Chemical Analysis of Emulsion Composition (AE10C)

The testing results for the AE10C Trial #1 in-process sample and finished product are presented in Table 42. In Table 42, in-process samples A and B were taken before microfluidizing, therefore phase separation and large variation in assay was expected as the formulation was not completely emulsified.

TABLE 42

PSD Results AE10C Trial #1 Samples

Product Dronabinol AE10C Formulation Sample

|  | API | In-process Sample A | In-process Sample B | Filtered Product | Unfiltered Product |
|---|---|---|---|---|---|
| Appearance | N/A | Phase separation | Phase separation | No phase separation | No phase separation |
| pH | N/A | 6.3 | 7.1 | 7.2 | 7.2 |
| Osmolarity | N/A | 300 | 266 | 266 | 288 |
| Assay (% LC) | 87.2 | 53.0 | 74.4 | 73.1 | 73.4 |
| Impurity (% w/w) | | | | | |
| [2]RRT 0.30 | — | 0.19 | 0.14 | 0.17 | 0.16 |
| [3]RRT 0.40 | — | 0.44 | 0.30 | 0.22 | 0.21 |
| [2,3]RRT 0.46 | 0.17 | 0.21 | 0.39 | 0.20 | 0.19 |
| [2]RRT 0.52 | — | — | 0.51 | — | — |
| [3]RRT 0.61 | — | — | 0.27 | 0.11 | 0.12 |
| [2]CBD | — | — | 0.55 | 0.38 | 0.36 |
| [2]RRT 0.70 | — | — | 0.59 | — | — |
| [2,3]CBN | 0.55 | 0.36 | 0.48 | 0.44 | 0.44 |
| RRT 0.93 | 0.46 | 0.31 | 0.40 | 0.36 | 0.37 |
| Total | 1.2 | 1.5 | 3.6 | 1.9 | 1.9 |
| Impurity (% Area) | | | | | |
| [2]RRT 0.30 | — | 0.32 | 0.17 | 0.22 | 0.21 |
| [3]RRT 0.40 | — | 0.73 | 0.36 | 0.29 | 0.27 |
| [2,3]RRT 0.46 | 0.19 | 0.35 | 0.47 | 0.26 | 0.25 |
| [2]RRT 0.52 | — | — | 0.61 | — | — |
| [3]RRT 0.61 | — | — | 0.33 | 0.15 | 0.15 |
| [2]CBD | 0.62 | — | 0.66 | 0.49 | 0.46 |
| [2]RRT 0.70 | 0.52 | — | 0.71 | — | — |
| 2,3CBN | — | 0.60 | 0.58 | 0.57 | 0.56 |
| RRT 0.93 | — | 0.52 | 0.48 | 0.46 | 0.48 |
| Total | 1.3 | 2.5 | 4.4 | 2.4 | 2.4 |

[2]Impurities generated by thermal stress.
[3]Impurities generated by photolytic stress The assay was found to be low, likely due to dilution in the microfluidizing process. The microfluidizer process generated more impurities than homogenization (1.6% w/w or 1.8% area). In-process sample B had higher impurities than the finished product. Assay of the filtered and unfiltered product was the same, indicating no retention of API on the filter.

Example 37: Stability Analysis of Emulsion Composition (AE10C)

In this example, stability results for AE10C Trial #1 were obtained for samples stored over a 2-week period. The testing results of samples from AE10C Trial Batch #1 are presented in the table below.

TABLE 43

AE10C Trial #1 stability results (up to 2 W)

Product Dronabinol AE10C Trial #1 (Amber Glass Vial)

Storage Condition

| | 5° C. | | | 25° C./60% RH | |
|---|---|---|---|---|---|
| Time Point | | | | | |
| | Initial | 1 W | 2 W | 1 W | 2 W |
| Appearance | | | | | |
| | No phase separation | No phase separation | No phase separation | No phase separation | No phase separation |
| pH | 7.2 | 6.9 | 6.9 | 7.0 | 6.8 |
| Assay (% LC) | 73.4 | 73.7 | 72.6 | 70.8 | 71.2 |
| Impurity (% w/w) | | | | | |
| RRT 0.25 | — | — | — | — | 0.13 |
| RRT 0.30 | 0.16 | 0.19 | 0.24 | 0.13 | 0.13 |
| RRT 0.40 | 0.21 | 0.30 | 0.45 | 0.89 | 2.15 |
| RRT 0.46 | 0.19 | 0.22 | 0.27 | 0.36 | 0.61 |
| RRT 0.51 | — | — | 0.10 | 0.14 | 0.27 |
| RRT 0.56 | — | — | — | — | 0.10 |
| RRT 0.62 | 0.12 | 0.17 | 0.19 | 0.39 | 0.79 |
| CBD | 0.36 | 0.44 | 0.52 | 0.71 | 0.48 |
| RRT 0.70 | — | — | — | 0.18 | 0.33 |
| CBN | 0.44 | 0.46 | 0.49 | 0.63 | 0.90 |
| RRT 0.93 | 0.37 | 0.35 | 0.26 | 0.26 | 0.27 |
| Total | 1.9 | 2.1 | 2.5 | 3.7 | 6.2 |
| Impurity (% Area) | | | | | |
| RRT 0.25 | — | — | — | — | 0.17 |
| RRT 0.30 | 0.22 | 0.25 | 0.32 | 0.18 | 0.17 |
| RRT 0.40 | 0.29 | 0.40 | 0.59 | 1.20 | 2.77 |
| RRT 0.46 | 0.26 | 0.29 | 0.36 | 0.49 | 0.79 |
| RRT 0.51 | — | — | 0.13 | 0.19 | 0.34 |
| RRT 0.56 | — | — | — | — | 0.13 |
| RRT 0.62 | 0.16 | 0.23 | 0.25 | 0.52 | 1.02 |
| CBD | 0.49 | 0.58 | 0.69 | 0.96 | 0.62 |
| RRT 0.70 | — | — | — | 0.25 | 0.42 |
| CBN | 0.59 | 0.62 | 0.64 | 0.86 | 1.16 |
| RRT 0.93 | 0.50 | 0.46 | 0.35 | 0.35 | 0.35 |
| Total | 2.5 | 2.8 | 3.3 | 5.0 | 7.9 |

As shown by comparison of Table 38 to this data, AE10C appeared to be less stable than AE14B.

Example 38: Preparation of Emulsion Compositions with Antioxidant

In this example, six antioxidant batches were made according to the following process.

Container #1: The AE10C premix was prepared by adding ~85 g water for injection to container #1 while purging under Ar and stirring until O2<5 ppm was achieved. Tween 80 (2 g), glycerin (2.5 g), sodium thiosulfate (5.0 g) or sodium sulfite (0.2 g), and sesame oil (1.0 g) or sesame oil/BHT/BHA (100:3:3) were added while stirring in an ice bath, followed by addition of 1.0 g API (THC) in sesame oil under yellow light. Homogenization was carried out at 5000 rpm for 2 min under ambient light (using a container covered with aluminum foil). Under yellow light, the pH was adjusted to pH 7 in an ice bath. The sample was q.s.'d to 100 g. Under ambient light (using a reservoir covered with aluminum foil) the sample was then micro-fluidized at 20 kpsi (5 passes) while the product outlet coil was cooled at 5° C.

Container #2: AE10C was collected in bulk in container #2.

The formulation composition of the antioxidant batches is shown in Table 44. Each batch was filled in 5 mL amber glass vials with nitrogen overlay and sealed with rubber stoppers and aluminum crimp seals.

TABLE 44

Formulations for antioxidant study

| | Ingredient | AE10C-A (Control) | AE10C-B | AE10C-C | AE10C-D | AE10C-E | AE10C-F |
|---|---|---|---|---|---|---|---|
| | | Concentration % w/w | | | | | |
| Base Formulation | Tween 80 | 2.00 | 2.00 | 2.00 | 2.00 | 2.00 | 2.00 |
| | Sesame oil | 1.50 | 1.50 | 1.50 | 1.50 | 1.50 | 1.50 |
| | NaOH solution, 0.1N | pH 7.0 | pH 7.0 | pH 7.0 | pH 7.0 | pH 7.0 | pH 7.0 |
| | Glycerin | 2.50 | 2.50 | 2.50 | 2.50 | 2.50 | 2.50 |
| | Pemulen TR-2 | 0 | 0 | 0 | 0 | 0 | 0 |
| | Dronabinol | 0.50 | 0.50 | 0.50 | 0.50 | 0.50 | 0.50 |
| | WFI | q.s. 100 | q.s. 100 | q.s. 100 | q.s. 100 | q.s. 100 | q.s. 100 |
| Anti-oxidant | BHT/BHA | 0 | 0.03/0.03 | 0 | 0 | 0.03/0.03 | 0.03/0.03 |
| | Sodium Thiosulfate | 0 | 0 | 5.00 | 0 | 5.00 | 0 |
| | Sodium Sulfite | 0 | 0 | 0 | 0.20 | 0 | 0.20 |

The stability schedule for the antioxidant study is shown in Table 45.

TABLE 45

Stability schedule for antioxidant study

| Storage Condition | T 0 | 1 W | 2 W | 4 W | 8 W | 12 W | 6 M | 12 M | TBD |
|---|---|---|---|---|---|---|---|---|---|
| 5° C. | A | B | B | B | B | B | B | | B |
| 25° C./60% RH | | B | B | B | B | B | B | | B |

Test group A: 1 vial/batch; tests required: appearance, pH, osmolarity, assay/impurities, PSD.
Test group B: 1 vial/batch; tests required: appearance, pH, assay/impurities, PSD.

Example 39: Effects of Antioxidant on Emulsion Composition (AE10C) During Production In this example, the testing results for the antioxidant batches were collected. In-process samples were taken right before microfluidizing in order to study the impact of the process. Test results are given below, Sample Point "I" stands for "In-Process" and "F" for "Finished Product."

TABLE 46

Antioxidant batches in-process results

| | Product Dronabinol AE10C Antioxidant Batches | | | | | | | | | | |
|---|---|---|---|---|---|---|---|---|---|---|---|
| | Antioxidant | | | | | | | | | | |
| | A (Control) | | B (BHT/BHA) | | C (ST) | | D (SS) | | E (BB + ST) | | F (BB + SS) | |
| | Sample Point | | | | | | | | | | |
| | I | F | I | F | I | F | I | F | I | F | I | F |
| Assay (% LC) | 71.3 | 64.6 | 58.7 | 74.5 | 59.9 | 54.7 | 46.6 | 57.9 | 59.9 | 56.3 | 77.1 | 71.7 |
| Impurity (% w/w) | | | | | | | | | | | | |
| RRT 0.32 | 0.14 | 0.15 | — | — | — | — | — | — | — | — | — | — |
| RRT 0.38 | — | — | — | — | — | — | 1.99 | 4.14 | — | — | — | 0.10 |

TABLE 46-continued

Antioxidant batches in-process results

Product
Dronabinol AE10C Antioxidant Batches
Antioxidant

| | A (Control) | | B (BHT/BHA) | | C (ST) | | D (SS) | | E (BB + ST) | | F (BB + SS) | |
|---|---|---|---|---|---|---|---|---|---|---|---|---|
| Sample Point | | | | | | | | | | | | |
| | I | F | I | F | I | F | I | F | I | F | I | F |
| RRT 0.43 | 0.38 | 0.35 | 0.27 | 0.25 | — | — | 0.43 | 0.32 | 0.19 | 0.22 | 0.59 | 0.56 |
| RRT 0.49 | 0.24 | 0.21 | 0.21 | 0.21 | 0.13 | — | 0.82 | 0.73 | 0.11 | — | 0.84 | 0.73 |
| RRT 0.52 | — | — | — | — | 1.31 | 1.04 | 0.69 | 0.71 | 0.78 | 0.83 | 1.07 | 1.27 |
| RRT 0.59 | — | — | — | — | — | — | 0.86 | 0.82 | — | — | 1.08 | 0.93 |
| RRT 0.64 | 0.15 | 0.13 | 0.11 | 0.12 | — | — | 0.78 | 0.86 | 0.14 | — | 0.73 | 0.74 |
| CBD | 0.32 | 0.31 | 0.19 | 0.23 | — | — | — | — | — | — | 0.56 | 1.28 |
| RRT 0.73 | — | — | — | — | — | — | 0.40 | 0.48 | — | — | 1.48 | 1.47 |
| RRT 0.79 | — | — | — | — | — | — | 0.34 | 0.30 | — | — | 0.39 | 0.16 |
| RRT 0.82 | — | — | 2.10 | 3.00 | — | — | 0.23 | 0.20 | 2.91 | 2.97 | 1.74 | 0.22 |
| RRT 0.86 | — | — | — | — | — | — | 0.40 | 0.63 | — | — | — | — |
| CBN | 0.46 | 0.42 | 0.37 | 0.44 | 1.12 | 1.09 | — | — | 0.71 | 0.71 | 1.11 | 0.91 |
| RRT 0.93 | 0.34 | 0.31 | 0.35 | 0.43 | 0.45 | 0.44 | 1.59 | 2.18 | 0.62 | 0.57 | — | — |
| RRT 0.96 | — | — | — | — | — | — | 0.17 | 0.25 | — | — | 0.12 | 0.27 |
| Total | 2.0 | 1.9 | 3.6 | 4.7 | 3.0 | 2.6 | 8.7 | 11.6 | 5.5 | 5.3 | 9.7 | 8.6 |
| Impurity (% Area) | | | | | | | | | | | | |
| RRT 0.32 | 0.20 | 0.22 | — | — | — | — | — | — | — | — | — | — |
| RRT 0.38 | — | — | — | — | — | — | 3.70 | 6.02 | — | — | — | 0.13 |
| RRT 0.43 | 0.53 | 0.59 | 0.44 | 0.35 | — | — | 0.81 | 0.47 | 0.24 | 0.29 | 0.70 | 0.70 |
| RRT 0.49 | 0.33 | 0.34 | 0.35 | 0.29 | 0.17 | — | 1.53 | 1.07 | 0.14 | — | 1.00 | 0.92 |
| RRT 0.52 | — | 0.19 | — | 0.14 | 1.74 | 1.40 | 1.28 | 1.03 | 1.00 | 1.07 | 1.26 | 1.59 |
| RRT 0.59 | — | — | — | — | — | — | 1.60 | 1.19 | — | — | 1.28 | 1.17 |
| RRT 0.64 | 0.21 | 0.26 | 0.18 | 0.19 | — | — | 1.46 | 1.26 | 0.18 | — | 0.86 | 0.93 |
| CBD | 0.45 | 0.45 | 0.31 | 0.29 | — | — | — | — | — | — | 0.66 | 1.61 |
| RRT 0.73 | — | — | — | — | — | — | 0.74 | 0.70 | — | — | 1.75 | 1.85 |
| RRT 0.79 | — | — | — | — | — | — | 0.64 | 0.44 | — | — | 0.46 | 0.21 |
| RRT 0.82 | — | — | 3.42 | 3.81 | — | — | 0.43 | 0.29 | 3.71 | 3.79 | 2.05 | 0.27 |
| RRT 0.86 | — | — | — | — | — | — | 0.75 | 0.91 | — | — | — | — |
| CBN | 0.63 | 0.63 | 0.60 | 0.56 | 1.48 | 1.46 | — | — | 0.91 | 0.91 | 1.31 | 1.14 |
| RRT 0.93 | 0.47 | 0.47 | 0.57 | 0.52 | 0.60 | 0.59 | 2.96 | 3.17 | 0.79 | 0.73 | — | — |
| RRT 0.96 | — | — | — | — | — | — | 0.32 | 0.37 | — | — | 0.14 | 0.34 |
| Total | 2.8 | 3.1 | 5.9 | 6.2 | 4.0 | 3.5 | 16.2 | 16.9 | 7.0 | 6.8 | 11.5 | 10.9 |

In Table 46, the decreased assay in some formulations indicates that dilution was not controlled well during microfluidizer process. The difference between in-process sample and finished product may be due to an un-even distribution of API in the in-process samples. For each batch, there was not a large difference between the in-process sample and finished product in terms of impurities. This indicates the microfluidizing process (20 kpsi, 5 passes) did not cause significant API (THC) degradation.

All batches with anti-oxidants contained higher and more species of impurities compared to the control formulation. It is believed that some of the impurities came from the antioxidants. However, based on the fact some impurities exist in both control and antioxidant batches but are elevated in antioxidant batches (RRT 0.49, RRT 0.52, RRT 0.64, CNB, and RRT 0.93), it could be expected that the antioxidants do cause API degradation or react with API.

Example 40: pH Effects from Antioxidant-Containing Emulsion Composition (AE10C)

In this example, testing result data after 1 week of storage was collected. While all formulations' pH values were adjusted to 6.8-7.2 during compounding, formulations containing sodium thiosulfate showed increase of pH value after stability storage, and those containing sodium sulfite showed decrease of pH value. These results indicate the salts introduced instability of formulation pH value. If sodium thiosulfate or sodium sulfate is used in formulations, pH buffers may be helpful to stabilize the pH value. Formulations containing 5% sodium thiosulfate had high osmolarity. This was expected due to high concentration of sodium thiosulfate. If sodium thiosulfate is used in formulations, it may be helpful to adjust the formulation to achieve isotonicity. Among the 6 formulations, Formulation F showed a smaller impurity growth compared to the other 5 formulations.

Example 41: Microfluidizer Process Effects

In this example, a microfluidizing process dilution study was carried out. Purified water was used to purge the microfluidizer before processing every batch, and the product premix was added to the reservoir after water was drained from it. The premix was added after water was drained then two more strokes were run, in order to reduce dilution while preventing air to enter the pump. The start point of collecting the product was based on visual observation, namely when the liquid appeared milky white from the product outlet. Using this procedure, the dilution has been shown to be significant and largely variable in the antioxidant batches.

A dilution study was then carried out by visual observation. The microfluidizer was purged with purified water until water is drained from the reservoir. The microfluidizer was run for two additional strokes. 100 mL of a placebo premix (PE10C) was added into the reservoir.

Figure 13:
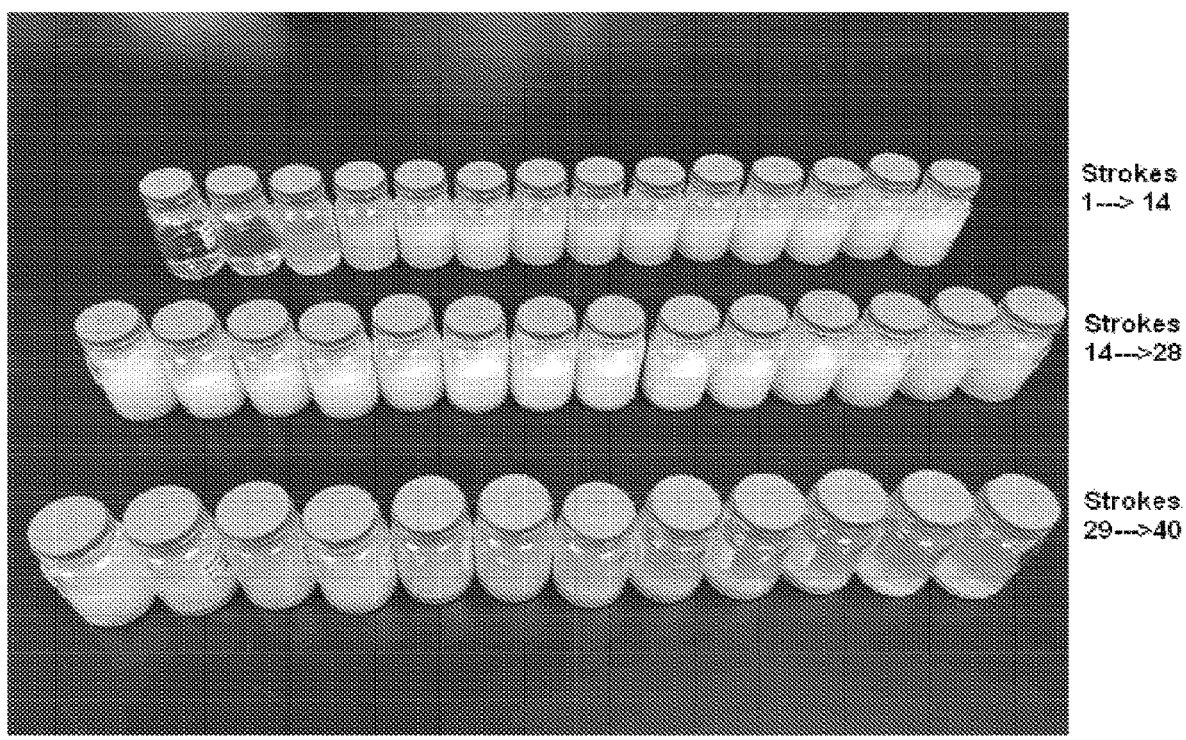
FIG. 13 is an image showing stroke samples obtained from a micro-fluidizer dilution experiment.

The processed liquid was collected from the product using 5 mL clear glass vials; one stroke is collected in each vial. The microfluidizer-processed placebo (1 stroke/vial) is shown in FIG. 13.

The change from diluted (Strokes #3) to concentrated (Strokes #19) is very gradual and it was difficult to determine the ideal start point to collect the product. The measured volume of each stroke is about 5.6 mL, and by visual observation Strokes #13-24 appear most concentrated. If these strokes are collected in an actual 100 mL batch, the yield is about 67% by volume. Visual evaluation may not be ideal to determine the best start point to collect product because the change is very gradual. Marker molecules (caffeine) may be used to determine the exact dilution of each stroke.

Example 42: Impurity Profiles of Antioxidants

In this example, an experiment was conducted to determine the impurity profile of the antioxidants. Three solutions: BHT/BHA in sesame oil, sodium thiosulfate in water, and sodium sulfite in water were made and tested using the analytical method for dronabinol product. The results are shown in Table 47. The impurity percentages were converted to levels corresponding to antioxidant concentrations in the dronabinol formulations.

TABLE 47

Antioxidant Impurity Testing Results Excipient Solutions

| Excipient | BHA/BHT (0.03% w/w) | Sodium Thiosulfate* (5.00% w/w) | Sodium Sulfite* (0.20% w/w) |
|---|---|---|---|
| Impurity (% w/w) | | | |
| RRT 0.30 | — | — | — |
| RRT 0.34 | — | — | — |
| RRT 0.36 | — | — | — |
| RRT 0.40 | — | — | — |
| RRT 0.46 | — | — | — |
| RRT 0.49 | — | — | — |
| RRT 0.51 | — | — | — |
| RRT 0.55 | — | — | — |
| RRT 0.62 | — | — | — |
| CBD | — | — | — |
| RRT 0.67 | — | — | — |
| RRT 0.70 | — | — | — |
| RRT 0.79 | — | — | — |
| RRT 0.82 | 2.96 | — | — |
| RRT 0.86 | — | — | — |
| CBN | — | — | — |
| RRT 0.93 | — | — | — |
| RRT 0.96 | — | — | — |
| Total | 2.96 | 0.0 | 0.0 |
| Impurity (% Area) | | | |
| RRT 0.30 | — | — | — |
| RRT 0.34 | — | — | — |
| RRT 0.36 | — | — | — |
| RRT 0.40 | 0.06 | — | — |
| RRT 0.46 | 0.87 | — | — |
| RRT 0.49 | — | — | — |
| RRT 0.51 | 0.05 | — | — |
| RRT 0.55 | — | — | — |

TABLE 47-continued

Antioxidant Impurity Testing Results Excipient Solutions

| Excipient | BHA/BHT (0.03% w/w) | Sodium Thiosulfate* (5.00% w/w) | Sodium Sulfite* (0.20% w/w) |
|---|---|---|---|
| RRT 0.62 | 0.09 | — | — |
| CBD | — | — | — |
| RRT 0.67 | — | — | — |
| RRT 0.70 | — | — | — |
| RRT 0.79 | — | — | — |
| RRT 0.82 | 98.76 | — | — |
| RRT 0.86 | — | — | — |
| CBN | — | — | — |
| RRT 0.93 | — | — | — |
| RRT 0.96 | — | — | — |
| Total | 99.8 | 0.0 | 0.0 |

As shown in Table 47, RRT 0.82 appeared to be the only impurity introduced by an antioxidant, BHT/BHA. The level of RRT 0.82 in the mock solution containing 0.03% BHT/BHA also matches the level seen in previous test results of Formulations B and E, which both contain 0.03% BHT/BHA. Therefore, RRT 0.82 can be removed from Formulations B and E.

Formulation F, while containing 0.03% BHT/BHA, does not show RRT 0.82 at the same level as the mock solution. It is possible RRT 0.82 undergoes reactions in this formulation due to the existence of sodium sulfite; since the mechanism of the decreased RRT 0.82 is unknown, it remains in the data tables to show the trend in this impurity's level.

Sodium thiosulfate and sodium sulfite did not introduce new impurities. While it is possible this is a result of the two antioxidants' low solubility in the diluent used for the test, the same can be assumed for the sodium thiosulfate and sodium sulfite contained in the dronabinol formulations and should not be expected to add impurities either. Therefore, it can be concluded that none of the new impurities in the dronabinol formulations was from sodium thiosulfate or sodium sulfite.

Example 43: Antioxidant Stability

In this example, the stability results of antioxidant batches stored over a 2-week period was determined. In this experiment, impurity RRT 0.82 was removed from Formulations B and E, and PSD results (up to 1W) were added. All formulations showed essentially unchanged PSD, indicating physical stability. Formulations D and F (both containing sodium sulfite) showed more species of impurities as well as significantly higher impurity levels than the rest of the formulations. Formulation B (0.03% BHT/BHA) showed relatively stable pH and a small decrease in assay. The impurity profile is similar to Formulation A (control), and the levels are lower than A. Formulation C (5% sodium thiosulfate) and E (BHT/BHA and sodium thiosulfate) showed an increase in pH, and significant decrease in assay. The impurity profiles of C and E are similar to A and B; Formulation C has impurity levels lower than A but higher than B, while Formulation E has impurity levels lower than both A and B.

Although Formulations C and E showed impurity levels comparable to the control and Formulation B, the significant assay decrease indicates there may be degradants that are not detected by the method. Formulation B showed lower impurity than the control and was considered a promising formulation.

Example 44: Retention Study on Placebo Formulations in BFS Ampoules

In this example, a BFS ampoule retention study was carried out. In order to evaluate the retention of dronabinol formulations in LDPE BFS ampoules, a study was performed on two placebo formulations, PE14B (homogenized, containing Pemulen) and PE10C (microfluidized, with no Pemulen). Two fill volumes were studied: 0.5 mL and 0.2 mL.

The procedure used in this study was as follows:
Weigh an open, empty LDPE ampoule;
Fill the ampoule with 0.5 mL or 0.2 mL designated formulation and weigh the filled ampoule.
Revert the ampoule and squeeze out the content into a waste container, then weigh the empty ampoule.
Calculate the fill weight and retention weight: Fill Wt.=Wt of filled ampoule—Tare Wt; Ret. Wt.=Wt of emptied ampoule—Tare Wt.

The antioxidant impurity testing results are shown in Example 48.

TABLE 48

Antioxidant Impurity Testing Results

| | Formulation | | | | | | | |
|---|---|---|---|---|---|---|---|---|
| | PE14B | | | | PE10C | | | |
| | Fill Volume | | | | | | | |
| | 0.5 mL | | 0.2 mL | | 0.5 mL | | 0.2 mL | |
| Ampoule # | Fill Wt. (mg) | Ret. Wt. (mg) | Fill Wt. (mg) | Ret. Wt. (mg) | Fill Wt. (mg) | Ret. Wt. (mg) | Fill Wt. (mg) | Ret. Wt. (mg) |
| 1 | 508.36 | 291.36 | 208.26 | 81.06 | 510.72 | 33.83 | 209.27 | 52.99 |
| 2 | 506.05 | 305.26 | 206.40 | 33.74 | 504.75 | 29.20 | 208.62 | 49.05 |
| 3 | 502.40 | 57.94 | 210.41 | 59.50 | 512.16 | 27.67 | 204.36 | 37.06 |
| 4 | 502.74 | 71.19 | 210.03 | 83.27 | 507.07 | 26.25 | 210.68 | 39.03 |
| 5 | 506.01 | 113.23 | 203.73 | 51.64 | 508.43 | 49.51 | 216.26 | 25.74 |
| Average | 505.11 | 167.80 | 207.77 | 61.84 | 508.63 | 33.29 | 209.84 | 40.77 |
| St. Dev. | 2.51 | 120.98 | 2.76 | 20.78 | 2.93 | 9.50 | 4.29 | 10.73 |
| Drop Size | 25 mg | | | | 33 mg | | | |

The retention of PE14B is significant due to its high viscosity. Ampoules #1 and #2 had the bottom "bulb" filled with the formulation after a large force was used to squeeze the formulation out. The retention of PE14C is about the size of one drop.

In Examples 45, 46, 50 and 51, the process parameters of microfluidizer to make emulsion compositions of the invention (e.g., AE14C) were studied.

Example 45: Microfluidizer Process Effects on Steady State

In this example, a microfluidizer process dilution study was carried out. A placebo batch (PE10C placebo) containing caffeine was processed using the microfluidizer. 20 strokes were collected and analyzed for caffeine level in order to evaluate the dilution effect at each stroke. After the purified water used to purge the equipment has drained from the reservoir, two more strokes were processed into a waste container, and the placebo was added to the reservoir. The process was started again, and each stroke was collected in a numbered vial. 40 strokes were collected, and the 20 most opaque samples were analyzed.

The results of the dilution study are shown in Table 49.

TABLE 49

Stroke# vs. Dilution during Microfluidizing

| Sample | % LC Caffeine Found | % of Highest Conc. |
|---|---|---|
| Stroke 6 | 55.5 | 50.4 |
| Stroke 7 | 78.9 | 71.6 |
| Stroke 8 | 93.5 | 84.8 |
| Stroke 9 | 101.3 | 91.9 |
| Stroke 10 | 104.7 | 95.0 |
| Stroke 11 | 106.7 | 96.8 |
| Stroke 12 | 107.6 | 97.6 |
| Stroke 13 | 108.8 | 98.7 |
| Stroke 14 | 109.3 | 99.2 |
| Stroke 15 | 109.9 | 99.7 |
| Stroke 16 | 109.8 | 99.6 |
| Stroke 17 | 110.2 | 100.0 |
| Stroke 18 | 108.3 | 98.3 |
| Stroke 19 | 104.4 | 94.7 |
| Stroke 20 | 100.2 | 90.9 |
| Stroke 21 | 98.5 | 89.4 |
| Stroke 22 | 71.0 | 64.4 |
| Stroke 23 | 37.6 | 34.1 |

TABLE 49-continued

Stroke# vs. Dilution during Microfluidizing

| Sample | % LC Caffeine Found | % of Highest Conc. |
|---|---|---|
| Stroke 24 | 19.0 | 17.2 |
| Stroke 25 | 9.7 | 8.8 |

As shown in Table 49, stroke #17 has the highest concentration of caffeine. Using 90-110% of peak concentration as a criterion, strokes #9-20 qualify as collectable strokes (12 strokes total). Results from this study were not entirely consistent with the visual observations made before, which showed strokes 13-24 appeared most opaque; this may be a result of batch-to-batch variation, or poor correlation between opaqueness and actual concentration.

Example 46: Reproducibility of Microfluidizer Process

In this example, the batch-to-batch variation of the microfluidizer process was investigated. The storage fluid in the reservoir (IPA) was drained and the system was purged with purified water. Once purified water was drained from the reservoir, two more strokes were processed and stopped. The PE10C pre-mix was added to the reservoir and processing was commenced at 20 kpsi. The product was collected into vials numbered #1 to #25 and the samples were analyzed for caffeine concentration. The caffeine potency was calculated using the following formula: Caffeine Potency=(Caffeine concentration in sample)÷(Caffeine concentration in premix bulk).

The process was repeated 3 times. Results from this study (Exp. 2, 3, and 4) are presented together with the first Caffeine study (Exp. 1). Strokes with 90% potency or higher are marked in light grey; Strokes with 90% potency or higher in all 4 batches are marked in dark grey.

TABLE 50

Stroke# vs. Dilution during Microfluidizing

| Stroke# | % Caffeine Potency | | | |
|---|---|---|---|---|
| | Exp. 1 | Exp. 2 | Exp. 3 | Exp. 4 |
| 6 | 50.4 | | | |
| 7 | 71.6 | 65.5 | 83.2 | 70.5 |
| 8 | 84.8 | 79.8 | 90.0 | 82.6 |
| 9 | 91.9 | 86.6 | 92.4 | 87.7 |
| 10 | 95.0 | 90.5 | 94.1 | 90.3 |
| 11 | 96.8 | | | |
| 12 | 97.6 | | | |
| 13 | 98.7 | | | |
| 14 | 99.2 | | | |
| 15 | 99.7 | 98.0 | 95.4 | 94.6 |
| 16 | 99.6 | 97.3 | 94.8 | 94.1 |
| *17 | 100.0 | | | |
| 18 | 98.3 | | | |
| 19 | 94.7 | 98.6 | 92.8 | 91.8 |
| 20 | 90.9 | 98.3 | 89.7 | 90.0 |
| 21 | 89.4 | 97.7 | 89.4 | 88.8 |
| 22 | 64.4 | 95.6 | 88.4 | 86.9 |
| 23 | 34.1 | 87.3 | 65.0 | 78.9 |
| 24 | 17.2 | 59.5 | 34.3 | 55.7 |
| 25 | 8.8 | 32.0 | 18.0 | 35.7 |

*After the reservoir was emptied and two more strokes were processed, the process was paused here to add purified water to the reservoir.

Figure 14:
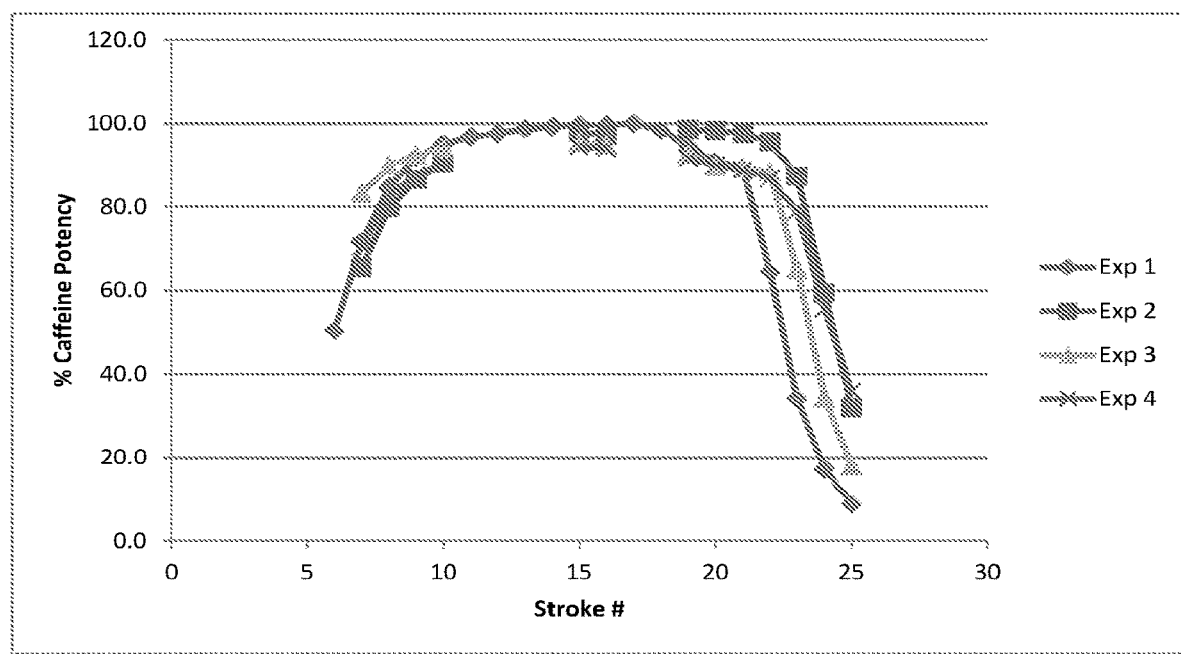
FIG. 14 is a plot of caffeine concentration in stroke samples obtained from a micro-fluidizer dilution experiment.

The data is presented graphically in FIG. 14.

With variation from batch to batch, strokes 11 to 13 meet the 90% potency criteria in each batch; the start and end of the qualifying strokes vary (marked in light grey in Table 50). Strokes with 90% or higher potency in all tested batches may be collected, e.g., Strokes #10-19 (marked in dark grey in Table 50). When processing a larger batch, the first 9 strokes should be discarded, and two more strokes should be collected after the reservoir is emptied of the premix. Collecting Strokes #10-19 results in a yield of about 56% in a 100 mL batch; the yield is higher when processing larger batches.

Example 47: A 4-Week Stability Study of Antioxidant-Containing Active Formulation In this example, stability of the antioxidant batches (Example 38; Table 44) at 4 weeks was examined. Formulations D and F (containing sodium sulfite) can be eliminated due to high impurities.

Assay of Formulations C and E (containing sodium thiosulfate) grew back to the initial level or even higher under both stability conditions. Formulations A and B were selected as prototypes for the animal study.

Example 48: BFS Container Compatibility Studies

In this example, BFS container compatibility experiments were carried out. Four types of containers were evaluated using formulation AE10C: 5 mL amber glass vial, 0.5 mL LDPE ampoule, 0.5 mL PP ampoule, and 5 mL HDPE ampoule. All samples were purged with nitrogen before sealing; glass vials were sealed with rubber stoppers and aluminum seals, and the BFS ampoules were sealed in aluminum pouches with nitrogen purge and oxygen scrubbers. The stability results are shown in Table 51.

TABLE 51

BFS container compatibility study results

Product
Dronabinol AE10C Formulation

| | Container | | | | | | | | |
|---|---|---|---|---|---|---|---|---|---|
| | Amber Glass Vial | | PP Ampoule | | LDPE Ampoule | | HDPE Ampoule | | |
| | Storage Condition | | | | | | | | |
| | 25° C./60% RH | | 25° C./60% RH | | 25° C./60% RH | | 25° C./60% RH | | |
| | Time Point | | | | | | | | |
| | Initial | 4 W | 8 W | 4 W | 8 W | 4 W | 8 W | 4 W | 8 W |
| Appearance | No phase separation | No phase separation | No phase separation | No phase separation | No phase separation | No phase separation | No phase separation | No phase separation | No phase separation |
| pH | 7.2 | 6.8 | 6.4 | 6.9 | 6.7 | 7.0 | 6.6 | 7.0 | 6.7 |
| Assay (% LC) | 73.4 | 63.4 | 62.4 | 63.7 | 64.0 | 65.9 | 70.9 | 69.1 | 71.2 |
| Impurity (% w/w) | | | | | | | | | |
| RRT 0.25 | — | — | — | — | — | — | — | — | — |
| RRT 0.30 | 0.16 | 0.16 | 0.15 | 0.16 | 0.16 | 0.10 | — | 0.11 | — |
| RRT 0.40 | 0.21 | 3.17 | 4.46 | 3.27 | 4.98 | 0.98 | 1.25 | 1.10 | 1.38 |
| RRT 0.46 | 0.19 | 1.04 | 1.27 | 1.01 | 1.23 | 0.33 | 0.36 | 0.34 | 0.36 |
| RRT 0.51 | — | 0.51 | 0.30 | 0.58 | 0.13 | 0.17 | 0.21 | 0.17 | — |
| RRT 0.52* | — | — | — | — | 0.31 | — | — | — | — |

TABLE 51-continued

BFS container compatibility study results

| | | Product Dronabinol AE10C Formulation | | | | | | | |
|---|---|---|---|---|---|---|---|---|---|
| | | \multicolumn{9}{c}{Container} | | | | | | | | |
| | | Amber Glass Vial | PP Ampoule | | LDPE Ampoule | | HDPE Ampoule | | |
| | | \multicolumn{9}{c}{Storage Condition} | | | | | | | | |
| | | 25° C./60% RH | 25° C./60% RH | | 25° C./60% RH | | 25° C./60% RH | | |
| | | \multicolumn{9}{c}{Time Point} | | | | | | | | |
| | Initial | 4 W | 8 W | 4 W | 8 W | 4 W | 8 W | 4 W | 8 W |
| RRT 0.56 | — | 0.20 | 0.17 | 0.16 | 0.16 | 0.10 | 0.18 | 0.11 | — |
| RRT 0.62 | 0.12 | 1.27 | 1.57 | 1.17 | 1.79 | 0.27 | 0.41 | 0.32 | 0.34 |
| CBD | 0.36 | 0.13 | 0.14 | — | — | — | — | — | — |
| RRT 0.70 | — | 0.34 | 0.26 | 0.13 | 0.09 | — | — | 0.10 | — |
| RRT 0.79 | — | 0.11 | 0.10 | — | — | — | — | — | — |
| CBN | 0.44 | 1.36 | 2.10 | 1.31 | 2.05 | 0.66 | 0.93 | 0.68 | 0.91 |
| RRT 0.93 | 0.37 | — | — | — | — | 0.37 | 0.35 | 0.39 | 0.37 |
| Total | 1.9 | 8.3 | 10.5 | 7.8 | 10.9 | 3.0 | 3.7 | 3.3 | 3.4 |
| | | \multicolumn{9}{c}{Impurity (% Area)} | | | | | | | | |
| RRT 0.25 | — | — | — | — | — | — | — | — | — |
| RRT 0.30 | 0.22 | 0.22 | 0.20 | 0.22 | 0.20 | 0.14 | — | 0.15 | — |
| RRT 0.40 | 0.29 | 4.40 | 5.94 | 4.54 | 6.41 | 1.40 | 1.63 | 1.54 | 1.79 |
| RRT 0.46 | 0.26 | 1.45 | 1.69 | 1.40 | 1.58 | 0.47 | 0.47 | 0.48 | 0.46 |
| RRT 0.51 | — | 0.71 | 0.40 | 0.81 | 0.17 | 0.25 | 0.28 | 0.24 | — |
| RRT 0.52* | — | — | — | — | 0.40 | — | — | — | — |
| RRT 0.56 | — | 0.28 | 0.22 | 0.23 | 0.21 | 0.15 | 0.23 | 0.15 | — |
| RRT 0.62 | 0.16 | 1.77 | 2.09 | 1.62 | 2.30 | 0.39 | 0.53 | 0.44 | 0.44 |
| CBD | 0.49 | 0.17 | 0.19 | — | — | — | — | — | — |
| RRT 0.70 | — | 0.47 | 0.35 | 0.18 | 0.12 | — | — | 0.13 | — |
| RRT 0.79 | — | 0.15 | 0.13 | — | — | — | — | — | — |
| CBN | 0.59 | 1.89 | 2.80 | 1.82 | 2.64 | 0.94 | 1.21 | 0.95 | 1.18 |
| RRT 0.93 | 0.50 | — | — | — | — | 0.52 | 0.45 | 0.55 | 0.48 |
| Total | 2.5 | 11.5 | 14.0 | 10.8 | 14.0 | 4.3 | 4.8 | 4.6 | 4.4 |

*New-peak integration/separation from Original RRT 0.51 (Shifted RRT 0.55)

As shown in Table 51, PP ampoules showed similar assay decrease and impurity increase as the amber glass vials. LDPE and HDPE ampoules showed similar assay and impurity profile; both appeared more stable than glass vials and PP ampoules. Because the PP ampoules could not be sealed with a heat sealer at the time of manufacturing, the ampoules were placed in glass vials standing up with nitrogen purge. This may have resulted in the high impurities, as the head space for the PP samples, similar to the amber glass vials, was much larger than LDPE and HDPE. In summary, LDPE and HDPE showed better stability than amber glass and PP; indicating compatibility with the formulation; however, the high impurities in amber glass and PP could have been a result of large headspace.

Example 49: Vitamin Effects

In this example, impurity profile data was collected for samples AE10C-G (containing Vitamin A acetate, 0.5% w/w) and AE10C-H (containing Vitamin E, 0.5% w/w). The amount of 50% Dronabinol added to these two batches was adjusted based on assay testing results (87% label claim); product collection during mirofluidizing followed the process described in Example 46.

The results of this experiment are shown in Table 52.

TABLE 52

AE10C-G and AE10C-H Test Results

| | Product | |
|---|---|---|
| | AE10C-G (Vitamin A Acetate) | AE10C-H (Vitamin E) |
| | Time Point | |
| | T0 | T0 |
| Appearance | No Phase separation | No Phase Separation |
| PH | 6.7 | 6.7 |
| Osmolarity (mOsm/L) | 306 | 304 |
| Assay (% LC) | 88.6 | 92.9 |
| | Impurity (% w/w) | |
| RRT 0.48 | 0.23 | 0.26 |
| RRT 0.52 | 0.12 | |
| RRT 0.58 | 0.16 | 0.10 |
| RRT 0.64 | 0.17 | 0.18 |
| RRT 0.66 | 0.46 | 0.54 |
| CBD | — | |

TABLE 52-continued

AE10C-G and AE10C-H Test Results

| | Product | |
|---|---|---|
| | AE10C-G (Vitamin A Acetate) | AE10C-H (Vitamin E) |
| | Time Point | |
| | T0 | T0 |
| CBN | 0.60 | 0.65 |
| RRT 0.93 | 0.41 | 0.38 |
| Total | 2.1 | 2.1 |
| Impurity (% Area) | | |
| RRT 0.48 | 0.25 | 0.27 |
| RRT 0.52 | 0.13 | |
| RRT 0.58 | 0.17 | 0.10 |
| RRT 0.64 | 0.18 | 0.19 |
| RRT 0.66 | 0.49 | 0.56 |
| CBD | — | |
| CBN | 0.64 | 0.67 |
| RRT 0.93 | 0.44 | 0.39 |
| Total | 2.3 | 2.2 |

*About 0.55% w/w or 0.51% Area of RRT 0.83 was detected in AE10C-G formulation. Because testing results of excipients showed that 0.5% Vitamin A resulted in about 0.5% w/w of RRT 0.83, it was determined this peak was from Vitamin A. Therefore, this peak was removed in the data table.

Adjusting the formulation based on API assay and following the improved microfluidizer process resulted in higher assay results. The initial impurity profiles of both formulations are similar to the other antioxidant formulations.

Example 50: Viscosity of Placebo Formulations (with or without Pemulen)

In this example, the viscosity of placebo formulations tested with and without Pemulen TR-2 was examined. Placebo samples containing Pemulen TR-2 (PE14B) and lacking Pemulen TR-2 (PE10C) were prepared and tested for viscosity as shown in Table 53.

TABLE 53

Viscosity of Placebo Formulations

| Sample Information | Viscosity (cP) |
|---|---|
| PE10C | 1.40 |
| PE14B | 277.1 |

As shown in Table 53, the formulation containing Pemulen TR-2 has higher viscosity, while the formulation without Pemulen TR-2 has viscosity close to that of water (1 cP at 20° C.).

Example 51: Verification of Microfluidizer Process

In this example, a microfluidizer process confirmation study was carried out. The process steps in this experiment are the same process steps used for the AE10C-G and AE10C-H stability batches. Specifically, the instrument reservoir was drained of purified water and two additional strokes were processed. 100 mL placebo PE10C premix (containing 0.2% caffeine) was added to the reservoir and processing was commenced at 20 kpsi. Processing involved re-circulation for 4 passes. The 5$^{th}$ pass was collected in a clean product container. Once the reservoir was drained two more strokes were processed and then stopped. Purified water was added to the reservoir and two more strokes were processed into the product container. The remaining product was discarded. The process confirmation study results are shown in Table 54.

TABLE 54

Process Confirmation Study Results

| Sample | % LC | % Potency | Yield |
|---|---|---|---|
| Caffeine Premix | 109.9 | 100.0 | — |
| Process Conformation Batch # 1 | 105.3 | 95.8 | 55.5% |
| Process Conformation Batch # 2 | 109.7 | 99.8 | 47.4% |
| Process Conformation Batch # 3 | 107.1 | 97.5 | 52.7% |

The designed process was able to generate product with potency within target range (90-110%). The yield of a 100 mL batch using this process is about 50%.

Example 52: Freeze Thaw Study on Emulsion Stability

In this example, a freeze-thaw study of a placebo formulation (PE10C) was carried out. Each cycle involving a freezing temperature (−20° C.) and two thawing temperatures (5° C. and 25° C.). The placebo was put through 3 freeze-thaw cycles as outlined in Table 55. At each time point, the product was observed for visual appearance, phase separation, and particle size distribution.

TABLE 55

Freeze-Thaw Cycle Schedule

| Cycle # | Session | Start Time (day/hr) | End Time (day/hr) | Testing Time (day/hr) |
|---|---|---|---|---|
| 1 | Freeze | 0 | 1/24 | 0 |
|   | Thaw | 1/24 | 2/48 | 2/48 |
| 2 | Freeze | 2/48 | 3/72 | — |
|   | Thaw | 3/72 | 4/96 | 4/96 |
| 3 | Freeze | 4/96 | 7/168 | — |
|   | Thaw | 7/168 | 8/192 | 8/192 |

The PSD results of this experiment are shown in Table 56.

TABLE 56

Freeze-Thaw Study Results (up to Cycle #2)

| Thawing Temp. | Cycle # | Phase Separation | PSD (μm) | | |
|---|---|---|---|---|---|
| | | | 10 | 50 | 90 |
| N/A | T0 | N | 0.07 | 0.12 | 0.20 |
| 5° C. | 1 | N | 0.08 | 0.13 | 0.21 |
|  | 2 | N | 0.08 | 0.13 | 0.20 |
|  | 3 | | | | |
| 25° C. | 1 | *N | 0.08 | 0.13 | 0.21 |
|  | 2 | N | 0.08 | 0.13 | 0.20 |
|  | 3 | | | | |

*No phase separation was observed at the end of thawing cycle #1, but small oil droplets were noted after the sample was stored at room temperature for 48 hours afterwards.

Figure 15:
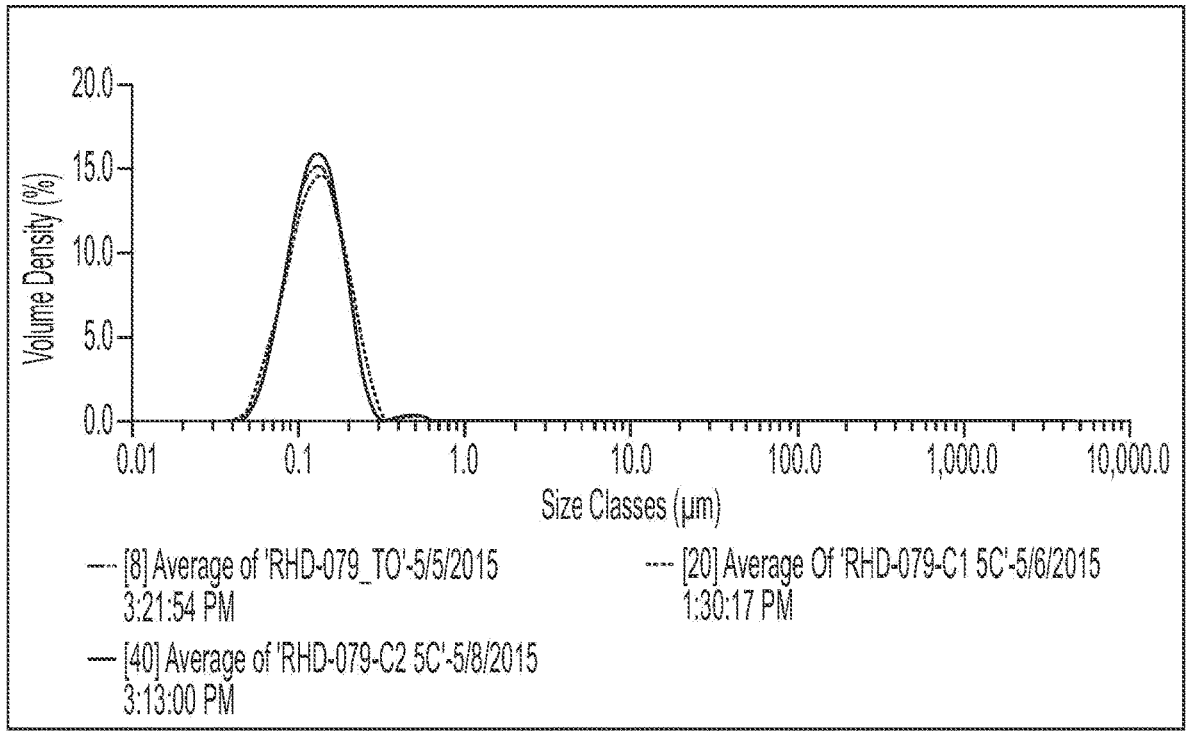
FIG. 15 shows a representative particle size distribution plot of samples described in Example 52. Samples were prepared at the 5° C. thawing condition described in the example.
Figure 16:
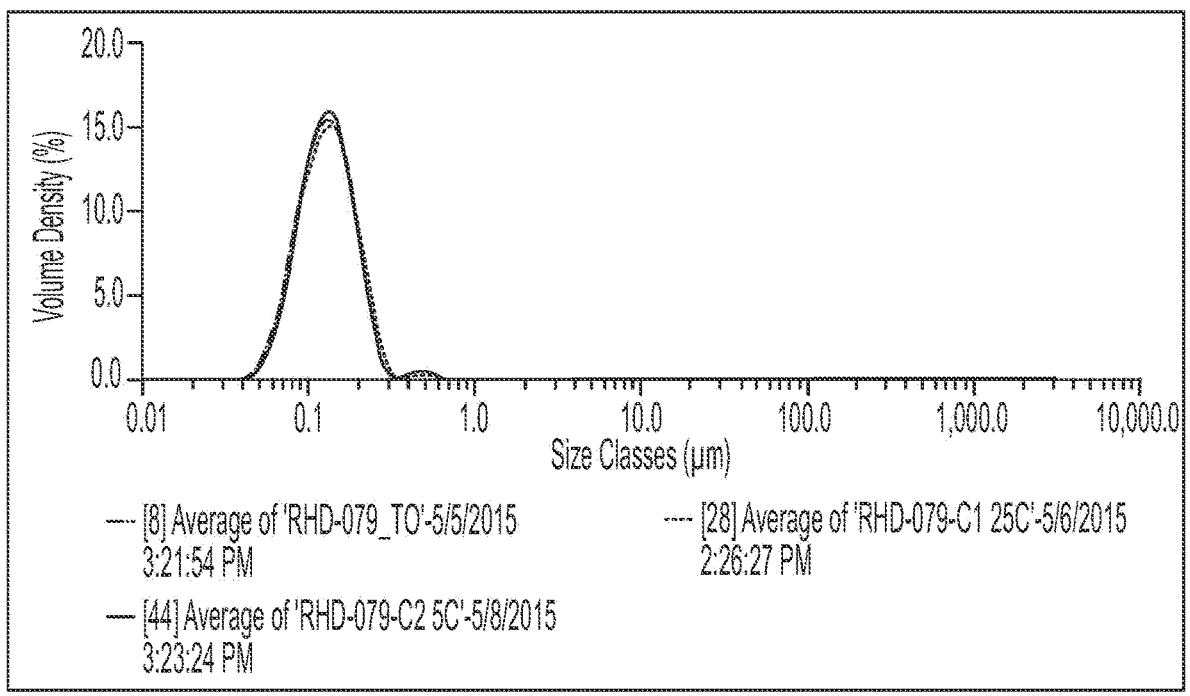
FIG. 16 shows a representative particle size distribution plot of samples described in Example 52. Samples were prepared at the 25° C. thawing condition described in the example.

PSD data of samples at the 5° C. thawing condition (up to cycle #2) are shown in FIG. 15. PSD data of samples at the 25° C. thawing condition (up to cycle #2) are shown in FIG. 16.

At the end of cycle #1 and cycle #2, samples at both thawing temperatures showed no phase separation or change in PSD. After storing at room temperature for 48 hours, the sample from 25° C., cycle #1 showed phase separation. This indicates the emulsion was de-stabilized at 25° C. thawing condition; although the phase separation occurred at a slow rate so that the 24 hours thawing time was not enough to physically show the separation.

Example 53: Repeating Freeze Thaw Study and Monitoring

In this experiment, the freeze-thaw study set forth in Example 52 was repeated. In this experiment, the PSD was tested immediately after completion of the thawing cycle.

TABLE 57

Freeze-Thaw Study Results
(tested immediately after completion of thawing cycle)

| Thawing Temp. | Cycle # | Phase Separation | PSD (µm) | | |
|---|---|---|---|---|---|
| | | | 10 | 50 | 90 |
| N/A | T0 | N | 0.0700 | 0.120 | 0.200 |
| 5° C. | 1 | *N | 0.0750 | 0.128 | 0.208 |
| | 2 | N | 0.0775 | 0.125 | 0.196 |
| | 3 | N | 0.0738 | 0.123 | 0.199 |
| 25° C. | 1 | **N | 0.0767 | 0.128 | 0.207 |
| | 2 | N | 0.0781 | 0.127 | 0.201 |
| | 3 | N | 0.0798 | 0.129 | 0.200 |

*No phase separation was observed at the end of thawing cycle #1, but small oil droplets were noted after the sample was stored at room temperature for 72 hours afterwards.
**No phase separation was observed at the end of thawing cycle #1, but small oil droplets were noted after the sample was stored at room temperature for 48 hours afterwards.

Figure 17:
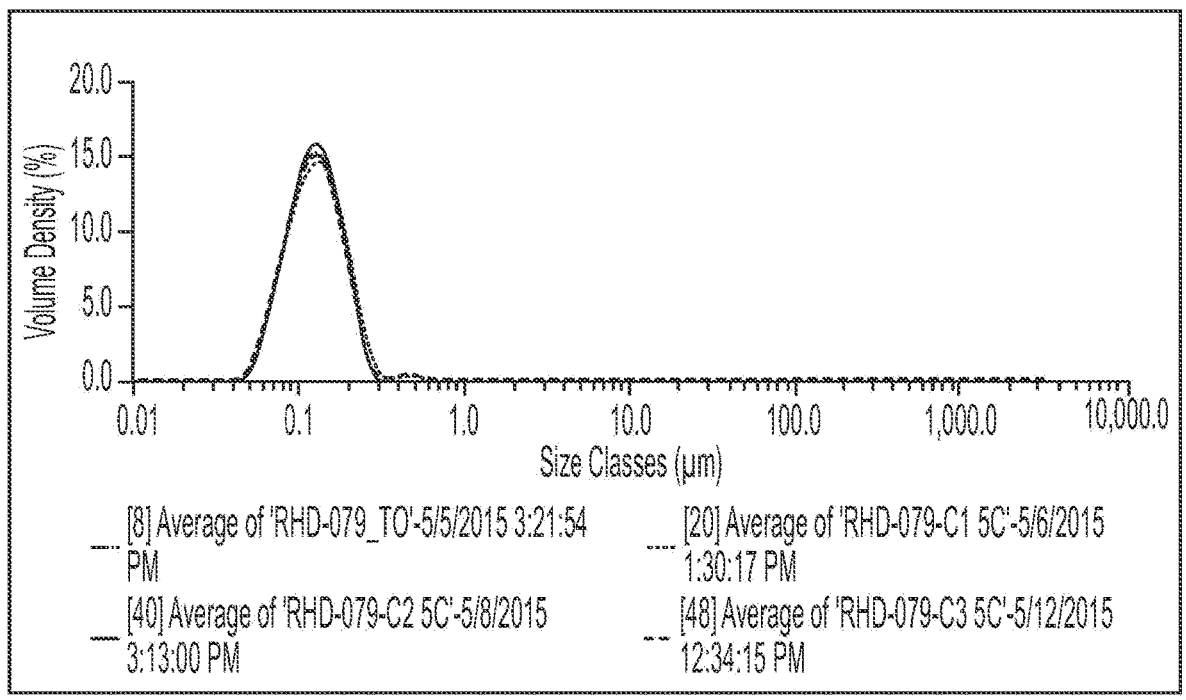
FIG. 17 shows a representative particle size distribution plot of samples described in Example 53. Samples were prepared at the 5° C. thawing condition described in the example.
Figure 18:
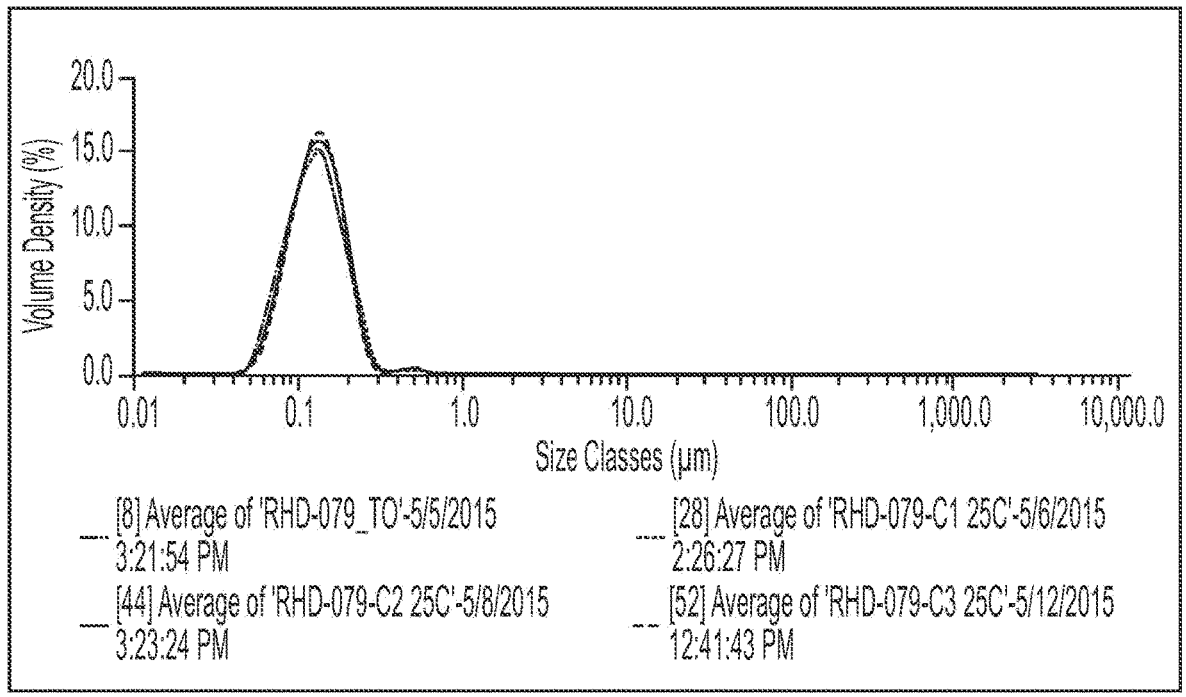
FIG. 18 shows a representative particle size distribution plot of samples described in Example 53. Samples were prepared at the 25° C. thawing condition described in the example.

The PSD of the samples at the 5° C. thawing condition (tested immediately after completion of thawing cycle) is shown in FIG. 17. The PSD of samples at the 25° C. thawing condition (tested immediately after completion of thawing cycle) is shown in FIG. 18.

In this experiment, no significant change was observed in PSD measurement. Samples at both thawing conditions showed no phase separation at the time of thawing completion. After storing at room temperature for a period of time post-thawing (48 hr for 25° C. sample and 72 hr for 5° C. sample), the cycle #1 samples from both thawing conditions showed phase separation. After storing at room temperature, cycle #2 and cycle #3 samples from both thawing conditions did not show phase separation. The samples that experienced more freeze-thaw cycles surprisingly showed better stability than samples that only underwent one cycle. All samples were monitored after the study was complete in order to observe possible phase separation in cycle #2 and cycle #3 samples, given sufficient time of storage at room temperature.

The samples were tested 10 days and 16 days after initiation of the study. The PSD data at day 10 is shown in Table 58.

TABLE 58

Freeze-Thaw Study Results (tested on Day 10)

| Testing Date | Thawing Temp. | Cycle # | Phase Separation | PSD (µm) | | |
|---|---|---|---|---|---|---|
| | | | | 10 | 50 | 90 |
| Day 10 | N/A | T0 | N | 0.0759 | 0.127 | 0.204 |
| | 5° C. | 1 | Y | 0.0752 | 0.126 | 0.205 |
| | | 2 | N | 0.0744 | 0.124 | 0.201 |
| | | 3 | N | 0.0752 | 0.127 | 0.206 |
| | 25° C. | 1 | Y | 0.0736 | 0.123 | 0.199 |
| | | 2 | N | 0.0749 | 0.125 | 0.203 |
| | | 3 | N | 0.0796 | 0.129 | 0.203 |
| Day 16 | N/A | T0 | N | 0.0742 | 0.122 | 0.195 |
| | 5° C. | 1 | Y | 0.0745 | 0.123 | 0.197 |
| | | 2 | N | 0.0776 | 0.127 | 0.200 |
| | | 3 | N | 0.0759 | 0.127 | 0.205 |
| | 25° C. | 1 | Y | 0.0744 | 0.123 | 0.198 |
| | | 2 | N | 0.0779 | 0.130 | 0.207 |
| | | 3 | N | 0.0756 | 0.127 | 0.206 |

Figure 19:
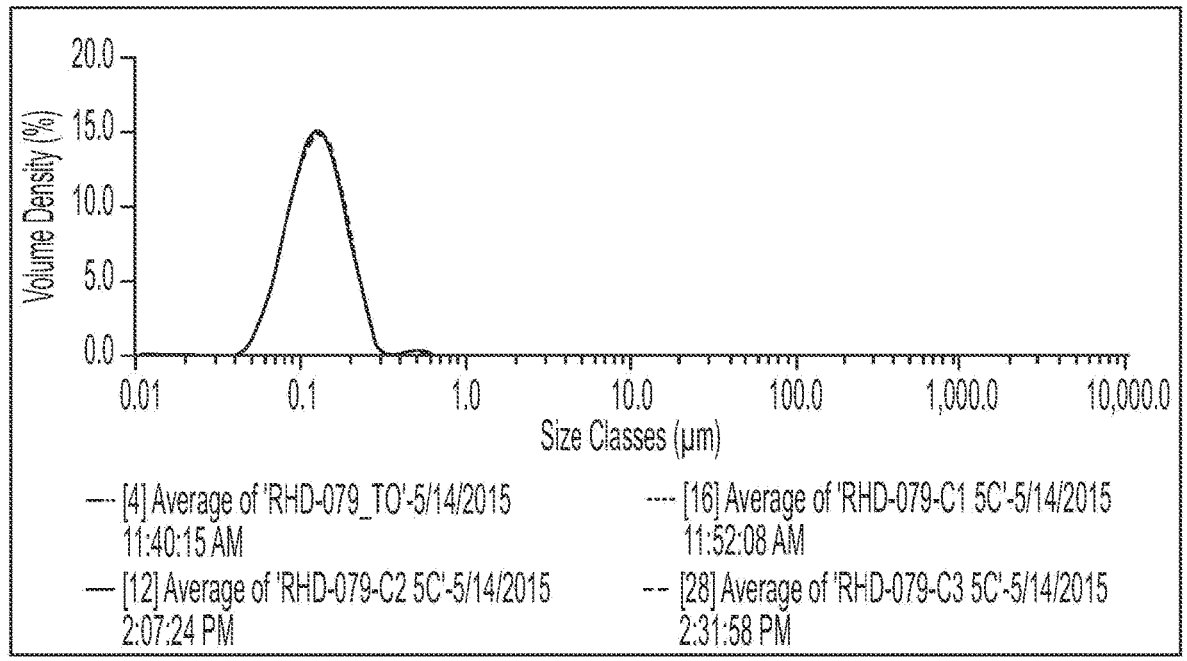
FIG. 19 shows a representative particle size distribution plot of samples described in Example 53. Samples were prepared at the 5° C. thawing condition (day 10) as described in the example.
Figure 20:
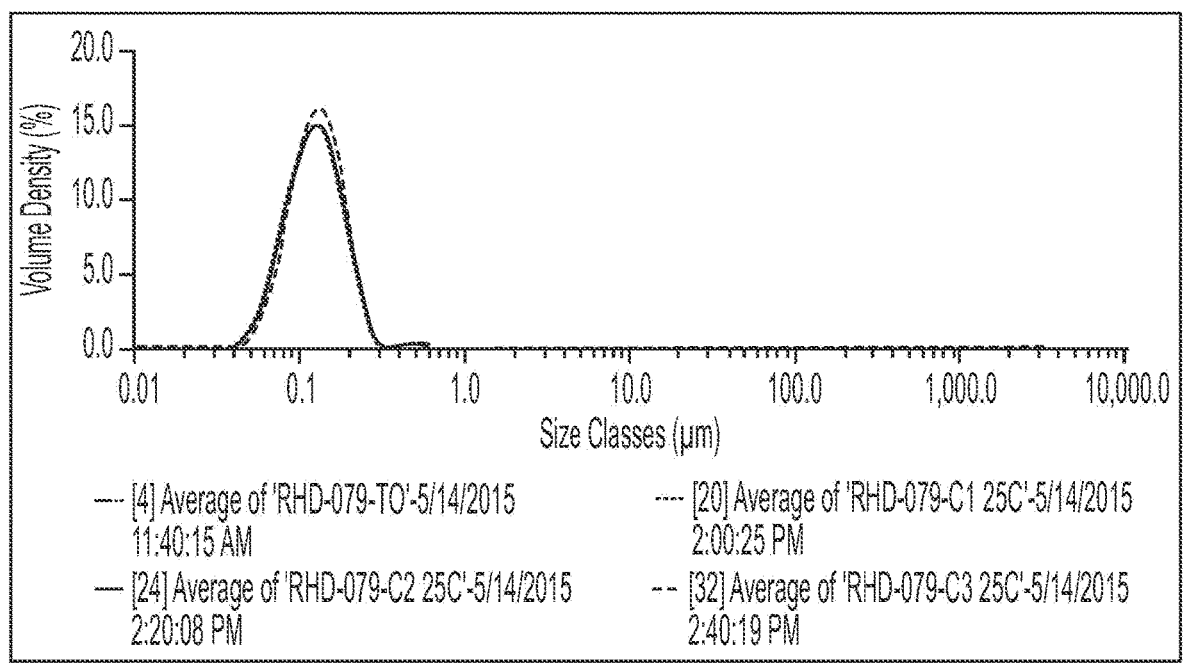
FIG. 20 shows a representative particle size distribution plot of samples described in Example 52. Samples were prepared at the 25° C. thawing condition (day 10) described in the example.
Figure 21:
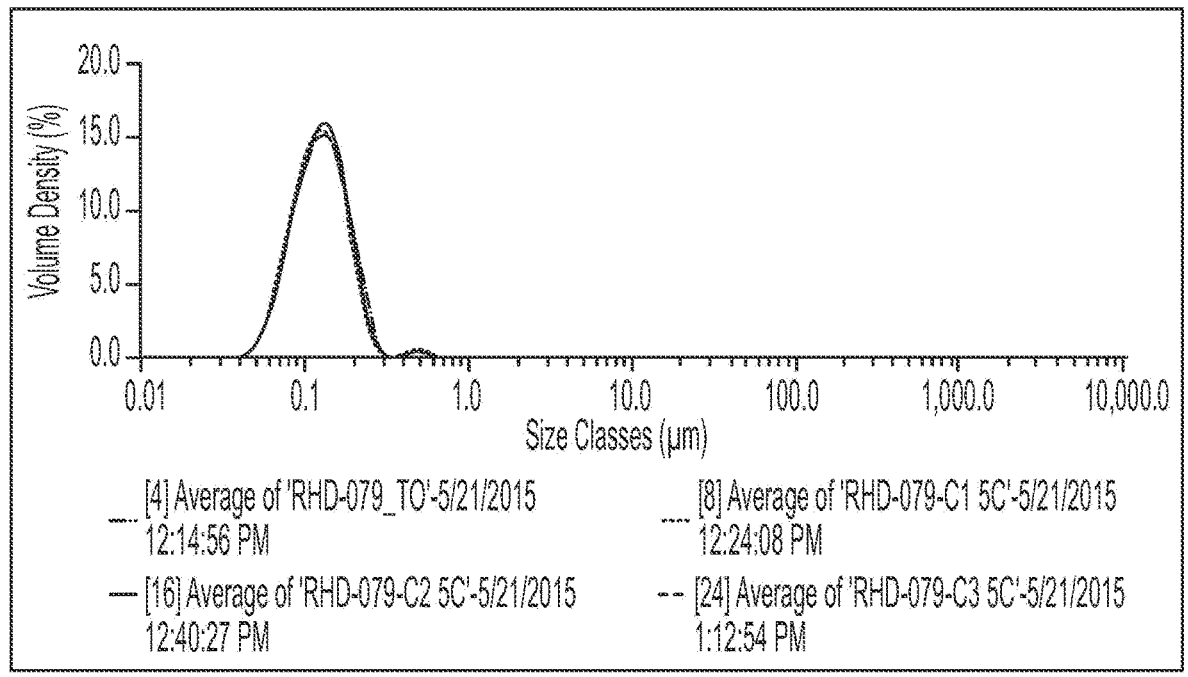
FIG. 21 shows a representative particle size distribution plot of samples described in Example 53. Samples were prepared at the 5° C. thawing condition (day 16) described in the example.
Figure 22:
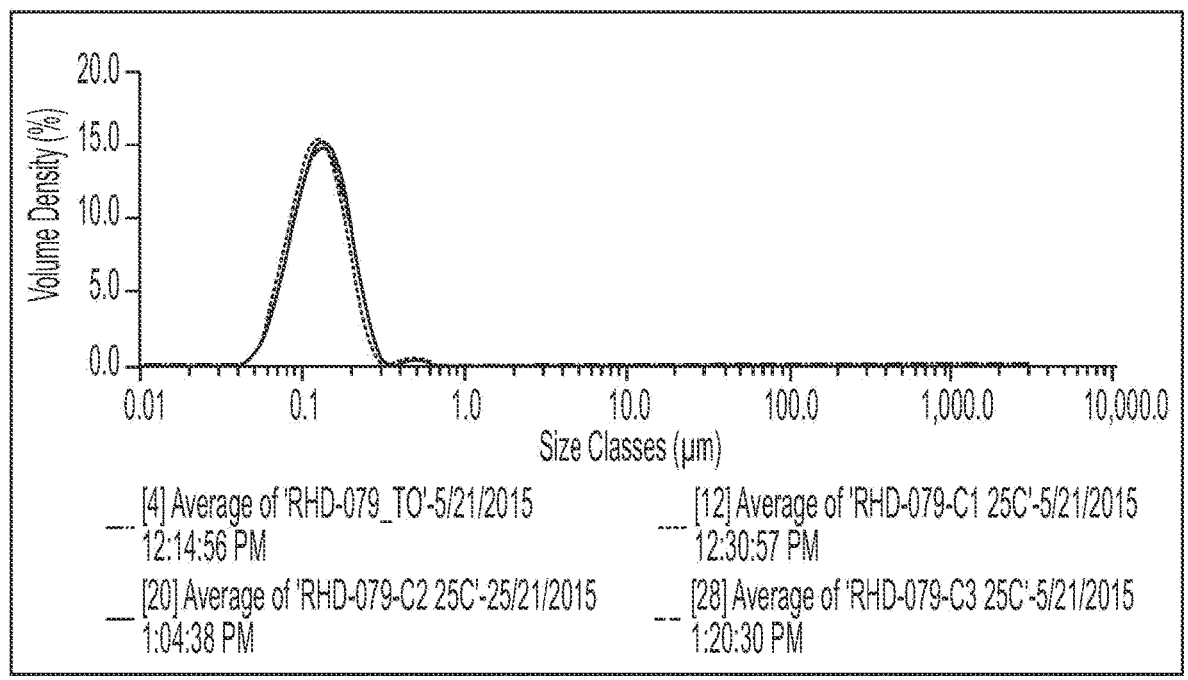
FIG. 22 shows a representative particle size distribution plot of samples described in Example 53. Samples were prepared at the 25° C. thawing condition (day 16) described in the example.
Figure 23:
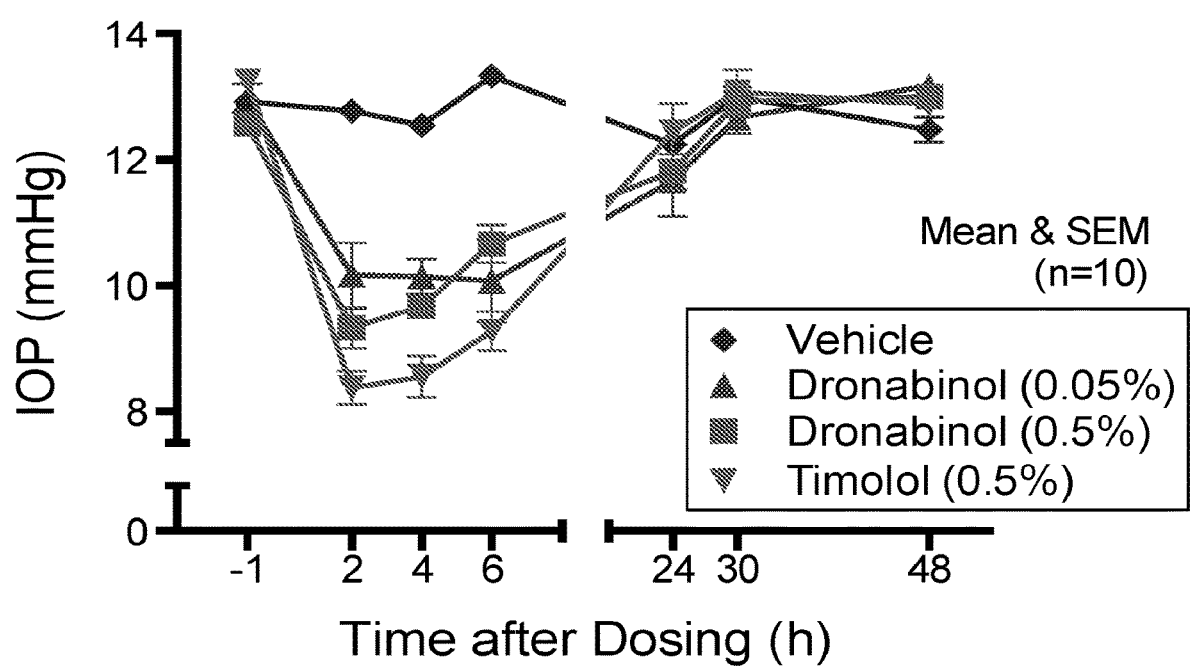
FIG. 23 is a plot showing the effects of Dronabinol and Timolol intraocular pressure in a mouse model.

PSD data of samples at the 5° C. thawing condition (tested on day 10) are shown in FIG. 19. PSD data of samples at the 25° C. thawing condition (tested on day 10) are shown in FIG. 20. PSD data of samples at the 5° C. thawing condition (tested on day 16) are shown in FIG. 21. PSD data of samples at the 25° C. thawing condition (tested on day 16) are shown in FIG. 22.

After storing at room temperature, cycle #1 samples were still the only samples showing phase separation. PSD of all samples did not show significant change after storing at room temperature.

The data presented above indicates that the emulsion product may be frozen at −20° C. for storage. Because the thawed samples showed phase separation 72 hours after being pulled from the freezer, it is recommended that when using frozen samples for animal studies, the sample is used within 48 hours after they are pulled from the frozen storage. The samples may be re-frozen and thawed for an additional 2 cycles if needed. The thawed samples should be used within 48 hours after being taken out of the frozen storage.

Example 54: Stability Monitoring of Antioxidant-Containing Formulations in 12 Weeks In this experiment, the stability of antioxidant formulations A and B (Table 44) were tested during a 12-week storage period. The samples showed good physical stability, as indicated by Particle Size Distribution and the lack of phase separation. The pH of both formulations was more stable at 5° C. and a decreasing trend is noted at 25° C./60% RH.

Formulation A (control) showed a steady increasing trend of total impurities, mostly driven by increase of RRT 0.40, 0.46, 0.62, and CBN. A similar trend was observed at 25° C./60% RH stability condition up to 8 weeks, however the 12-week sample showed a decrease of the aforementioned impurities, in addition to a decrease of RRT 0.70 and 0.79. An increase of assay in the 12-week samples at 25/60 condition was also noted. The mechanism of these changes is surprising and unexpected. Formulation B (BHT/BHA) showed a steady increase of total impurities at both stability conditions, mostly driven by increase of RRT 0.40, 0.46, 0.62, and CBN. Overall Formulation B demonstrated slightly better stability than Formulation A.

Example 55: Stability of Antioxidant-Containing Formulations

In this experiment, the stability of antioxidant formulations A, B, and G were tested during a 4-week storage period. The antioxidant formulations were prepared as described in Example 38 (Table 44). Formula G contains Vitamin A Acetate. The summary stability results for Formulations A, B, and G are shown in Table 59. Assay, pH, and % area impurities at T0 and 4W are shown for comparison.

TABLE 59

Summary of Assay and % Area Impurity data of Formulations A, B, & G

| | Storage Condition | | | | | | | | |
|---|---|---|---|---|---|---|---|---|---|
| | 5° C. | | | | | | 25° C./60% RH | | |
| | Time Point | | | | | | | | |
| | T0 | | | 4 W | | | 4 W | | |
| | Formulation | | | | | | | | |
| | A | B | G | A | B | G | A | B | G |
| pH | 7.0 | 7.0 | 6.7 | 6.9 | 7.2 | 6.3 | 6.8 | 6.7 | 5.2 |
| Assay (% LC) | 64.6 | 74.5 | 88.6 | 64.0 | 76.0 | 85.6 | 58.2 | 70.3 | 81.7 |
| Impurity (% Area) | | | | | | | | | |
| RRT 0.30 | 0.23 | — | — | 0.23 | — | 0.33 | 0.18 | 0.15 | 0.19 |
| RRT 0.34 | — | — | — | — | — | — | — | — | — |
| RRT 0.36 | — | — | — | — | — | — | — | — | — |
| RRT 0.40 | 0.52 | 0.32 | — | 1.09 | 0.76 | 1.06 | 4.59 | 1.86 | 1.75 |
| RRT 0.46 | 0.32 | 0.27 | — | 0.45 | 0.38 | 0.38 | 1.30 | 0.68 | 0.65 |
| RRT 0.49 | — | — | 0.25 | 0.23 | 0.22 | 0.08 | 0.71 | 0.34 | — |
| RRT 0.51 | — | — | 0.13 | — | — | — | — | — | — |
| RRT 0.55 | — | — | 0.17 | — | 0.11 | — | 0.23 | 0.16 | 0.13 |
| RRT 0.62 | 0.20 | 0.15 | 0.18 | 0.35 | 0.30 | 0.37 | 1.83 | 0.73 | 0.60 |
| CBD | 0.47 | 0.29 | 0.49 | 0.65 | 0.29 | 0.21 | — | 0.11 | — |
| RRT 0.67 | — | — | — | — | — | — | — | — | — |
| RRT 0.70 | — | — | — | 0.20 | 0.29 | 0.32 | 0.65 | 0.57 | — |
| RRT 0.79 | — | — | — | — | — | — | 0.15 | — | — |
| *RRT 0.82 | — | — | — | — | — | 0.73 | — | — | 0.54 |
| RRT 0.86 | — | — | — | — | — | — | — | — | — |
| CBN | 0.63 | 0.56 | 0.64 | 0.74 | 0.65 | 0.79 | 2.01 | 1.09 | 1.25 |
| RRT 0.93 | 0.47 | 0.55 | 0.44 | 0.26 | 0.34 | 0.44 | — | 0.41 | 0.57 |
| RRT 0.96 | — | — | — | — | — | — | — | — | — |
| Total | 2.8 | 2.1 | 2.3 | 4.2 | 3.3 | 4.7 | 11.7 | 6.1 | 5.7 |

*About 3% w/w or 3.8% Area of RRT 0.82 was detected in Formulation B. Because testing results of excipients showed that 0.03% BHT/BHA resulted in about 3% w/w of RRT 0.82, it was determined this peak was from BHT/BHA. Therefore, this peak was removed in the data table.
**About 0.55% w/w or 0.51% Area of RRT 0.83 was detected in Formulation G. Because testing results of excipients showed that 0.5% Vitamin A resulted in about 0.5% w/w of RRT 0.83, it was determined this peak was from Vitamin A. Therefore, this peak was removed in the data table.

The pH of Formulations A and B appears more stable than Formulation G. Both Formulation B (BHT/BHA) and Formulation G (Vitamin A Acetate) showed improved stability profile compared to the control Formulation A at accelerated condition 25° C./60% RH. Some impurities appeared to be higher in Formulation G compared to B, while the reverse is true for some other impurities, as marked in the data table. Total impurities in Formulation B was found to be lower than G at 5° C. The two formulations were found to be similar at the 25° C./60% RH condition. The major distinguishing characteristic between the Formula B and G results is the existence of RRT 0.82 in Formulation G. Since RRT0.82 was an impurity brought in by BHT and BHA in Formulation B and was excluded during data processing.

These data show that Formulations B and G possess improved stability at accelerated conditions; the impurity profiles at 5° C. showed Formulation B slightly better stability.

Example 56: Six- or Twelve-Month Stability of Active Formulation

In this experiment, the stability of samples of an active formulation (AE10C-B) (Table 44) were tested over a 6 month or 12-month period under various conditions. The data for the stability tests are shown in Tables 60-69. The data shown for week 8 is an outlier.

TABLE 60

Stability of Dronabinol Ophthalmic Emulsion AE10C-B Placebo at −20° C.

| | Testing Conditions | | | | | |
|---|---|---|---|---|---|---|
| | Initial | 4 W | 8 W | 12 W | 6 M | 12 M |
| Appearance | White opaque liquid, no phase separation | White opaque liquid, no phase separation | White opaque liquid, no phase separation | Off-white opaque liquid, no phase separation | White opaque liquid, no phase separation | Off-white opaque liquid, no phase separation |
| pH | 6.8 | 7.1 | 7.1 | 7.3 | 7.4 | 7.6 |
| Osmolarity | 295 mOsm/L | NA | NA | NA | 297 mOsm/L | 298 mOsm/L |
| THC Assay | 0.0% | 0.0% | 0.0% | 0.0% | 0.0% | 0.0% |
| Impurity | RRT 0.2:5.28%; RRT | RRT 0.2:5.65%; RRT | RRT 0.2:4.75%; RRT | RRT 0.2:5.49%; RRT | RRT 0.2:5.64%; RRT | RRT 0.2:5.22%; RRT |

TABLE 60-continued

Stability of Dronabinol Ophthalmic Emulsion AE10C-B Placebo at −20° C.

| | Testing Conditions | | | | | |
|---|---|---|---|---|---|---|
| | Initial | 4 W | 8 W | 12 W | 6 M | 12 M |
| | 0.81:3.49% RRT | 0.81:3.69% RRT | 0.81:3.13% RRT | 0.81:3.63% RRT | 0.81:3.69% RRT | 0.81:3.32% RRT |
| | 1.22:0.51% RRT | 1.22:0.46% RRT | 1.22:0.46% RRT | 1.22:0.56% RRT | 1.22:0.66% RRT | 1.22:0.59% RRT |
| | 1.27:1.77% RRT | 1.27:1.95% RRT | 1.27:1.59% RRT | 1.27:1.98% RRT | 1.27:1.93% RRT | 1.27:2.17% RRT |
| | 1.35:1.96% Total: 13.0% | 1.35:2.16% Total: 13.9% | 1.35:1.81% Total: 11.7% | 1.35:2.47% RRT 1.40:0.27% Total: 14.4% | 1.35:2.46% RRT 1.40:0.22% Total: 14.6% | 1.35:2.43% RRT 1.40:0.18% Total: 13.9% |
| PSD | D10: 0.0785 D50: 0.133 D90: 0.216 D99: 0.306 | D10: 0.0799 D50: 0.134 D90: 0.214 D99: 0.289 | D10: 0.0838 D50: 0.138 D90: 0.215 D99: 0.278 | D10: 0.0772 D50: 0.129 D90: 0.208 D99: 0.275 | D10: 0.0796 D50: 0.133 D90: 0.212 D99: 0.289 | D10: 0.0784 D50: 0.132 D90: 0.211 D99: 0.275 |

TABLE 61

Stability of Dronabinol Ophthalmic Emulsion AE10C-B Placebo at 5° C.

| | Testing Conditions | | | | |
|---|---|---|---|---|---|
| | Initial | 4 W | 8 W | 12 W | 6 M |
| Appearance | White opaque liquid, no phase separation | White opaque liquid, no phase separation | White opaque liquid, no phase separation | Off-white opaque liquid, no phase separation | White opaque liquid, no phase separation |
| pH | 6.8 | 7.1 | 7.1 | 7.2 | 7.4 |
| Osmolarity | 295 mOsm/L | NA | NA | NA | 297 mOsm/L |
| THC Assay | 0.0% | 0.0% | 0.0% | 0.0% | 0.0% |
| Impurity | RRT 0.2: 5.28% RRT 0.81: 3.49% RRT 1.22: 0.51% RRT 1.27: 1.77% RRT 1.35: 1.96% Total: 13.0% | RRT 0.2: 5.51% RRT 0.81: 3.54% RRT 1.22: 0.45% RRT 1.27: 1.89% RRT 1.35: 2.09% Total: 13.5% | RRT 0.2: 4.64% RRT 0.81: 2.97% RRT 1.22: 0.46% RRT 1.27: 1.56% RRT 1.35: 1.78% Total: 11.4% | RRT 0.2: 5.67% RRT 0.50: 0.10% RRT 0.81: 3.59% RRT 1.22: 0.59% RRT 1.27: 2.05% RRT 1.35: 2.54% RRT 1.40: 0.27% Total: 14.8% | RRT 0.2: 5.47% RRT 0.81: 3.29% RRT 1.22: 0.65% RRT 1.27: 1.86% RRT 1.35: 2.40% RRT 1.40: 0.22% Total: 13.9% |
| PSD | D10: 0.0785 D50: 0.133 D90: 0.216 D99: 0.306 | D10: 0.0797 D50: 0.132 D90: 0.212 D99: 0.307 | D10: 0.0793 D50: 0.132 D90: 0.213 D99: 0.305 | D10: 0.0805 D50: 0.134 D90: 0.216 D99: 0.294 | D10: 0.0785 D50: 0.132 D90: 0.215 D99: 0.351 |

TABLE 62

Stability of Dronabinol Ophthalmic Emulsion AE10C-B Placebo at 25° C./60% RH

| | Testing Conditions | | | | |
|---|---|---|---|---|---|
| | Initial | 4 W | 8 W | 12 W | 6 M |
| Appearance | White opaque liquid, no phase separation | Pale yellow opaque liquid, no phase separation | Pale yellow opaque liquid, no phase h separation | Yellow opaque liquid, no phase separation | Very pale yellow, opaque liquid, no phase separation |
| pH | 6.8 | 7.0 | 6.9 | 6.9 | 7.0 |
| Osmolarity | 295 mOsm/L | NA | NA | NA | 298 mOsm/L |
| THC Assay | 0.0% | 0.0% | 0.0% | 0.0% | 0.0% |
| Impurity | RRT | RRT | RRT | RRT | RRT |

TABLE 62-continued

Stability of Dronabinol Ophthalmic Emulsion AE10C-B Placebo at 25° C./60% RH

| | Testing Conditions | | | | |
|---|---|---|---|---|---|
| | Initial | 4 W | 8 W | 12 W | 6 M |
| | 0.2: 5.28% RRT | 0.2: 5.37% RRT | 0.2: 4.59% RRT | 0.2: 5.52% RRT | 0.2: 5.47% RRT |
| | 0.81: 3.49% RRT | 0.25: 0.10% RRT | 0.81: 2.18% RRT | 0.26: 0.19% RRT | 0.81: 2.44% RRT |
| | 1.22: 0.51% RRT | 0.5: 0.38% RRT | 1.22: 0.45% RRT | 0.50: 0.33% RRT | 1.22: 0.725% RRT |
| | 1.27: 1.77% RRT | 0.81: 2.13% RRT | 1.27: 1.55% RRT | 0.81: 1.69% RRT | 1.27: 1.89% RRT |
| | 1.35: 1.96% Total: 13.0% | 1.22: 0.42% RRT | 1.35: 1.77% Total: 10.5% | 1.22: 0.58% RRT | 1.35: 2.41% RRT |
| | | 1.27: 1.82% RRT | | 1.27: 1.95% RRT | 1.40: 0.19% Total: 13.1% |
| | | 1.35: 2.07% Total: 11.9% | | 1.35: 2.51% RRT | |
| | | | | 1.40: 0.27% Total: 13.0% | |
| PSD | D10: 0.0785 D50: 0.133 D90: 0.216 D99: 0.306 | D10: 0.0781 D50: 0.131 D90: 0.213 D99: 0.306 | D10: 0.0797 D50: 0.132 D90: 0.212 D99: 0.307 | D10: 0.0804 D50: 0.134 D90: 0.216 D99: 0.292 | D10: 0.0789 D50: 0.133 D90: 0.217 D99: 0.303 |

TABLE 63

Stability of Dronabinol Ophthalmic Emulsion AE10C-B 0.05% Active at −20° C.

| | Testing Conditions | | | | | |
|---|---|---|---|---|---|---|
| | Initial | 4 W | 8 W | 12 W | 6 M | 12 M |
| Appearance | White opaque liquid, no phase separation | White opaque liquid, no phase separation | White opaque liquid, no phase separation | White opaque liquid, no phase separation | White opaque liquid, no phase separation | Off-white opaque liquid, no phase separation |
| pH | 7.1 | 7.2 | 7.0 | 7.2 | 7.4 | 7.6 |
| Osmolarity | 298 mOsm/L | NA | NA | NA | 300 mOsm/L | 301 mOsm/L |
| THC Assay | 99.0% | 98.5% | 94.1% | 98.6% | 98.2% | 102.2% |
| Impurity | RRT 0.3:0.14% RRT 0.40:0.40% RRT 0.46:0.55% RRT 0.56:0.23% RRT 0.60:0.08% RRT 0.62:0.31% CBD:0.51% CBN:0.71% RRT 0.93:0.54% Total: 3.0% | RRT 0.3:0.09% RRT 0.40:0.72% RRT 0.46:0.60% RRT 0.56:0.16% RRT 0.60:0.30% RRT 0.62:0.31% CBN:0.76% RRT 0.93:0.52% Total: 3.5% | RRT 0.3:0.09% RRT 0.40:0.53% RRT 0.46:0.53% RRT 0.56:0.14% RRT 0.60:0.23% RRT 0.62:0.36% CBN:0.63% RRT 0.93:0.50% Total: 3.0% | RRT 0.3:0.12% RRT 0.40:0.69% RRT 0.46:0.58% RRT 0.56:0.09% RRT 0.60:0.31% RRT 0.62:0.46% CBN:0.71% RRT 0.93:0.47% Total: 3.4% | RRT 0.3:0.12% RRT 0.40:0.65% RRT 0.46:0.63% RRT 0.54:0.23% RRT 0.56:0.17% RRT 0.60:0.32% RRT 0.62:0.49% RRT 0.74:0.24% CBN:0.70% RRT 0.93:0.40% Total: 4.0% | RRT 0.3:0.17% RRT 0.40:0.62% RRT 0.46:0.59% RRT 0.54:0.25% RRT 0.56:0.14% RRT 0.60:0.31% RRT 0.62:0.48% CBN:0.66% RRT 0.93:0.30% Total: 3.6% |
| PSD | D10: 0.0791 D50: 0.132 D90: 0.213 D99: 0.307 | D10: 0.0797 D50: 0.133 D90: 0.214 D99: 0.308 | D10: 0.0790 D50: 0.131 D90: 0.210 D99: 0.293 | D10: 0.0767 D50: 0.129 D90: 0.210 D99: 0.284 | D10: 0.0770 D50: 0.129 D90: 0.206 D99: 0.271 | D10: 0.0732 D50: 0.125 D90: 0.204 D99: 0.300 |

TABLE 64

Stability of Dronabinol Ophthalmic Emulsion AE10C-B 0.05% Active at 5° C.

| | Testing Conditions | | | | |
|---|---|---|---|---|---|
| | Initial | 4 W | 8 W | 12 W | 6 M |
| Appearance | White opaque liquid, no phase separation | White opaque liquid, no phase separation | White opaque liquid, no phase separation | White opaque liquid, no phase separation | White opaque liquid, no phase separation |
| pH | 7.1 | 7.1 | 7.0 | 7.1 | 7.2 |
| Osmolarity | 298 mOsm/L | NA | NA | NA | 301 mOsm/L |
| THC Assay | 99.0% | 99.0% | 93.1% | 96.9% | 97.3% |
| Impurity | RRT 0.3: 0.14% RRT 0.40: 0.40% RRT 0.46: 0.55% RRT 0.56: 0.23% RRT 0.60: 0.08% RRT 0.62: 0.31% CBD: 0.51% CBN: 0.71% RRT 0.93: 0.54% Total: 3.0% | RRT 0.3: 0.11% RRT 0.40: 1.06% RRT 0.46: 0.61% RRT 0.56: 0.16% RRT 0.60: 0.38% RRT 0.62: 0.19% RRT 0.66: 0.13% CBN: 0.82% RRT 0.93: 0.49% Total: 4.0% | RRT 0.3: 0.10% RRT 0.40: 1.13% RRT 0.46: 0.55% RRT 0.56: 0.12% RRT 0.60: 0.34% RRT 0.62: 0.08% CBN: 0.70% RRT 0.93: 0.47% Total: 3.5% | RRT 0.3: 0.15% RRT 0.40: 1.62% RRT 0.46: 0.63% RRT 0.56: 0.08% RRT 0.60: 0.57% RRT 0.74: 0.20% CBN: 0.77% RRT 0.93: 0.48% Total: 4.5% | RRT 0.29: 0.23% RRT 0.3: 0.14% RRT 0.40: 1.54% RRT 0.46: 0.66% RRT 0.54: 0.21% RRT 0.56: 0.12% RRT 0.60: 0.49% RRT 0.72: 0.29% RRT 0.74: 0.16% CBN: 0.87% RRT 0.93: 0.44% Total: 5.3% |
| PSD | D10: 0.0791 D50: 0.132 D90: 0.213 D99: 0.307 | D10: 0.0795 D50: 0.133 D90: 0.213 D99: 0.308 | D10: 0.0784 D50: 0.130 D90: 0.210 D99: 0.305 | D10: 0.0818 D50: 0.133 D90: 0.208 D99: 0.395 | D10: 0.0754 D50: 0.129 D90: 0.214 D99: 0.328 |

TABLE 65

Stability of Dronabinol Ophthalmic Emulsion AE10C-B 0.05% Active at 25° C./60% RH

| | Testing Conditions | | | | |
|---|---|---|---|---|---|
| | Initial | 4 W | 8 W | 12 W | 6 M |
| Appearance | White opaque liquid, no phase separation | Off-white opaque liquid, no phase separation | Off-white opaque liquid, no phase separation | Slightly yellow opaque liquid, no phase separation | Very pale yellow opaque liquid, no phase separation |
| pH | 7.1 | 7.0 | 7.8 | 7.1 | 7.0 |
| Osmolarity | 298 mOsm/L | NA | NA | NA | 302 mOsm/L |
| THC Assay | 99.0% | 96.0% | 89.7% | 93.0% | 92.5% |
| Impurity | RRT 0.3: 0.14% RRT 0.40: 0.40% RRT 0.46: 0.55% RRT 0.56: 0.23% RRT 0.60: 0.08% RRT 0.62: 0.31% CBD: 0.51% CBN: 0.71% RRT 0.93: 0.54% Total: 3.0% | RRT 0.3: 0.09% RRT 0.40: 1.96% RRT 0.46: 0.82% RRT 0.56: 0.15% RRT 0.60: 0.51% RRT 0.66: 0.43% CBN: 0.97% RRT 0.93: 0.55% Total: 5.5% | RRT 0.3: 0.09% RRT 0.40: 1.85% RRT 0.46: 0.71% RRT 0.56: 0.12% RRT 0.60: 0.41% RRT 0.86: 0.17% CBN: 0.85% RRT 0.93: 0.57% Total: 4.8% | RRT 0.3: 0.12% RRT 0.40: 2.54% RRT 0.46: 0.82% RRT 0.56: 0.12% RRT 0.60: 0.45% CBN: 0.96% RRT 0.93: 0.61% Total: 5.6% | RRT 0.3: 0.09% RRT 0.40: 2.28% RRT 0.46: 0.75% RRT 0.54: 0.24% RRT 0.56: 0.08% RRT 0.60: 0.41% CBN: 1.22% RRT 0.93: 0.59% Total: 5.7% |
| PSD | D10: 0.0791 D50: 0.132 | D10: 0.0769 D50: 0.129 | D10: 0.0772 D50: 0.129 | D10: 0.0811 D50: 0.134 | D10: 0.0766 D50: 0.130 |

TABLE 65-continued

Stability of Dronabinol Ophthalmic Emulsion AE10C-B 0.05% Active at 25° C./60% RH

| | Testing Conditions | | | | |
|---|---|---|---|---|---|
| | Initial | 4 W | 8 W | 12 W | 6 M |
| | D90: 0.213 | D90: 0.212 | D90: 0.206 | D90: 0.212 | D90: 0.214 |
| | D99: 0.307 | D99: 0.332 | D99: 0.270 | D99: 0.276 | D99: 0.329 |

TABLE 66

Stability of Dronabinol Ophthalmic Emulsion AE10C-B 0.5% Active at −20° C.

| | Testing Conditions | | | | | |
|---|---|---|---|---|---|---|
| | Initial | 4 W | 8 W | 12 W | 6 M | 12 M |
| Appearance | White opaque liquid, no phase separation | White opaque liquid, no phase separation | White opaque liquid, no phase separation | White opaque liquid, no phase separation | White opaque liquid, no phase separation | White opaque liquid, no phase separation |
| pH | 7.1 | 7.1 | 7.1 | 7.1 | 7.2 | 7.6 |
| Osmolarity | 295 mOsm/L | NA | NA | NA | 296 mOsm/L | 298 mOsm/L |
| THC Assay | 95.7% | 97.3% | 94.2% | 96.8% | 90.4% | 100.2% |
| Impurity | RRT 0.40:0.47% RRT 0.46:0.37% RRT 0.56:0.21% RRT 0.62:0.26% CBD:0.25% CBN:0.75% RRT 0.93:0.53% Total: 2.8% | RRT 0.40:0.74% RRT 0.46:0.34% RRT 0.60:0.28% RRT 0.62:0.24% CBN:0.85% RRT 0.93:0.55% Total: 3.0% | RRT 0.40:0.31% RRT 0.46:0.28% RRT 0.60:0.21% RRT 0.66:0.37% CBN:0.65% RRT 0.93:0.50% Total: 2.3% | RRT 0.40:0.35% RRT 0.46:0.28% RRT 0.56:0.09% RRT 0.62:0.23% CBD:0.45% CBN:0.75% RRT 0.93:0.40% Total: 2.6% | RRT 0.40:0.39% RRT 0.46:0.32% RRT 0.56:0.10% RRT 0.60:0.25% RRT 0.66:0.44% RRT 0.72:0.08% CBN:0.80% RRT 0.93:0.37% Total: 2.7% | RRT 0.40:0.46% RRT 0.46:0.29% RRT 0.56:0.13% RRT 0.60:0.23% RRT 0.66:0.52% CBN:0.80% RRT 0.93:0.36% Total: 2.8% |
| PSD | D10: 0.0752 D50: 0.128 D90: 0.210 D99: 0.278 | D10: 0.0782 D50: 0.132 D90: 0.213 D99: 0.294 | D10: 0.0780 D50: 0.129 D90: 0.207 D99: 0.292 | D10: 0.0752 D50: 0.128 D90: 0.210 D99: 0.278 | D10: 0.0761 D50: 0.129 D90: 0.213 D99: 0.473 | D10: 0.0779 D50: 0.132 D90: 0.211 D99: 0.277 |

TABLE 67

Stability of Dronabinol Ophthalmic Emulsion AE10C-B 0.5% Active at 5° C.

| | Testing Conditions | | | | |
|---|---|---|---|---|---|
| | Initial | 4 W | 8 W | 12 W | 6 M |
| Appearance | White opaque liquid, no phase separation | White opaque liquid, no phase separation | White opaque liquid, no phase separation | White opaque liquid, no phase separation | White opaque liquid, no phase separation |
| pH | 7.1 | 7.0 | 6.9 | 7.0 | 7.3 |
| Osmolarity | 295 mOsm/L | NA | NA | NA | 298 mOsm/L |
| THC Assay | 95.7% | 97.8% | 95.1% | 96.4% | 91.0% |
| Impurity | RRT 0.40: 0.47% RRT 0.46: 0.37% RRT 0.56: 0.21% RRT 0.62: 0.26% CBD: 0.25% CBN: 0.75% RRT | RRT 0.30: 0.23% RRT 0.40: 1.11% RRT 0.46: 0.38% RRT 0.56: 0.10% RRT 0.60: 0.53% RRT | RRT 0.30: 0.20% RRT 0.40: 1.15% RRT 0.46: 0.45% RRT 0.56: 0.14% RRT 0.60: 0.58% RRT | RRT 0.40: 1.14% RRT 0.46: 0.36% RRT 0.60: 0.37% CBN: 0.94% RRT 0.93: 0.41% Total: 3.2% | RRT 0.30: 0.06% RRT 0.40: 1.28% RRT 0.46: 0.46% RRT 0.56: 0.07% RRT 0.60: 0.36% RRT |

TABLE 67-continued

Stability of Dronabinol Ophthalmic Emulsion AE10C-B 0.5% Active at 5° C.

| | Testing Conditions | | | | |
|---|---|---|---|---|---|
| | Initial | 4 W | 8 W | 12 W | 6 M |
| | 0.93: 0.53%<br>Total: 2.8% | 0.66: 0.09%<br>CBN: 0.94%<br>RRT<br>0.93: 0.53%<br>Total: 3.9% | 0.66: 0.11%<br>CBN: 0.85%<br>RRT<br>0.93: 0.37%<br>Total: 3.9% | | 0.72: 0.14%<br>CBN: 1.00%<br>RRT<br>0.93: 0.47%<br>Total: 3.8% |
| PSD | D10: 0.0752<br>D50: 0.128<br>D90: 0.210<br>D99: 0.278 | D10: 0.0798<br>D50: 0.134<br>D90: 0.213<br>D99: 0.280 | D10: 0.0786<br>D50: 0.131<br>D90: 0.209<br>D99: 0.278 | D10: 0.0782<br>D50: 0.131<br>D90: 0.211<br>D99: 0.282 | D10: 0.0775<br>D50: 0.131<br>D90: 0.212<br>D99: 0.282 |

TABLE 68

Stability of Dronabinol Ophthalmic Emulsion AE10C-B 0.5% Active at 25° C./60% RH

| | Testing Conditions | | | | |
|---|---|---|---|---|---|
| | Initial | 4 W | 8 W | 12 W | 6 M |
| Appearance | White opaque liquid, no phase separation | White opaque liquid, no phase separation | White opaque liquid, no phase separation | Off-white opaque liquid, no phase separation | Off-white opaque liquid, no phase separation |
| pH | 7.1 | 6.9 | 6.7 | 6.7 | 7.1 |
| Osmolarity | 295 mOsm/L | NA | NA | NA | 298 mOsm/L |
| THC Assay | 95.7% | 94.8% | 93.8% | 95.1% | 87.7% |
| Impurity | RRT<br>0.40: 0.47%<br>RRT<br>0.46: 0.37%<br>RRT<br>0.56: 0.21%<br>RRT<br>0.62: 0.26%<br>CBD: 0.25%<br>CBN: 0.75%<br>RRT<br>0.93: 0.53%<br>Total: 2.8% | RRT<br>0.40: 1.29%<br>RRT<br>0.46: 0.47%<br>RRT<br>0.56: 0.11%<br>RRT<br>0.60: 0.39%<br>CBN: 1.09%<br>RRT<br>0.93: 0.62%<br>Total: 4.0% | RRT<br>0.40: 1.16%<br>RRT<br>0.46: 0.41%<br>RRT<br>0.60: 0.30%<br>CBN: 0.99%<br>RRT<br>0.93: 0.68%<br>Total: 3.5% | RRT<br>0.40: 1.38%<br>RRT<br>0.46: 0.46%<br>RRT<br>0.60: 0.34%<br>CBN: 1.24%<br>RRT<br>0.93: 0.47%<br>Total: 3.9% | RRT<br>0.40: 1.54%<br>RRT<br>0.46: 0.48%<br>RRT<br>0.60: 0.31%<br>CBN: 1.46%<br>RRT<br>0.93: 0.59%<br>Total: 4.4% |
| PSD | D10: 0.0752<br>D50: 0.128<br>D90: 0.210<br>D99: 0.278 | D10: 0.0792<br>D50: 0.133<br>D90: 0.212<br>D99: 0.282 | D10: 0.0795<br>D50: 0.134<br>D90: 0.213<br>D99: 0.276 | D10: 0.0768<br>D50: 0.130<br>D90: 0.211<br>D99: 0.284 | D10: 0.0763<br>D50: 0.130<br>D90: 0.213<br>D99: 0.303 |

Example 57: Mouse Study on TOP Lowering Effects

In this example, the effects of Dronabinol and Timolol on mouse intraocular pressure (TOP) and aqueous humor dynamics was investigated.
Methods & Materials
Animals Female C57BL/6J mice (Jackson Laboratories, Bar Harbor, Me.; age 2-3 months) were kept in 12 h light/12 h dark conditions (lights on 0600 h) and fed with standard chow. All experimental procedures were conducted in accordance with the ARVO Statement for the Use of Animals in Ophthalmic and Vision Research, and the University of North Texas Health Science Center Institutional Animal Care and Use Committee Regulations and Guidelines.
Ophthalmic Formulations Dronabinol ophthalmic solutions (0.05% and 0.5%) and the corresponding vehicle were provided by Rhodes Technologies. Timolol maleate 0.5% (Hi.Tech Pharmacal) was purchased. Formulation AE10C-B was prepared as described above (Table 44).

IOP Measurement

TOP was determined in behaviorally trained conscious animals using a TonoLab® rebound tonometer (Colonial Medical Supply, Franconia, N.H.), in accordance with the procedure set forth in Millar et al., *Invest Ophthalmol Vis. Sci.*, 2015, 56:5764-5776. The indicated formulation was topically administered to one eye of each animal. The contralateral eye was not treated.
Aqueous Humor Dynamics At 2 h after topically administering Dronabinol or vehicle, parameters of aqueous humor dynamics were established in living mice by constant flow infusion as described previously (Millar et al., *Invest. Ophthalmol. Vis. Sci.*, 2015, 56:5764-5776; Millar et al., *Invest. Ophthalmol. Vis. Sci.*, 2011, 52:685-694). Briefly, immediately following bilateral tonometry in anesthetized animals, both eyes received a drop of proparacaine HCl (0.5%) for topical anesthesia, and both anterior chambers were cannulated with a 30G needle (one per eye) connected to previously calibrated BLPR-2 flow-through pressure transducers (World Precision Instruments (WPI), Sarasota, Fla.) for the continuous determination of pressure. A drop of PBS was also given to each eye topical ocular to prevent corneal drying. The opposing end of each transducer was connected to a 3-way valve, which in turn was connected to: (a) a 50 FAL glass microsyringe (Hamilton Company, Reno, Nev.) filled with sterile PBS loaded into an SP101i microdialysis infusion pump (WPI), and (b), an open ended, variable height manometer. Signals from the pressure transducers were passed via a TBM4M Bridge Amplifier (WPI) and a Lab-Trax analog-to-digital converter (WPI) to a computer. Data were recorded using Lab Scribe2 software (WPI).

Aqueous Outflow Facility (C)

The manometer was closed to the circuit and eyes were infused at a flow rate of 0.1 µL/min. When pressure had stabilized, pressure measurements were recorded, and flow rate was increased sequentially to 0.2, 0.3, 0.4, and 0.5 µL/min. Three stabilized pressures (spaced 5 min apart) at each flow rate were recorded. Aqueous outflow facility (C) in each eye of each animal was calculated as the reciprocal of the slope of a plot of Mean Stabilized Pressure as ordinate against Flow Rate as abscissa.

Episcleral Venous Pressure (Pe)

Episcleral venous pressure (Pe) was estimated using the blood reflux method. Briefly, following anterior chamber cannulation, the manometer was opened to the circuit, manometric pressure was set to equal pre-cannulation (anesthetized) TOP, and then manometric pressure was lowered incrementally (at the rate of 1 mmHg/min) until the point at which blood was seen (using a dissection microscope under 30× magnification) to reflux into the scleral collector channels and then Schlemm's canal. The manometric pressure at which Schlemm's canal was seen to fill with refluxed blood was regarded as Pe.

Uveoscleral Outflow Rate (Fu)

After completion of the above measurements, animals were euthanized by anesthetic overdose and, 20 min following euthanasia, C was measured again. Thus values for Clive and C dead were obtained. Following euthanasia, both aqueous humor formation rate (Fin) and Pe are equal to zero, and via algebraic rearrangement of the modified Goldmann equation $\{IOP=[(Fin-Fu)/C]+Pe\}$, values for Fu were thus calculated for each individual perfusion rate and corresponding TOP. The mean of those resultant 5 values was reported as Fu.

Computation of Aqueous Humor Formation Rate (Fin)

Aqueous Humor Formation Rate (Fin) was calculated for each eye by further algebraic rearrangement of the modified Goldmann equation: $Fin=[C\times(IOP-Pe)]+Fu$.

Statistical Analysis

The 2-tailed unpaired Student's t-test was used for comparison of results at the same time point between two study groups. P values of less than 0.05 were considered significant. All data are presented as mean±SEM.

Results

Figure 24:
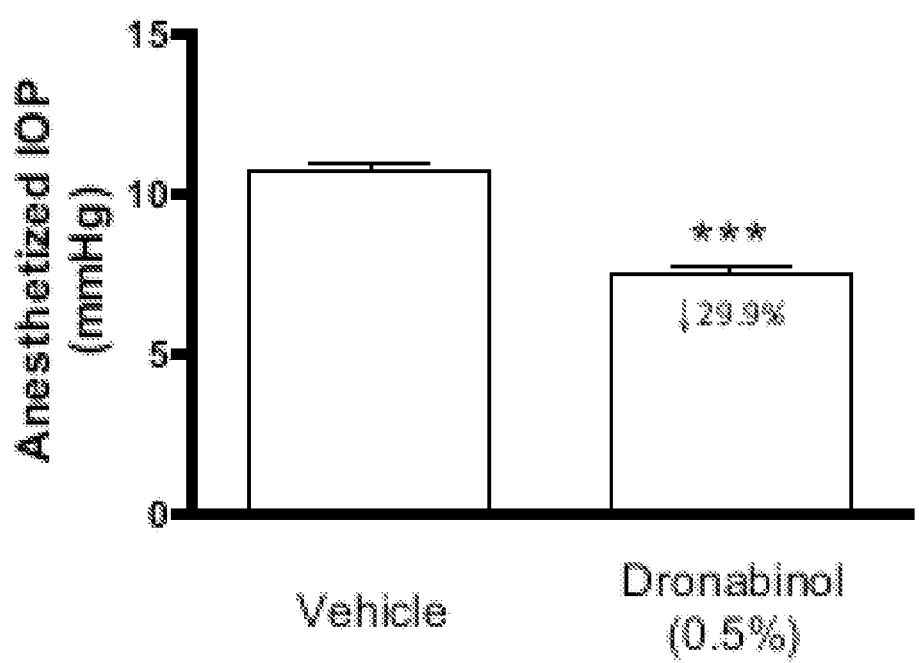
FIG. 24 is a bar graph showing the effect of Dronabinol on intraocular pressure in anesthetized mice.

Effects of Dronabinol ophthalmic solutions (0.05% & 0.5%) on conscious mouse IOP Topical ocular administration of a single drop (5 µL) of Dronabinol ophthalmic solution (0.05% & 0.5%) significantly lowered mouse TOP. The contralateral untreated Control eye was not affected, suggesting a local effect (FIG. 24). The TOP reduction of both formulations was still significant at 24 h after treatment, though their maximal effects peaked at 2-6 h (Dronabinol 0.05%=−22.3% @ 6 h; Dronabinol 0.5%=−25.8% @ 2 h). In contrast, the vehicle did not affect TOP (FIG. 24). As a positive control, timolol (0.5%) lowered mouse TOP as expected (FIG. 24). No ocular, systemic, or behavioral adverse effects were observed in this study.

Effects Dronabinol Ophthalmic Emulsion (0.5%) on Mouse Aqueous Humor Dynamics

Figure 25:
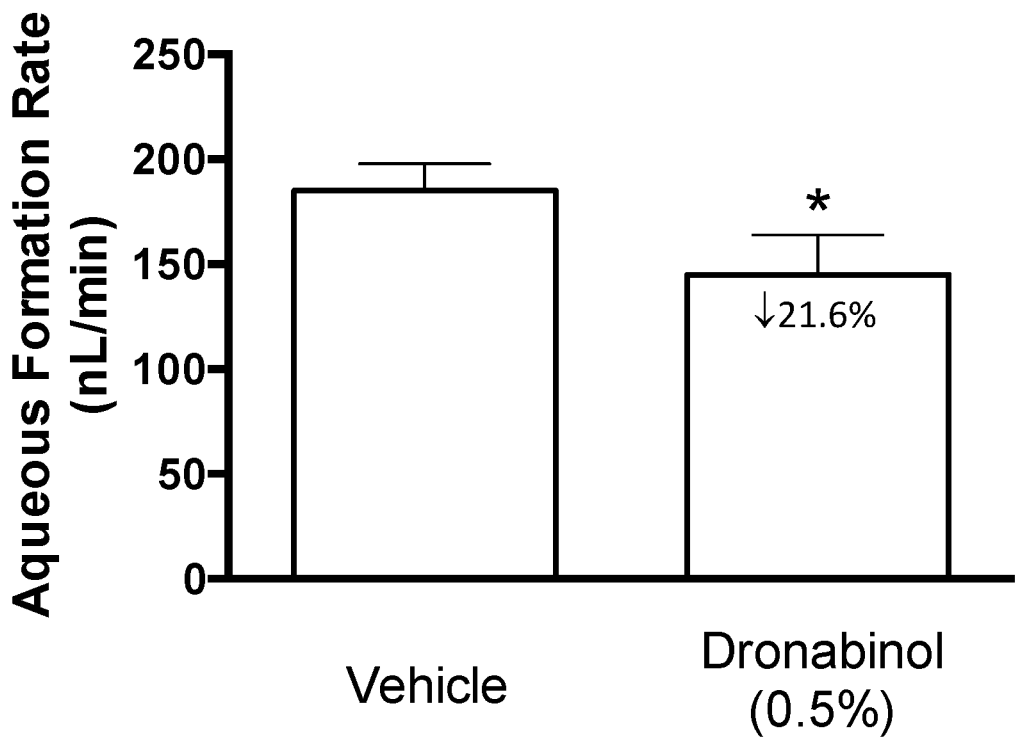
FIG. 25 is a bar graph showing the effect of Dronabinol on the aqueous humor formulation rate in a mouse model.
Figure 26:
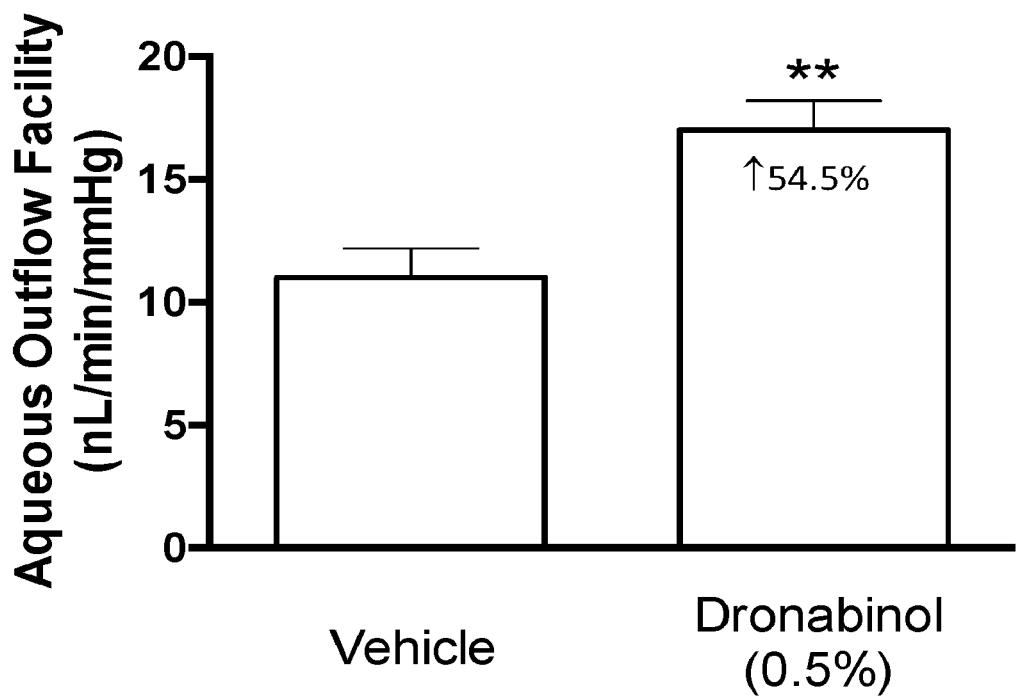
FIG. 26 is a bar graph showing the effect of Dronabinol on the aqueous outflow facility in a mouse model.
Figure 27:
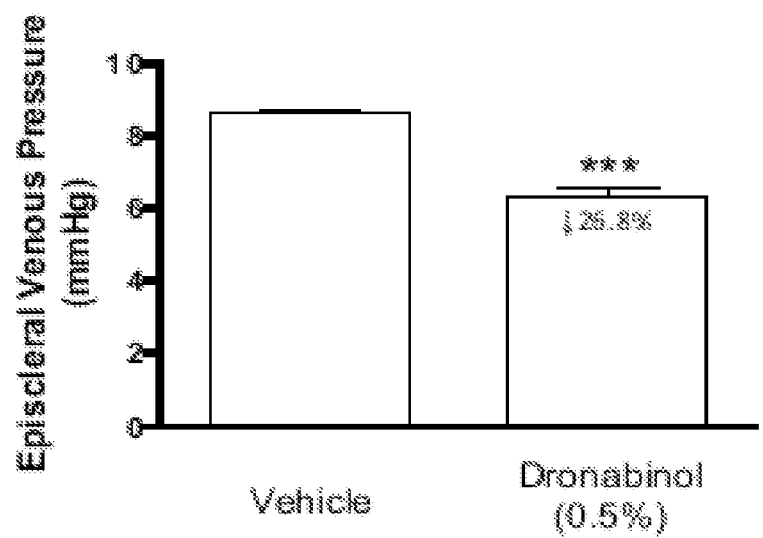
FIG. 27 is a bar graph showing the effect of Dronabinol on the episcleral venous pressure in a mouse model.
Figure 28:
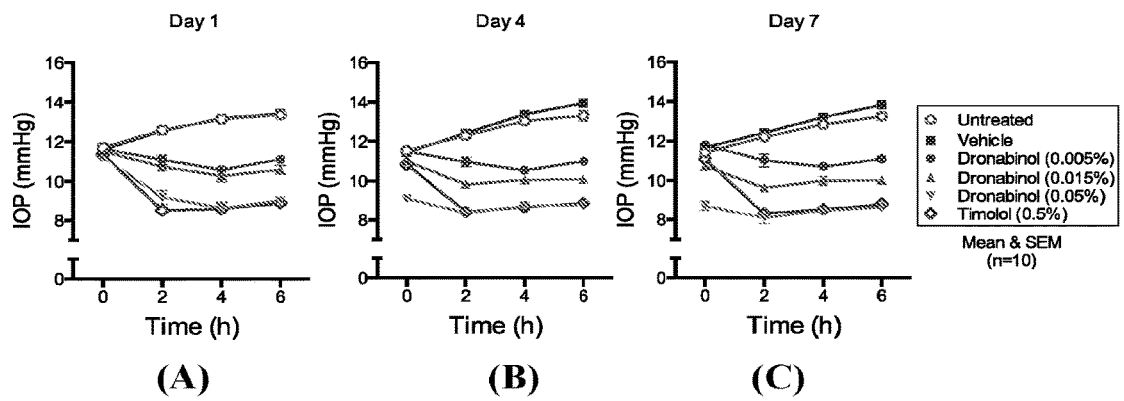
FIGS. 28 (A)-(C) show comparison of IOP effects (mmHg) of repeated dosing of the Dronabinol formulations, vehicle, and Timolol.

Since 2 h after treatment with 0.5% Dronabinol produced the optimal TOP reduction in the mouse, this drug concentration and time point were selected for the aqueous humor dynamics study. As shown in FIG. 25, the Dronabinol ophthalmic emulsion of the invention affected several parameters. It significantly lowered TOP by 29.9% in the anesthetized animals (FIG. 25), confirming the TOP results in conscious animals shown in FIG. 24. It simultaneously lowered aqueous humor formulation rate (−21.6%) (FIG. 26), increased aqueous outflow facility (54.5%) (FIG. 27), and reduced episcleral venous pressure (−26.8%) (FIG. 28). All of these actions are expected to contribute to the IOP-lowering effect of the dronabinol ophthalmic emulsion of the invention. No ocular adverse effect was observed in this study.

The above data demonstrates that the dronabinol ophthalmic emulsion of the invention is an efficacious IOP-lowering agent, with a unique combination of mechanisms of action on both aqueous formation and aqueous outflow facility. Since the elevation of IOP in primary open angle glaucoma (POAG) patients is due to a reduction in aqueous outflow facility (trabecular outflow) the outflow effect by the dronabinol ophthalmic emulsion of the invention is expected to be especially beneficial to POAG patients. In contrast, currently commonly used glaucoma medications do not affect aqueous outflow facility: prostanoids increase uveoscleral outflow; beta-blockers and carbonate anhydrase inhibitors (CAIS) suppress aqueous formation. It is believed that the dronabinol ophthalmic emulsion of the invention is a highly effective therapy for treating glaucoma.

Example 58: Repeated Dosing Study on IOP Lowering Effects

Study protocol is similar to Dose-Response Relationship Study described above, except that the animals are divided into three groups (as specified below). A single 5 µL drop was instilled topically onto one eye of each mouse twice daily starting at time 0 of Day 1.

The contralateral eye was untreated. IOP of both eyes was measured at −1 h (baseline), 2 h, 4 h, 6 h, 8 h, 12 h. If the IOP did not return to baseline at the 12 h time point, additional TOP measurements were conducted at 24 h, 30 h, 48 h, and once daily for up to 7 days, or until TOP returns to baseline. In addition to TOP measurement, animals were evaluated for possible ocular and gross systemic adverse effects.

Group 1: Vehicle
Group 2: Dronabinol (optimal concentration determined in studies above)
Group 3: Timolol (0.5%)

Figure 29:
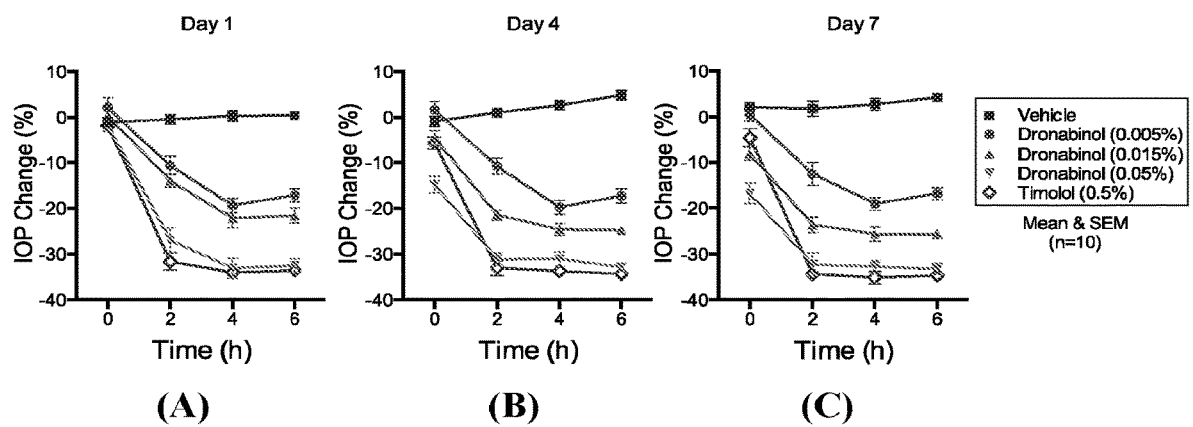
FIGS. 29 (A)-(C) show comparison of IOP effects (% change) of repeated dosing of the Dronabinol formulations, vehicle, and Timolol.

Results: The results are presented in FIGS. 28 and 29, which illustrate comparison of TOP effects of the Dronabinol formulations, vehicle, and Timolol. The formulations were administered twice daily at 8-9 AM (Time 0) and 4-5 PM starting Day 1 till Day 7. The upper panel reports TOP values at the indicated time points after dosing (IOP at Time 0 was obtained immediately prior to the morning dosing) of Days 1, 4, and 7. The bottom panel represents % IOP change compared to the contralateral untreated eye, whose IOP defines 100%. Data are shown as mean±SEM.

All tested Dronabinol formulations (with 0.005%, 0.015%, and 0.05% of API) produced significant intraocular pressure (TOP) reduction. No tachyphylaxis or adverse effect was observed during 7-day twice daily dosing.

Dronabinol formulations lowered IOP in a dose-dependent manner. The efficacy of 0.05% Dronabinol formulation was similar to that of Timolol (0.5%).

Compared to the contralateral untreated eyes, vehicle did not lower IOP, Dronabinol formulation (0.005%) produced a maximum of 19.8% IOP reduction, Dronabinol formulation (0.015%) produced a maximum of 25.7% IOP reduction, Dronabinol (0.05%) produced a maximum of 33.2% IOP reduction, while Timolol (0.5%) produced a maximum of 35.1% IOP reduction.

At Days 4 & 7, the baseline IOP was lowered in the 0.05% Dronabinol-treated eyes, but not in other groups, suggesting duration of action>16 hours. Timolol (0.5%) did not produce this prolonged IOP reduction.

Example 59: Neuroprotection Animal Study

Neuroprotection against mouse retinal ischemia/reperfusion damage can be tested according to an as described in: Nashine, S. et al., *Invest. Ophthalmol. Vis. Sci.*, 2015, 56:221-231.

Specifically, one eye of an adult C57BL/6J mouse is injected intravitreally with one of the emulsion compositions of the invention (2 µL), and subsequently subjected to retinal ischemia/reperfusion after a 30-min time period. Sample size n=36/group/time point is used. At 0 (before injection), 7, 14, and 28 d after injection, animals are evaluated in vivo by spectral domain optical coherence tomography (SD-OCT) for retina thickness and electroretinography (ERG) for retinal ganglion cell (RGC) function and then euthanized for post-mortem assessment of RGC density (retinal flatmount, n=10 each time point of each group), morphology of retina (H&E & immunohistochemistry in cross-sections, n=6), morphology of brain visual centers (H&E & immunohistochemistry in cross-sections, n=6), and biochemical/apoptotic changes in retina (qPCR and western blot, n=10). Contralateral uninjured eye serves as a control.

The study results are assessed using methods and parameters known in the art (see S. Choudhury, Y. Liu, A. Clark and L. Pang, *Caspase-7: a critical mediator of optic nerve injury-induced retinal ganglion cell death*, Molecular Neurodegeneration, (2015) 10:40).

| Test Group | Description |
|---|---|
| Group 1 | Vehicle (PBS), without ischemia/reperfusion |
| Group 2 | Dronabinol (5 nmol), without ischemia/reperfusion |
| Group 3 | Vehicle (PBS), with ischemia/reperfusion |
| Group 4 | (5 nmol), with ischemia/reperfusion |

Example 60: Neuroprotection Animal Study

Neuroprotection against mouse optic nerve injury-induced damage can be tested as described in: Choudhury et al., Mol. Neurodegener. (2015) 10:40.

One eye of adult C57BL/6J mouse is injected intravitreally with one of the compositions of the invention (2 µL), followed by optic nerve crush (Choudhury et al., *Mol. Neurodegener*. (2015) 10:40). Sample size n=36/group/time point can be used. At 0 (before injection), 7, 14, and 28 d after injection, animals are evaluated in vivo by SD-OCT for retina thickness and ERG for RGC function, then euthanized for post-mortem assessment of RGC density (retinal flatmount, n=10 each time point of each group), morphology of retina (H&E & immunohistochemistry in cross-sections, n=6), morphology of brain visual centers (H&E & immunohistochemistry in cross-sections, n=6), biochemical/apoptotic changes in retina (qPCR and western blot, n=10). Contralateral uninjured eye can serve as control.

| Test Group | Description |
|---|---|
| Group 1 | Vehicle (PBS), without optic nerve injury |
| Group 2 | Dronabinol (5 nmol), without optic nerve injury |
| Group 3 | Vehicle (PBS), with optic nerve injury |
| Group 4 | Dronabinol (5 nmol), with optic nerve injury |

The neuroprotection effects afforded by the composition(s) of the invention are assessed using methods and tools known in the art, for example, densitometry analysis of western blot image, and retinal layer thickness assessment by spectral domain-optical coherence tomography (SD-OCT) (see S. Choudhury et al., Caspase-7: a critical mediator of optic nerve injury-induced retinal ganglion cell death, Molecular Neurodegeneration, (2015) 10:40).

Various modifications of the invention, in addition to those described herein, will be apparent to those skilled in the art from the foregoing description. Such modifications are also intended to fall within the scope of the appended claims. Each reference cited in the present application, including all patents, patent applications, and non-patent literature, is incorporated herein by reference in its entirety for all purposes.

What is claimed is:

1. An emulsion composition, comprising:
about 0.005% (w/w) to about 0.5% (w/w) of (−)-trans-$\Delta^9$-tetrahydrocannabinol, or a pharmaceutically acceptable salt thereof;
about 1.5% (w/w) to about 2.0% (w/w) of sesame oil;
about 0.5% (w/w) to about 2% (w/w) of polyoxyethylene sorbitan monooleate;
about 2.5% (w/w) glycerin;
about 0.03% (w/w) butylated hydroxytoluene (BHT) and/or 0.03% (w/w) beta hydroxy acid (BHA); and
water,
wherein the ratio (w/w) of oil to water in the composition is in the range of about 1:20 to about 1:100, the emulsion comprises an oil phase component comprising a plurality of oil droplets dispersed with an aqueous phase component, wherein at least 90% of the oil droplets in the emulsion are less than about 200 nm in diameter, wherein the emulsion remains stable after being stored at a condition selected from the group consisting of: at least two years at about −18° C.; at least three months at about 4° C.; and at least one month at about 23° C., such that there is an absence of visible phase separation between the oil phase component and the aqueous phase component after such storage condition, the (−)-trans-$\Delta^9$-tetrahydrocannabinol remains chemically stable in the composition such that at least about 90% (w/w) of the initial (−)-trans-$\Delta^9$-tetrahydrocannabinol content in the emulsion is present after exposure of the emulsion to the storage condition.

2. A method of treating an ophthalmic condition in a subject in need thereof, the method comprising administering to the eye of the subject a therapeutically effective amount of the emulsion composition of claim 1, wherein said method provides ocular neuroprotection to the subject.

3. The method of claim 2, wherein the subject is suffering from or is at substantial risk of developing a neuropathic condition.

4. The method of claim 3, wherein the neuropathic condition is a blinding eye disease or neuropathic pain.

5. The method of claim 3, wherein the neuropathic condition is a disease selected from the group consisting of macular degeneration, retinitis pigmentosa, and glaucoma.

6. A method of preparing the emulsion composition of claim 1, comprising:
combining (−)-trans-$\Delta^9$-tetrahydrocannabinol or a pharmaceutically acceptable salt thereof, sesame oil, polyoxyethylene sorbitan monooleate, and a first portion of water to form a premix;
homogenizing the premix to form a homogenized premix;
adding a second portion of water after the homogenization step to form a bulk sample;
filtering the bulk sample over a membrane to afford the emulsion composition.

7. A method of preparing the emulsion composition of claim 1, comprising:
combining (−)-trans-$\Delta^9$-tetrahydrocannabinol or a pharmaceutically acceptable salt thereof, sesame oil, polyoxyethylene sorbitan monooleate, and a first portion of water to form a premix;
homogenizing the premix at a speed of about 3000 rpm to about 5000 rpm for a time period of about 2 minutes to about 20 minutes to form a homogenized premix;
adjusting the pH of the homogenized premix solution to about 6.5 to about 7.5 to form a neutralized premix;
adding a second portion of water to the neutralized premix to form a bulk sample;
filtering the bulk sample over a membrane having a maximum pore size of about 200 nm to afford the emulsion composition.

8. An emulsion composition, comprising:
about 0.05% (w/w) to about 0.5% (w/w) of (−)-trans-Δ9-tetrahydrocannabinol, or a pharmaceutically acceptable salt thereof;
about 1.5% (w/w) of sesame oil;
about 2% (w/w) of (polyoxyethylene sorbitan monooleate);
about 2.5% (w/w) glycerin;
about 0.03% (w/w) butylated hydroxytoluene (BHT) and/or 0.03% (w/w) beta hydroxy acid (BHA); and
water,
wherein the emulsion comprises an oil phase component comprising a plurality of oil droplets, dispersed with an aqueous phase component, wherein the emulsion remains stable after being stored at a condition selected from the group consisting of: at least two years at about −18° C.; at least three months at about 4° C.; and at least one month at about 23° C., such that about 90% (w/w) of the initial (−)-trans-$\Delta^9$-tetrahydrocannabinol content in the emulsion is present after exposure of the emulsion to the storage condition.

9. The emulsion composition of claim 8, wherein the composition is a topical formulation suitable for administration to the eye.

10. The emulsion composition of claim 8, wherein the ratio (w/w) of oil to water in the composition is in the range of about 1:20 to about 1:100.

11. The emulsion composition of claim 8, wherein the osmolarity of the emulsion is substantially similar to human tear fluid osmolarity.

12. The emulsion composition of claim 11, having an osmolarity of about 300 mOsm/L to about 340 mOsm/L.

13. A method of treating an ophthalmic condition in a subject in need thereof, the method comprising administering to the eye of the subject a therapeutically effective amount of the emulsion composition of claim 8, wherein said method provides ocular neuroprotection to the subject.

14. The method of claim 13, wherein the subject is suffering from or is at substantial risk of developing a neuropathic condition.

15. The method of claim 14, wherein the neuropathic condition is a blinding eye disease or neuropathic pain.

16. The method of claim 14, wherein the neuropathic condition is a disease selected from the group consisting of macular degeneration, retinitis pigmentosa, and glaucoma.

17. A method of treating an ophthalmic condition in a subject identified in need of such treatment, the method comprising administering to the eye of the subject a therapeutically effective amount of the emulsion composition of claim 8.

18. The method of claim 17, wherein the ophthalmic condition is selected from the group consisting of glaucoma, age-related macular degeneration (AMD), ophthalmitis, and conjunctivitis dry eye disease, posterior uveitis, retinitis, uveoretinitis, proliferative vitreoretinopathy, anterior uveitis, episcleritis, scleritis, ocular neuropathic pain and ocular inflammation caused by a non-infectious condition.

19. A method of preparing the emulsion composition of claim 8, comprising:
combining (−)-trans-$\Delta^9$-tetrahydrocannabinol or a pharmaceutically acceptable salt thereof, sesame oil, polyoxyethylene sorbitan monooleate, and a first portion of water to form a premix;
homogenizing the premix to form a homogenized premix;
adding a second portion of water after the homogenization step to form a bulk sample;
filtering the bulk sample over a membrane to afford the emulsion composition.

20. A method of preparing the emulsion composition of claim 8, comprising:
combining (−)-trans-$\Delta^9$-tetrahydrocannabinol or a pharmaceutically acceptable salt thereof, sesame oil, polyoxyethylene sorbitan monooleate, and a first portion of water to form a premix;
homogenizing the premix at a speed of about 3000 rpm to about 5000 rpm for a time period of about 2 minutes to about 20 minutes to form a homogenized premix;
adjusting the pH of the homogenized premix solution to about 6.5 to about 7.5 to form a neutralized premix;
adding a second portion of water to the neutralized premix to form a bulk sample;
filtering the bulk sample over a membrane having a maximum pore size of about 200 nm to afford the emulsion composition.

* * * * *